(12) United States Patent
Li et al.

(10) Patent No.: US 11,820,863 B2
(45) Date of Patent: Nov. 21, 2023

(54) FLUOROSURFACTANTS

(71) Applicant: SPHERE FLUIDICS LIMITED, Babraham (GB)

(72) Inventors: Xin Li, Babraham (GB); Clive A. Smith, Babraham (GB); Alexandra Clay, Babraham (GB); Frank F. Craig, Babraham (GB)

(73) Assignee: SPHERE FLUIDICS LIMITED, Babraham (GB)

( * ) Notice: Subject to any disclaimer, the term of this patent is extended or adjusted under 35 U.S.C. 154(b) by 1401 days.

(21) Appl. No.: 16/303,769

(22) PCT Filed: May 26, 2017

(86) PCT No.: PCT/GB2017/051507
§ 371 (c)(1),
(2) Date: Nov. 21, 2018

(87) PCT Pub. No.: WO2017/203280
PCT Pub. Date: Nov. 30, 2017

(65) Prior Publication Data
US 2020/0017635 A1    Jan. 16, 2020

(30) Foreign Application Priority Data
May 27, 2016   (GB) ...................................... 1609437

(51) Int. Cl.
| | | |
|---|---|---|
| *C08G 65/332* | (2006.01) | |
| *C08G 65/00* | (2006.01) | |
| *C08G 65/333* | (2006.01) | |
| *C08G 65/334* | (2006.01) | |
| *C12Q 1/6806* | (2018.01) | |
| *C09K 23/00* | (2022.01) | |

(52) U.S. Cl.
CPC ....... *C08G 65/3322* (2013.01); *C08G 65/007* (2013.01); *C08G 65/3348* (2013.01); *C08G 65/33344* (2013.01); *C08G 65/33396* (2013.01); *C09K 23/007* (2022.01); *C12Q 1/6806* (2013.01)

(58) Field of Classification Search
CPC .............. C08G 65/3322; C08G 65/007; C08G 65/332
See application file for complete search history.

(56) References Cited

U.S. PATENT DOCUMENTS

| | | | |
|---|---|---|---|
| 3,621,059 A | 11/1971 | Bartlett | |
| 5,227,516 A * | 7/1993 | Tohzuka | ............... C08G 65/007 560/182 |
| 6,638,749 B1 | 10/2003 | Beckman et al. | |
| 8,765,485 B2 | 7/2014 | Link et al. | |
| 2005/0048288 A1 | 3/2005 | Flynn et al. | |
| 2010/0099837 A1* | 4/2010 | Murphy | ............... C08G 65/331 526/321 |
| 2010/0105112 A1* | 4/2010 | Holtze | ................... C08G 81/00 516/27 |
| 2014/0030579 A1 | 10/2014 | Link et al. | |

FOREIGN PATENT DOCUMENTS

| | | | |
|---|---|---|---|
| CN | 1089960 A | 7/1994 | |
| CN | 101016376 | 8/2007 | |
| CN | 201016376 A | 8/2007 | |
| CN | 101321787 A | 12/2008 | |
| CN | 101367932 A | 2/2009 | |
| CN | 102203144 A | 9/2011 | |
| EP | 0338530 A2 | 10/1989 | |
| EP | 0539043 A2 | 4/1993 | |
| EP | 0818489 * | 7/1997 | .............. C08F 14/18 |
| EP | 0818489 A2 | 1/1998 | |
| EP | 0818490 A2 | 1/1998 | |
| EP | 2662135 | 11/2013 | |
| EP | 2662136 | 11/2013 | |
| GB | 1451705 A | 1/1998 | |
| WO | 2005021151 | 3/2005 | |
| WO | 20060040554 | 4/2006 | |
| WO | 2010048482 A2 | 4/2010 | |
| WO | 2014039912 A1 | 3/2014 | |
| WO | 2015015198 | 2/2015 | |

OTHER PUBLICATIONS

Chinese Office Action dated Oct. 10, 2020, for counterpart Chinese Application No. 2017800299439, pp. 1-10, with English translation.

* cited by examiner

*Primary Examiner* — Jane J Zara
(74) *Attorney, Agent, or Firm* — Renner, Kenner, Greive, Bobak, Taylor & Weber

(57) ABSTRACT

The present invention provides a surfactant having a formula selected from the group consisting of: B—((X)$_x$—(CH$_2$)$_a$-A)$_n$(VI), (A-(CH$_2$)$_a$—(X)$_x$—B—(X)$_x$—(CH$_2$)$_a$-A)$_n$ (IV), (A-(CH$_2$)$_a$—(X)$_x$—B)$_n$ (V), and (B)$_n$—(X)$_x$—(CH$_2$)$_a$-A (VII), wherein A is a perfluoropolyether; a is a positive integer; X is either a covalent bond or a linking group; x is a positive integer; B is a polyalkylene oxide unit; n is a positive integer greater than 1 and, in compounds comprising more than one A, B, X, a and x, each may be the same or different. The present invention also relates to methods of making such surfactants, uses of such surfactants and emulsions comprising such surfactants.

26 Claims, 21 Drawing Sheets

Cells in droplets

Droplets containing cells after incubation for 2 hours at 37°C
The scale bar = 100 μm.

Cells in droplets

Droplets containing cells after incubation for 2 hours at 37°C

The scale bar = 100 µm.

Insert shows typical flourescent image for cell viability measurement (Grey dots are viable cells, white ones are dead cells)

FLUOROSURFACTANTS

The present invention relates to a surfactant comprising a particular repeat unit which comprises a perfluoropolyether and a polyalkylene oxide unit. The present invention also relates to methods for making the surfactant, emulsions comprising the surfactant and methods for preparing the emulsions. Additionally the present invention relates to methods using the surfactant and emulsions, and uses of the surfactant and emulsions.

BACKGROUND

Surfactants have been used for many years in the production of stable emulsions for various applications. General background prior art relating to emulsions can be found in the following: U.S. Pat. Nos. 5,587,153; 6,017,546; WO2005/099661; US2004/081633; U.S. Pat. No. 6,379,682; US2002/172703; WO2004/038363; US2005/087122; US2007/275415 and US2008/053205. Conventional surfactants generally comprise a hydrophilic headgroup soluble in an aqueous phase of an emulsion and one or more lipophilic tails soluble in an oil phase of an emulsion.

More recently, surfactant-stabilised emulsions comprising microdroplets of water in a continuous oil phase have found applications in microfluidic technologies, enabling, for example, high throughput screening, enzyme studies, nucleic acid amplification and other biological processes to be conducted. For example, biological assays may be performed in microfluidic devices using a very small quantity of biological material. Further information relating to microfluidic technology can be found in our previous applications WO2009/050512 and WO2015/015199. Other general background prior art on microdroplets can be found in patents/applications in the name of RainDance Technologies Inc., for example WO2008/063227.

In microfluidic applications the use of oils as the continuous phase in emulsion formation/production is beneficial because they have useful microfluidic properties, such as low friction, non-volatility (unlike alcohols), temperature-resistance plus can easily create oil-water emulsions.

However, conventional surfactants are generally not suitable for stabilising emulsions comprising a fluorous oil phase because of solubility issues, plus they are often toxic to biological molecules or toxic to cells, do not form stable emulsions and can hinder gas transfer from the external environment to the inner regions of the emulsion.

New surfactants suitable for stabilising such emulsions are therefore required. Examples of fluorosurfactants have previously been described in WO2008/021123 and U.S. Pat. No. 6,638,749. Often these were still toxic to cells or damaged biological molecules and did not have the correct chemical or temperature properties to provide emulsion stability for biological applications involving temperature cycling (for example the polymerase chain reaction (PCR)) or for long-term studies in emulsion. A need for further suitable surfactants for this use therefore still exists.

SUMMARY OF INVENTION

Viewed from a first aspect the present invention provides a surfactant having a formula selected from the group consisting of:

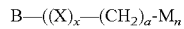

$$B\text{—}((X)_x\text{—}(CH_2)_a\text{-}M)_n \quad (VI),$$

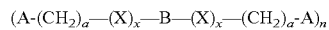

$$(A\text{-}(CH_2)_a\text{—}(X)_x\text{—}B\text{—}(X)_x\text{—}(CH_2)_a\text{-}A)_n \quad (IV),$$

$$(A\text{-}(CH_2)_a\text{—}(X)_x\text{—}B)_n \quad (V), \text{ and}$$

$$(B)_n\text{—}(X)_x\text{—}(CH_2)_a\text{-}A \quad (VII),$$

wherein,
A is a perfluoropolyether;
a is a positive integer;
X is either a covalent bond or a linking group;
x is a positive integer;
B is a polyalkylene oxide unit;
n is a positive integer greater than 1 and, in compounds comprising more than one A, B, X, a and x, each may be the same or different.

A preferred surfactant of the present invention has the formula (II):

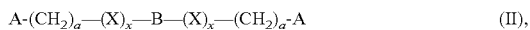

$$A\text{-}(CH_2)_a\text{—}(X)_x\text{—}B\text{—}(X)_x\text{—}(CH_2)_a\text{-}A \quad (II),$$

wherein each A, X, a and x may be the same or different.

It has been shown that surfactants of the present invention are suitable for use in forming stable emulsions, particularly emulsions comprising a discontinuous aqueous phase and a continuous oil phase wherein the oil phase comprises a fluorous oil. It has further been shown that emulsions stabilised by surfactants of the invention are suitable for use in various applications, including emulsion PCR. Surfactants of the invention have additionally been shown to be suitable for use in microfluidic devices.

Viewed from a further aspect the present invention provides a method for making a surfactant as hereinbefore defined, the method comprising: reacting a compound of the formula (VIII)

$$A\text{-}(CH_2)_a\text{—}Y \quad (VIII),$$

wherein A is a perfluoropolyether,
a is a positive integer, and
Y comprises a nucleophilic group, a leaving group, or an isocyanate group,
with a compound of the formula (XI)

$$Z\text{—}B\text{—}Z \quad (XI),$$

wherein B is a polyalkylene oxide, and
each Z comprises a nucleophilic group, a leaving group or an isocyanate group.

Viewed from a further aspect the present invention provides a composition comprising a surfactant as hereinbefore defined.

Viewed from a further aspect the present invention provides the use of a compound having a formula selected from the group consisting of (VI), (IV), (V), (VII) and (II) as hereinbefore defined as a surfactant.

Viewed from a further aspect the present invention provides the use of a surfactant as hereinbefore defined in the preparation of an emulsion.

Viewed from a further aspect the present invention provides an emulsion comprising a surfactant as hereinbefore defined.

Viewed from a further aspect the present invention provides an emulsion comprising:
a discontinuous aqueous phase;
a continuous oil phase; and
a surfactant as hereinbefore defined.

Viewed from a further aspect the present invention provides a method of preparing an emulsion as hereinbefore defined comprising:
(i) preparing an aqueous phase;
(ii) preparing an oil phase; and
(iii) mixing said aqueous phase, said oil phase and a surfactant as hereinbefore defined to form said emulsion.

Viewed from a further aspect the present invention provides a method comprising performing one or more chemical and/or biological reactions, and/or biological processes in the discontinuous aqueous phase of an emulsion as hereinbefore defined.

Viewed from a further aspect the present invention provides a method for sorting droplets in a microfluidic device, the method comprising:
(i) providing a stream of aqueous droplets in an emulsion as hereinbefore defined in a channel of the microfluidic device;
(ii) illuminating the stream from a first direction;
(iii) detecting light from analytes within the droplets in a second direction; and
(iv) sorting the droplets into one of a plurality of differentiated streams responsive to the detected light or a measurable signal.

Viewed from a further aspect the present invention provides a method of coalescing droplets in a microfluidic device, the method comprising:
(i) providing at least two aqueous droplets in an emulsion as hereinbefore defined in a channel of the microfluidic device; and
(ii) exposing the aqueous droplets to an electric field, thereby causing coalescence of the at least two aqueous droplets into a single droplet.

Viewed from a further aspect the present invention provides a method of introducing a fluid into a droplet in a microfluidic device, the method comprising:
(i) providing an aqueous droplet in an emulsion as hereinbefore defined in a channel of the microfluidic device; and
(ii) contacting the aqueous droplet with a stream of fluid, thereby introducing said fluid into the aqueous droplet.

Viewed from a further aspect the present invention provides a method of splitting droplets in a microfluidic device, the method comprising:
(i) providing a microfluidic device comprising a microfluidic junction, said microfluidic junction comprising a first microfluidic channel, a second microfluidic channel and a third microfluidic channel;
(ii) providing an aqueous droplet in an emulsion as hereinbefore defined in said first microfluidic channel; and
(iii) passing the aqueous droplet through the microfluidic junction, thereby splitting said aqueous droplet into at least a first daughter droplet and a second daughter droplet, the first daughter droplet in the second microfluidic channel and the second daughter droplet in the third microfluidic channel.

Viewed from a further aspect the present invention provides a method of extracting a molecule from a fluid, the method comprising:
(i) dissolving a surfactant as hereinbefore defined in carbon dioxide to form a carbon dioxide/surfactant mixture;
(ii) adding a fluid comprising the molecule to the carbon dioxide/surfactant mixture, thereby extracting the molecule from the fluid into the carbon dioxide.

Viewed from a further aspect the present invention provides the use of a surfactant as hereinbefore defined in a microfluidic channel or device.

Viewed from a further aspect the present invention provides the use of a surfactant as hereinbefore defined in a molecular isolation in larger fluidic devices, containers or vats.

Viewed from a further aspect the present invention provides the use of a surfactant as hereinbefore defined in an automated device with associated software that controls a microfluidic channel or device.

Viewed from a further aspect the present invention provides the use of an emulsion as hereinbefore defined in a microfluidic channel or device.

Viewed from a further aspect the present invention provides the use of an emulsion as hereinbefore defined in an automated device with associated software that controls a microfluidic channel or device.

Definitions

As used herein the term "perfluoropolyether" refers to a polyether compound wherein all of the hydrogen atoms have been replaced by fluorine atoms.

As used herein the term "polyalkylene oxide" refers to a compound or group comprising repeating units derived from one or more alkylene oxides (e.g. ethylene oxide and/or propylene oxide). A polyalkylene oxide may comprise one repeating unit derived from one or more alkylene oxides or may comprise more than one different repeating unit, each of which may be derived from one or more alkylene oxides. A polyalkylene oxide unit may comprise one or more polyalkylene oxide components, e.g. polyethylene oxide and/or polypropylene oxide components.

As used herein the term "alkyl" refers to any group comprising carbon and hydrogen. The group may be saturated, straight chained, branched or cyclic. Alkyl groups may be substituted or unsubstituted.

As used herein the term "linking group" refers to any group which acts to indirectly bond two or more components of a molecule together. When two components of a molecule are bonded together without a linking group the two parts of the molecule are directly bonded to one another, i.e. without any intervening atoms. When two components of a molecule are connected by a linking group there are intervening atoms between the two components.

As used herein the term "alkylene" refers to a bivalent group derived from an aliphatic (i.e. not aromatic) hydrocarbon that has had two hydrogen atoms removed The group may be substituted or unsubstituted. In substituted alkylenes one or more hydrogen atoms are replaced by a different group. $C_{1-8}$ alkylene refers to an alkylene group having 1 to 8 carbon atoms. $C_{1-5}$ refers to an alkylene group having 1 to 5 carbon atoms. $C_{1-3}$ refers to an alkylene group having 1 to 3 carbon atoms. An example of an alkylene group is ethylene which has the formula $C_2H_4$.

As used herein the term "arylene" refers to a bivalent group derived from an aromatic hydrocarbon that has had a hydrogen atom removed from two carbon atom. An example of an arylene group is phenylene ($C_6H_4$) which is derived from benzene. As used herein the term "heteroarylene" refers to an arylene group containing at least one heteroatom. Examples of "heteroatoms" include N, S or O. A heteroarylene is derived from an aromatic heterocycle that has had a hydrogen atom removed from two carbon atoms.

As used herein the term "nucleophilic group" refers to any atom or group that is capable of providing a pair of electrons to form a covalent bond.

As used herein the term "leaving group" refers to any atom or group capable of departing from a molecule following heterolytic cleavage of the covalent bond joining the leaving group to the rest of the molecule, taking with it the bonding electrons from the covalent bond.

As used herein the term "fluorous" refers to any group or substance which contains one or more fluorine atoms. Generally the group or substance contains multiple fluorine atoms. For example, a fluorous oil refers to any oil containing fluorine atoms, including partially fluorinated hydrocarbons, perfluorocarbons, hydrofluoroethers and mixtures thereof.

As used herein the term "hydrocarbon" refers to any compound comprising carbon and hydrogen. One or more of the hydrogen atoms may be replaced by a different atom or group. For example, a partially fluorinated hydrocarbon is a hydrocarbon wherein some, but not all, of the hydrogen atoms have been replaced by fluorine atoms. A perfluorocarbon is a hydrocarbon wherein every hydrogen atom has been replaced by a fluorine atom.

DESCRIPTION OF INVENTION

The present invention relates to a surfactant comprising a perfluoropolyether and a polyalkylene oxide, wherein the perfluoropolyether is linked to the polyalkylene oxide via an alkyl group and optionally a linking group.

The surfactant of the present invention has a formula selected from the group consisting of:

B—((X)$_x$—(CH$_2$)$_a$-A)$_n$   (VI),

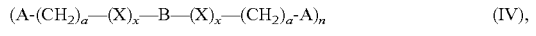
(A-(CH$_2$)$_a$—(X)$_x$—B—(X)$_x$—(CH$_2$)$_a$-A)$_n$   (IV),

(A-(CH$_2$)$_a$—(X)$_x$—B)$_n$   (V), and

(B)$_n$—(X)$_x$—(CH$_2$)$_a$-A   (VII), wherein,
A is a perfluoropolyether;
a is a positive integer;
X is either a covalent bond or a linking group;
x is a positive integer;
B is a polyalkylene oxide unit;
n is a positive integer greater than 1 and, in compounds comprising more than one A, B, X, a and x, each may be the same or different.

Preferably the surfactant of the present invention has the formula (II):

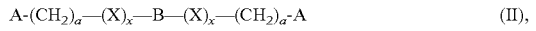
A-(CH$_2$)$_a$—(X)$_x$—B—(X)$_x$—(CH$_2$)$_a$-A   (II), wherein each A, X, a and x may be the same or different.

The surfactants of the present invention comprise a unit of the formula (I):

A-(CH$_2$)$_a$—(X)$_x$—B—   (I), wherein A is a perfluoropolyether. Each surfactant of the present invention comprises at least one perfluoropolyether (A) component. The perfluoropolyether component acts as a fluorophilic tail, and is soluble in an oil phase, e.g. the continuous oil phase of an emulsion, particularly wherein the oil phase comprises a fluorous oil, e.g. a fluorous oil phase.

In surfactants of the present invention, each A preferably comprises a repeat unit of the formula —[CF(CF$_3$)CF$_2$O]$_b$—, wherein b is a positive integer. More preferably each A comprises a unit of the formula —[CF$_2$CF$_2$O]$_c$—[CF(CF$_3$)CF$_2$O]$_b$—, wherein b and c are each 0 or a positive integer, with the proviso that b and c are not both 0. c is preferably 0 or an integer from 1 to 100, e.g. an integer from 5 to 50. In preferred surfactants c is 0. In particularly preferred surfactants each A consists of the formula CF$_3$CF$_2$CF$_2$O—[CF(CF$_3$)CF$_2$O]$_b$—CF(CF$_3$)—, wherein b is a positive integer. In the surfactants of the present invention in the above formulae b is preferably an integer from 1 to 100 (e.g. 1 to 50), more preferably an integer from 5 to 50 and particularly preferably an integer from 10 to 25. In preferred surfactants of the present invention each A has a weight average molecular weight of 166 to 16,600 Da, more preferably 800 to 9,000 Da and yet more preferably 1,500 to 6,000 Da.

In the surfactants of the present invention, each a is a positive integer. In the surfactants of the invention there is therefore an alkyl group between the perfluoropolyether component and the polyalkylene oxide component. The alkyl group acts as a spacer and advantageously makes the surfactant more stable, e.g. more resistant to hydrolysis. Preferably each a is an integer from 1 to 5. More preferably each a is 1.

In one group of surfactants of the present invention, at least one X is a covalent bond. When X is a covalent bond the alkyl group is directly bonded to both the perfluoropolyether component and the polyalkylene oxide component of the surfactant.

In another group of surfactants of the present invention, at least one X is a linking group. When X is a linking group the alkyl group is directly bonded to the perfluoropolyether component but is not directly bonded to the polyalkylene oxide component of the surfactant. Preferably at least one X is a linking group of the formula -D-(E)$_h$-(G)$_d$- or -(G)$_d$-(E)$_h$-D-, wherein D is selected from NH, NMe, C(O), CO$_2$, O or SO$_g$ wherein g is 0, 1 or 2, E is selected from alkylene, optionally substituted arylene or optionally substituted heteroarylene, h is 0 or 1, G is selected from C(O)NH, CO$_2$, NH, NMe, O, C(O), S or SO$_2$NH, and d is 0 or 1. More preferably at least one X is a linking group of the formula -D-(E)$_h$-(G)$_d$- or -(G)$_d$-(E)$_h$-D-, wherein D is selected from NH, C(O), CO$_2$, O or SO$_g$ wherein g is 0, 1 or 2, E is selected from alkylene, optionally substituted arylene or optionally substituted heteroarylene, h is 0 or 1, G is selected from C(O)NH, CO$_2$, NH, O, C(O), S or SO$_2$NH, and d is 0 or 1.

Preferred alkylenes are C$_{1-8}$ alkylene, more preferably C$_{1-5}$ alkylene (e.g. methylene, ethylene, propylene or butylene), and still more preferably C$_{1-3}$ alkylene, e.g. methylene, ethylene or propylene. Preferred optionally substituted arylenes are optionally substituted phenylenes and optionally substituted naphthylenes, more preferably optionally substituted phenylenes. Preferred optionally substituted heteroarylenes are derived from furan, pyrrole, pyridine thiophene, benzofuran, indole, imidazole and benzimidazole.

Suitable optional substituents for the optionally substituted arylene and optionally substituted heteroarylene include groups such as OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, CO$_2$H, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list.

In some preferred surfactants of the invention, E is phenylene. In others, E is an optionally substituted arylene group.

When E is an optionally substituted arylene or heteroarylene group the optional substituents are preferably selected from —$CH_3$, —$CH_2CH_3$, —$CH(CH_3)_2$, —$OCH_3$, —$OCH_2CH_3$, —$OCH(CH_3)_2$, —$SCH_3$, —$SCH_2CH_3$, —$SCH(CH_3)_2$ and —$N(CH_3)_2$.

In surfactants of the invention wherein at least one X is a linking group, at least one X may comprise or consist of an amide, thioester, ester, carbonate, carbamate, ether, thioether, urea, sulfonyl or sulphonamide linkage, preferably a thioester, carbonate, carbamate, ether, thioether, urea, sulfonyl or sulphonamide linkage. More preferably at least one X comprises, e.g. consists of, a carbamate, ether, urea, sulfonyl or sulphonamide linkage, even more preferably an ether, urea or carbamate linkage, yet more preferably an ether or carbamate linkage. Still more preferably at least one X consists of an ether or carbamate linkage.

In some preferred surfactants of the present invention, at least one X is a linking group selected from —C(O)NH—, —C(O)NMe-, —NHC(O)—, —NMeC(O)—, —C(O)S—, —SC(O)—, —C(O)O—, —OC(O)—, —OC(O)O—, —OC(O)NH—, —OC(O)NMe-, —O—, —S—, —NHC(O)NH—, —NMeC(O)NH—, —NHC(O)NMe-, —NHC(O)O—, —NMeC(O)O—, —$SO_2$NH—, —NH$SO_2$—, —NH$SO_2$—$C_6H_4$—O— and —O—$C_6H_4$—$SO_2$NH—. More preferably at least one X is a linking group selected from —C(O)NH—, —C(O)NMe-, —NHC(O)—, —NMeC(O)—, —C(O)S—, —SC(O)—, —OC(O)O—, —OC(O)NH—, —OC(O)NMe-, —O—, —S—, —NHC(O)NH—, NMeC(O)NH—, —NHC(O)NMe-, —NHC(O)O—, —NMeC(O)O—, —$SO_2$NH—, —NH$SO_2$—, —NH$SO_2$—$C_6H_4$—O— and —O—$C_6H_4$—$SO_2$NH—. Still more preferably at least one X is a linking group selected from —C(O)NH—, —C(O)NMe-, —NHC(O)—, —NMeC(O)—, —OC(O)NH—, —OC(O)NMe-, —O—, —NHC(O)NH—, NMeC(O)NH—, —NHC(O)NMe-, —NHC(O)O—, —NMeC(O)O—, —$SO_2$NH—, —NH$SO_2$—, —NH$SO_2$—$C_6H_4$—O— and —O—$C_6H_4$—$SO_2$NH—. Yet more preferably at least one X is a linking group selected from —OC(O)NH—, —OC(O)NMe-, —O—, —NHC(O)NH—, —NMeC(O)NH—, NHC(O)NMe-, —NHC(O)O—, —NMeC(O)O—, —$SO_2$NH—, —NH$SO_2$—, —NH$SO_2$—$C_6H_4$—O— and —O—$C_6H_4$—$SO_2$NH—, preferably from —O—, —OC(O)NH—, —NHC(O)O—, —NHC(O)NH—, —NMeC(O)O— or NMeC(O)NH—, and most preferably from —O—, —OC(O)NH—, —NHC(O)O— or —NHC(O)NH—.

In certain preferred surfactants of the present invention, at least one X is a linking group selected from —C(O)NH—, —NHC(O)—, —C(O)S—, —SC(O)—, —C(O)O—, —OC(O)—, OC(O)O—, —OC(O)NH—, —O—, —S—, —NHC(O)NH—, —NHC(O)O—, —$SO_2$NH—, —NH$SO_2$—, —NH$SO_2$—$C_6H_4$—O— and —O—$C_6H_4$—$SO_2$NH—. More preferably at least one X is a linking group selected from —C(O)NH—, —NHC(O)—, —C(O)S—, —SC(O)—, —OC(O)O—, —OC(O)NH—, —O—, —S—, —NHC(O)NH—, —NHC(O)O—, —$SO_2$NH—, —NH$SO_2$—, —NH$SO_2$—$C_6H_4$—O— and —O—$C_6H_4$—$SO_2$NH—. Still more preferably at least one X is a linking group selected from —C(O)NH—, —NHC(O)—, —OC(O)NH—, —O—, —NHC(O)NH—, —NHC(O)O—, —$SO_2$NH—, —NH$SO_2$—, —NH$SO_2$—$C_6H_4$—O— and —O—$C_6H_4$—$SO_2$NH—. Yet more preferably at least one X is a linking group selected from —OC(O)NH—, —O—, —NHC(O)NH—, —NHC(O)O—, —$SO_2$NH—, —NH$SO_2$—, —NH$SO_2$—$C_6H_4$—O— and —O—$C_6H_4$—$SO_2$NH—, preferably from —O—, —OC(O)NH— or —NHC(O)O—, e.g. —O— or —OC(O)NH—.

In the surfactants of the present invention, each x is a positive integer. Preferably each x is 1, 2 or 3. More preferably each x is 1. When x is greater than 1, each X may independently be a covalent bond or a linking group as defined above. Each X may be different. Alternatively, each X may be the same.

In the surfactants of the present invention, each B is a polyalkylene oxide unit. The polyalkylene oxide unit acts as a hydrophilic headgroup, and is soluble in an aqueous phase, e.g. the discontinuous aqueous phase of an emulsion. Preferably, each B comprises polyethylene oxide and/or polypropylene oxide. Preferably, each B comprises a polyethylene oxide unit and/or a polypropylene oxide unit. Optionally the polyalkylene oxide unit is connected to one or more —($CH_2$)— groups.

In preferred surfactants of the present invention each B comprises a unit of the formula —[$CH_2CH_2O$]$_e$—, wherein e is a positive integer. In further preferred surfactants, each B comprises a unit of the formula —[$CH(CH_3)CH_2O$]$_f$—, wherein f is a positive integer. In one group of preferred surfactants, each B comprises a unit of the formula —[$CH_2CH_2O$]$_e$— and a unit of the formula —[$CH(CH_3)CH_2O$]$_f$—, wherein e and f are each independently a positive integer. In another group of preferred surfactants, each B comprises a unit of the formula —[$CH_2CH_2O$]$_e$— wherein e is a positive integer or a unit of the formula —[$CH(CH_3)CH_2O$]$_f$— wherein f is a positive integer, preferably a unit of the formula —[$CH_2CH_2O$]$_e$— wherein e is a positive integer. Optionally each B further comprises one or more —($CH_2$)— groups.

In some preferred surfactants of the present invention, each B consists of a unit of the formula —[$CH_2HCH_2CH_2O$]$_e$—[$CH_2$]$_r$—, wherein e is a positive integer and r and r' are each independently 0, 1, 2, 3, 4 or 5. Preferably r and r' are each independently 0, 1, 2 or 3. In some preferred surfactants of the invention both r and r' are 0, i.e. B consists of the formula —[$CH_2CH_2O$]$_e$—. In other preferred surfactants r is 0 and r' is 2, i.e. B consists of the formula —[$CH_2CH_2O$]$_e$—$CH_2CH_2$—. In other preferred surfactants r is 1 and r' is 3, i.e. B consists of the formula $CH_2$—[$CH_2CH_2O$]$_e$—$CH_2CH_2CH_2$—. Preferably B consists of a unit of the formula —[$CH_2CH_2O$]$_e$—, wherein e is a positive integer. In other preferred surfactants of the invention, each B consists of the formula —[$CH(CH_3)CH_2O$]$_{f'}$—[$CH_2CH_2O$]$_e$—[$CH_2CH(CH_3)O$]$_{f'}$—$CH_2CH(CH_3)$—, wherein e, f and f' are each independently a positive integer.

Preferably e is an integer from 1 to 100, more preferably 5 to 50, and yet more preferably 10 to 30. Preferably f is an integer from 1 to 50, more preferably 1 to 10, and yet more preferably 1 to 5. Preferably f' is an integer from 1 to 50, more preferably 1 to 10, and yet more preferably 1 to 5. f and f' may be the same or they may be different.

In preferred surfactants of the present invention each B has a weight average molecular weight of 50 to 5,000 Da, more preferably 200 to 2,500 Da and yet more preferably 400 to 1,500 Da.

In the surfactants of the present invention, n is a positive integer greater than 1. n is preferably 2 to 50. Preferred surfactants of the present invention have the formula (VI). Particularly preferred surfactants of the present invention are surfactants of formula (VI), wherein n is 2. Surfactants of formula (VI) wherein n is 2 are represented by the formula (II):

$$A\text{-}(CH_2)_a\text{—}(X)_x\text{—}B\text{—}(X)_x\text{—}(CH_2)_a\text{-}A \quad \text{(II)}.$$

Thus most preferably the surfactants of the present invention have the formula (II):

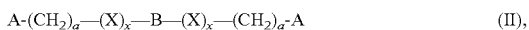

wherein each A, X, a and x may be the same or different. Previous definitions and previous preferred definitions apply to each of these formulae, i.e. definitions and preferred definitions of each of A, a, X, x, and B are as set out above in relation to formulae (VI), (IV), (V) and (VII). Particularly preferred surfactants are surfactants having the formula (II), wherein at least one X is a linking group.

Preferred surfactants of the present invention have a weight average molecular weight of 500 to 20,000 Da, more preferably 2,000 to 15,000 Da and yet more preferably 3,000 to 10,000 Da.

Preferred surfactants of the present invention are selected from the group consisting of:

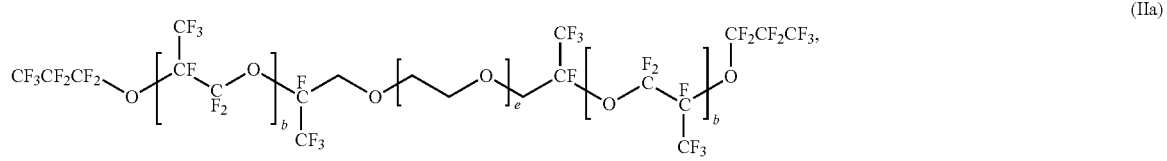

(IIa)

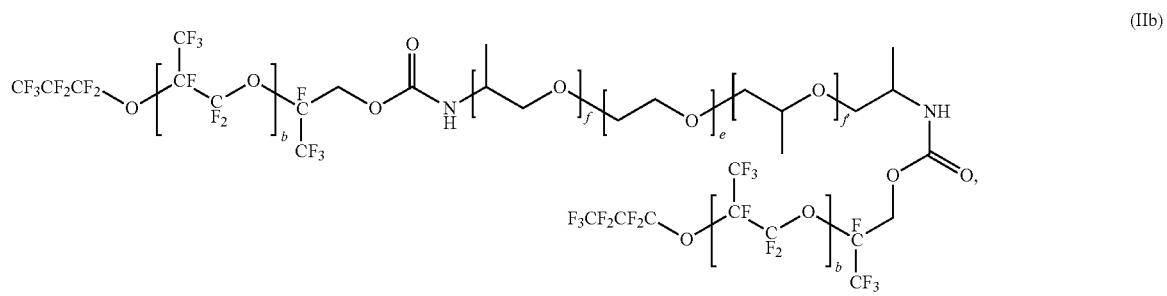

(IIb)

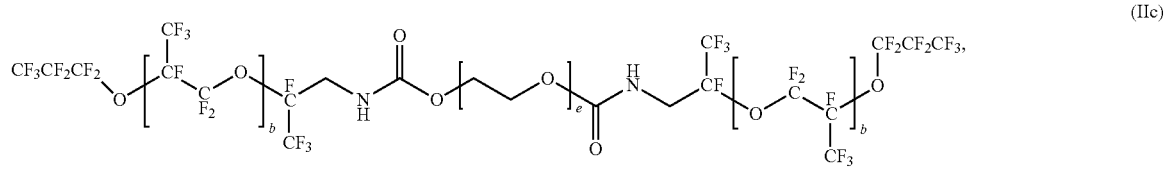

(IIc)

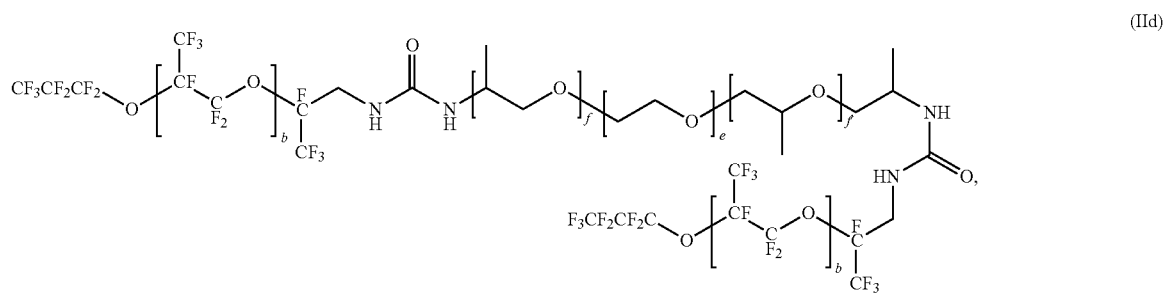

(IId)

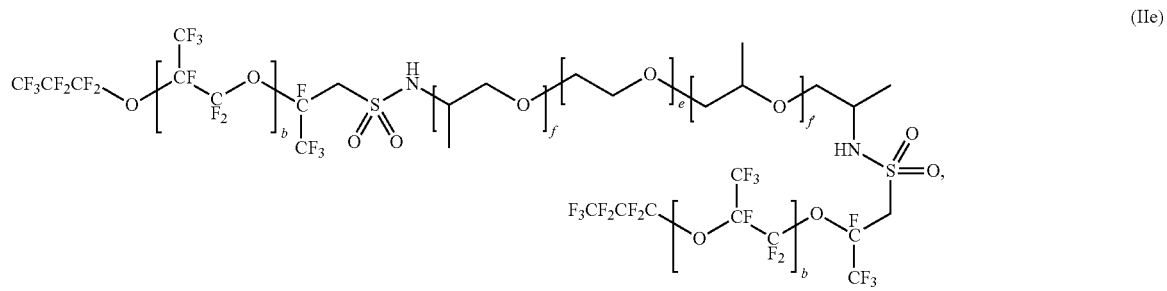

(IIe)

-continued
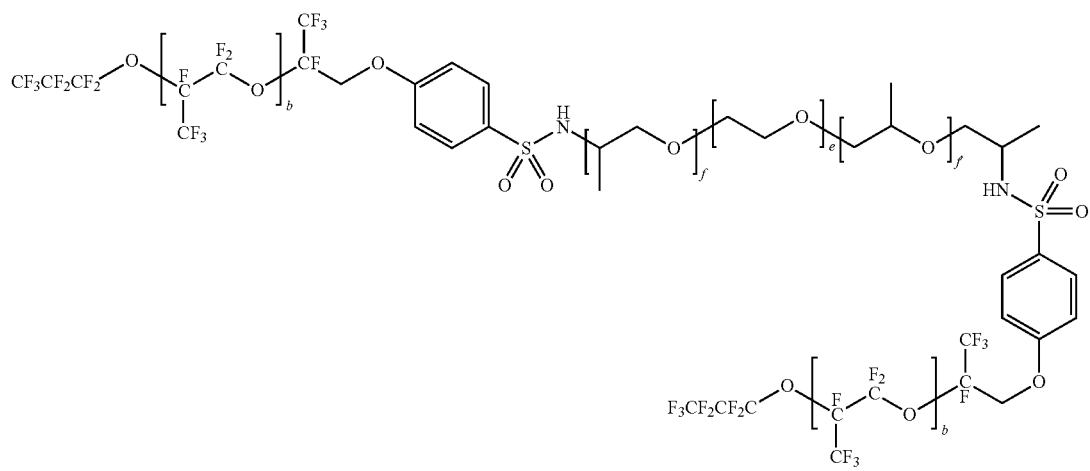
(IIf)
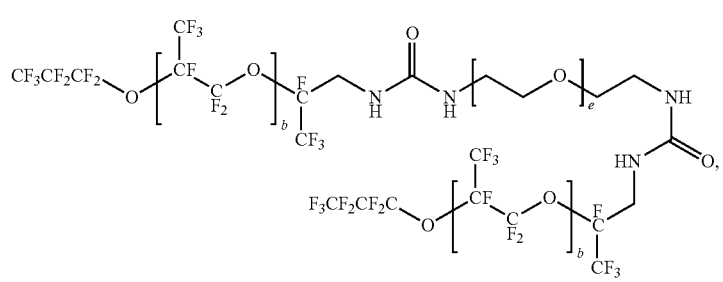
(IIg)
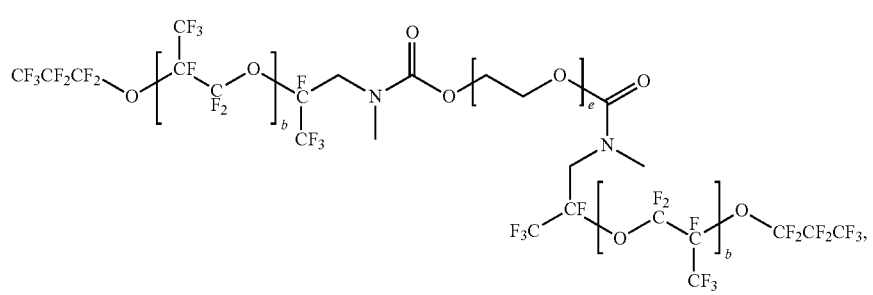
(IIh)
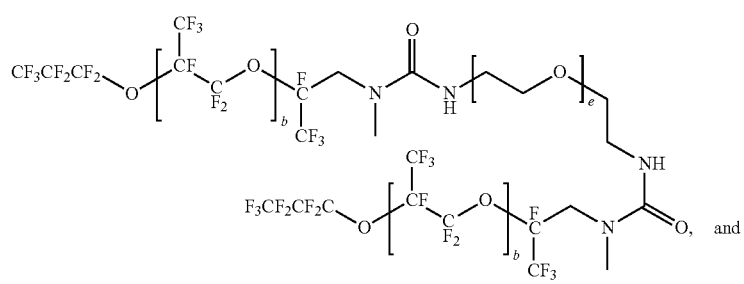
(IIi)
and
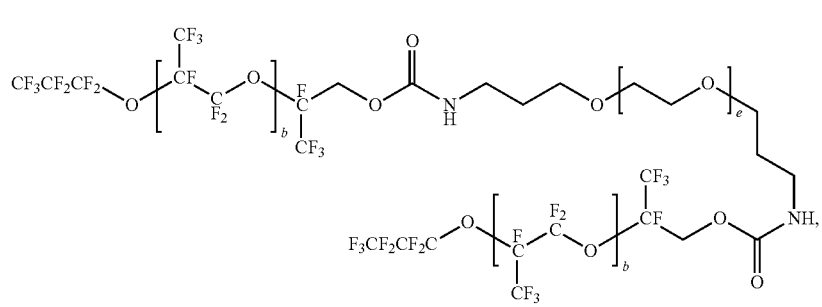
(IIj)

wherein each b, e, f and f' are each independently a positive integer.
Especially preferred surfactants of the present invention are selected from the group consisting of:
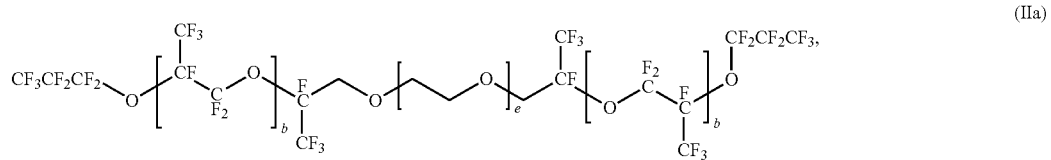
(IIa)
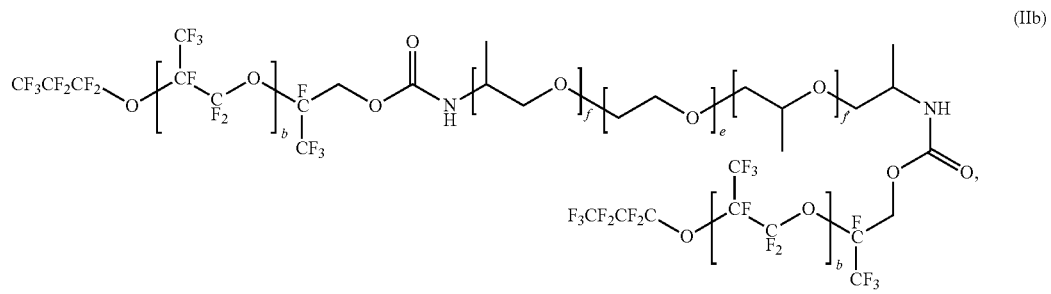
(IIb)
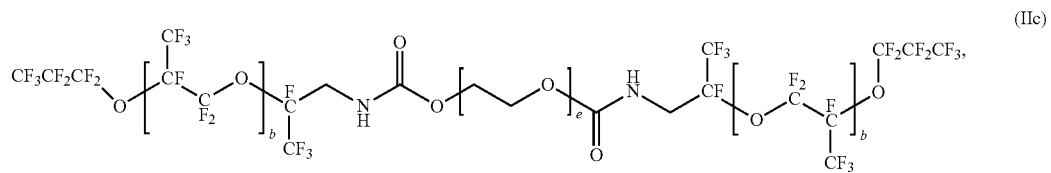
(IIc)
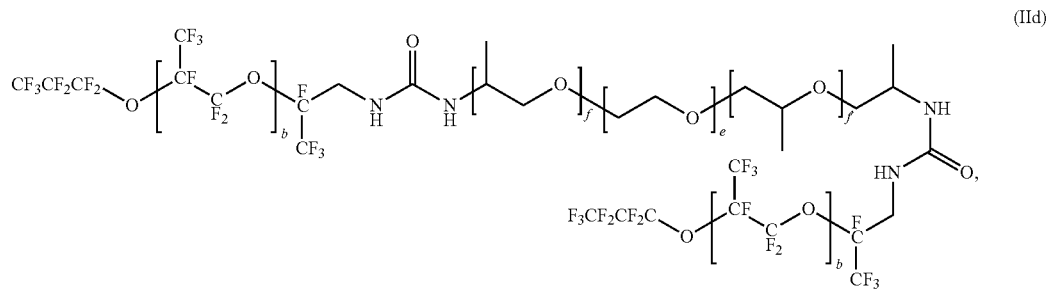
(IId)
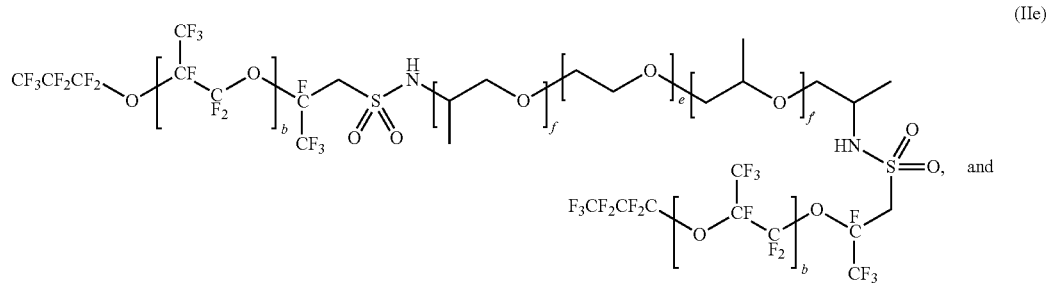
(IIe)
and

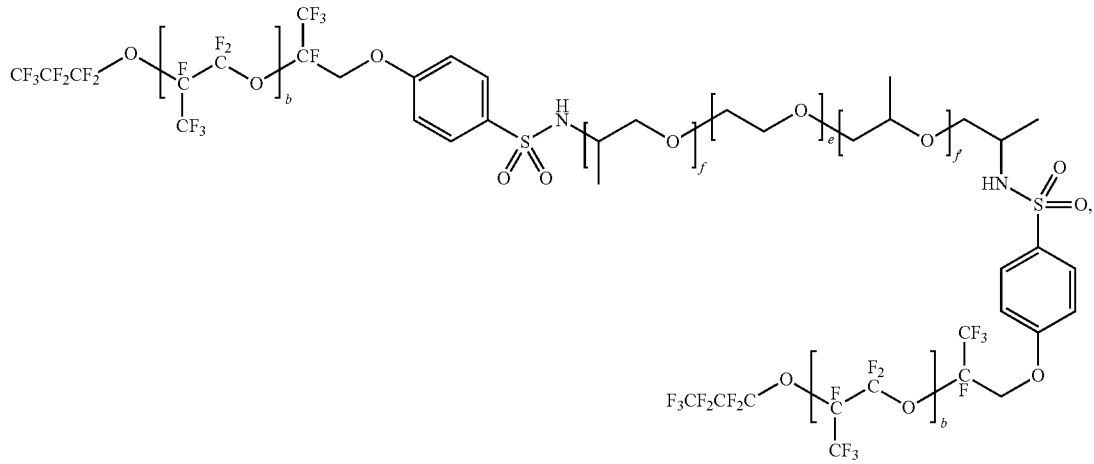
(IIf)
wherein each b, e, f and f' are each independently a positive integer.
Preferred surfactants of the present invention are selected from the group consisting of:
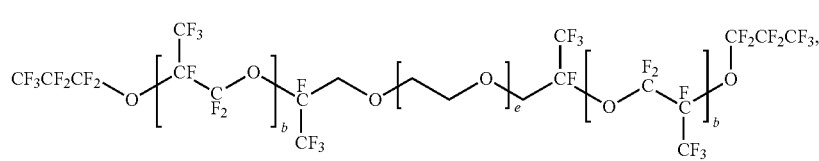
(IIa)
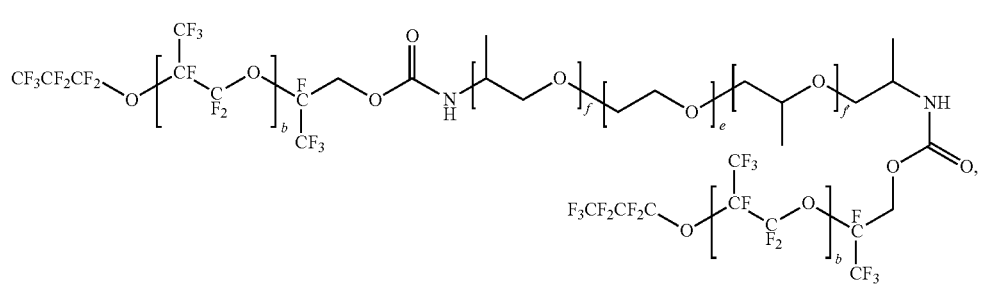
(IIb)
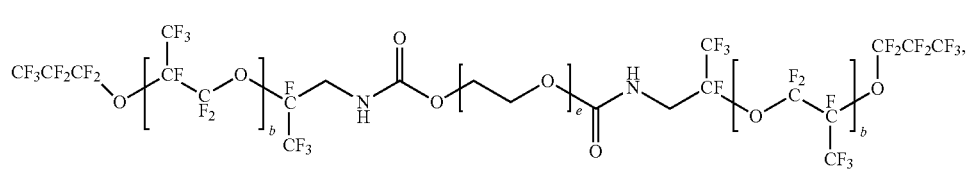
(IIc)
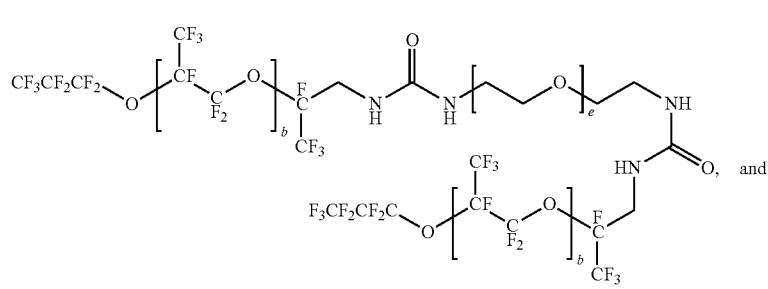
(IIg)
and -continued

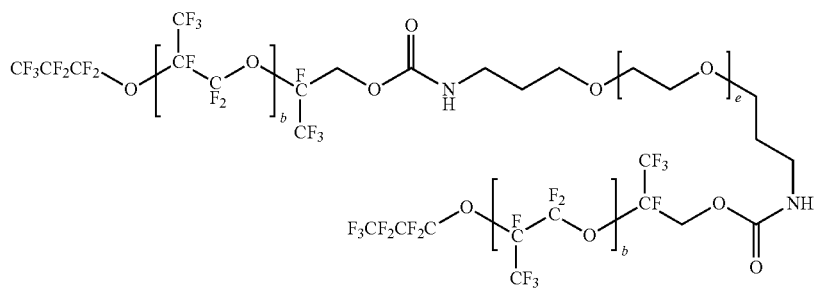
(IIj)

wherein each b, e, f and f' are each independently a positive integer.

Particularly preferred surfactants of the present invention are selected from the group consisting of:

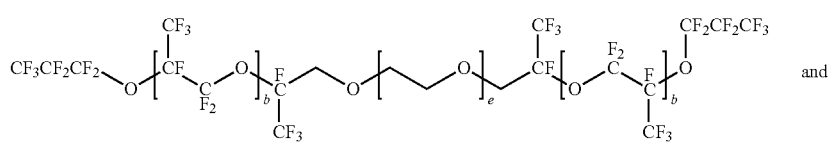
(IIa)

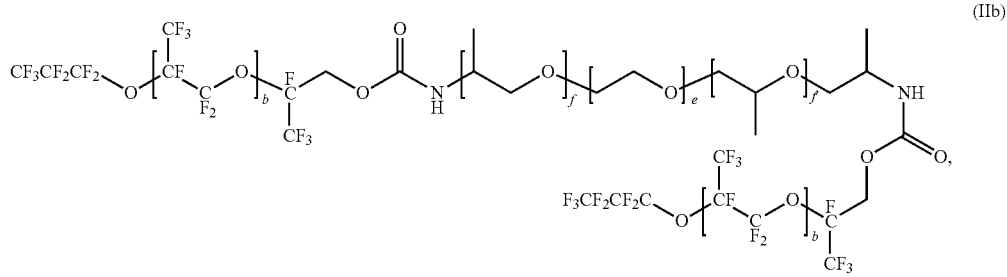
(IIb)

wherein each b, e, f and f' are each independently a positive integer.

In the surfactants of the formula (IIa) to (IIj), preferred values for each b and each of e, f and f' are as set out above in relation to formulae (VI), (IV), (V) and (VII). Each b maybe the same or they may be different. f and f' may be the same or they may be different.

The present invention also relates to a method for making a surfactant as hereinbefore defined. The method comprises reacting a compound of the formula (VIII)

A-(CH$_2$)$_a$—Y (VIII), wherein A is a perfluoropolyether,
a is a positive integer, and
Y comprises a nucleophilic group, a leaving group, or an isocyanate group, with a compound comprising a unit of the formula (IX):

Z—B— (IX), wherein B is a polyalkylene oxide, and
Z comprises a nucleophilic group, a leaving group or an isocyanate group.

Preferably the method comprises reacting a compound of the formula (VIII)

A-(CH$_2$)$_a$—Y (VIII), wherein A is a perfluoropolyether,
a is a positive integer, and
Y comprises a nucleophilic group, a leaving group, or an isocyanate group, with a compound of the formula (XI)

Z—B—Z (XI), wherein B is a polyalkylene oxide, and
each Z comprises a nucleophilic group, a leaving group or an isocyanate group.

In some preferred methods of the invention definitions and preferred definitions of each of A, a and B are as set out above in relation to formulae (VI), (IV), (V) and (VII). In further preferred methods of the invention definitions and preferred definitions of each of A and a are as set out above in relation to formulae (VI), (IV), (V) and (VII) and B consists of the formula —[CH$_2$]$_r$—[CH$_2$CH$_2$O]$_e$—[CH$_2$]$_{r'}$— or —[CH(CH$_3$)CH$_2$O]$_f$—[CH$_2$CH$_2$O]$_e$—[CH$_2$CH(CH$_3$)O]$_{f'}$—CH$_2$CH(CH$_3$)—, wherein e, f and f' are each independently a positive integer and wherein r and r' are each independently 0, 1, 2, 3, 4 or 5. Preferably r and r' are each independently 0, 1, 2 or 3. Preferred values for each of e, f and f' are as set out above in relation to formulae (VI), (IV), (V) and (VII). f and f' may be the same or they may be different. In certain preferred methods wherein B consists of the formula —[CH$_2$]$_r$—[CH$_2$CH$_2$O]$_e$—[CH$_2$]$_{r'}$—, r is 0 and r' is 2, i.e. B consists of the formula —[CH$_2$CH$_2$O]$_e$—CH$_2$CH$_2$—. In other preferred methods wherein B consists of the formula —[CH$_2$]$_r$—[CH$_2$CH$_2$O]$_e$—[CH$_2$]$_{r'}$—, r is 1 and r' is 3, i.e. B consists of the formula —CH$_2$—[CH$_2$CH$_2$O]$_e$—CH$_2$CH$_2$CH$_2$—. In further preferred methods wherein B consists of the formula —[CH$_2$CH$_2$O]$_r$—[CH$_2$CH$_2$O]$_e$—[CH$_2$]$_{r'}$—, both r and r' are 0, i.e. B consists of the formula —[CH$_2$CH$_2$O]$_e$—. More preferably B consists of the formula —[CH$_2$CH$_2$O]$_e$—CH$_2$CH$_2$— or —[CH(CH$_3$)CH$_2$O]$_f$—[CH$_2$CH$_2$O]$_e$—[CH$_2$CH(CH$_3$)O]$_{f'}$—CH$_2$CH(CH$_3$)—, wherein e, f and f' are each independently a positive integer.

Preferably Z comprises a nucleophilic group or a leaving group. Preferably Y comprises a nucleophilic group or a leaving group. When Y comprises a nucleophilic group, each Z preferably comprises a leaving group or an isocyanate group, more preferably a leaving group. When Z comprises a nucleophilic group, Y preferably comprises a leaving group or an isocyanate group, more preferably a leaving group.

The reaction of a compound of formula (VIII) with a compound comprising a unit of the formula (IX) (e.g. a compound of formula (XI)) leads to the formation of a surfactant as hereinbefore defined, i.e. a surfactant having a formula selected from the group consisting of (VI), (IV), (V), and (VII).

In preferred methods of the invention the reaction of a compound of formula (VIII) with a compound comprising a unit of the formula (IX) involves the chemical reaction of the Y component of a compound of formula (VIII) with the Z component of a compound comprising a unit of the formula (IX). Preferably, this leads to the formation of a linking group or a covalent bond in the resulting surfactant, e.g. the formation of the X component in a surfactant having a formula selected from the group consisting of (VI), (IV), (V), and (VII).

In preferred methods of the invention the reaction of a compound of formula (VIII) with a compound of formula (XI) involves the chemical reaction of the Y component of a compound of formula (VIII) with the Z component of a compound of formula (XI). Preferably, this leads to the formation of a linking group or a covalent bond in the resulting surfactant, e.g. the formation of the X component in a surfactant having a formula selected from the group consisting of (VI), (IV), (V), and (VII).

The surfactant made by the method of the invention is a surfactant having the formula (VI), (IV), (V) or (VII) as hereinbefore defined. More preferably, the surfactant made by the method is a surfactant having the formula (VI) as hereinbefore defined. Most preferably, the surfactant made by the method of the invention is a surfactant having the formula (II) as hereinbefore defined (i.e. a surfactant having the formula (VI) wherein n is 2).

A surfactant having the formula (II) may be made by the combination of two molecules of a compound of the formula (VIII) with one molecule of a compound comprising a unit of the formula (IX) (e.g. one molecule of a compound of the formula (XI)). A surfactant having the formula (IV) may be made by the combination of n molecules of a compound comprising a unit of the formula (IX) (e.g. n molecules of a compound of the formula (XI)) with 2n molecules of a compound of the formula (VIII). A surfactant having the formula (V) may be made by the combination of n molecules of a compound comprising a unit of the formula (IX) with n molecules of a compound of the formula (VIII). A surfactant having the formula (VI) may be made by the combination of one molecule of a compound comprising a unit of the formula (IX) with n molecules of a compound of the formula (VIII). A surfactant having the formula (VII) may be made by the combination of n molecules of a compound comprising a unit of the formula (IX) with one molecule of a compound of the formula (VIII).

In the method of the present invention Y comprises a nucleophilic group, a leaving group, or an isocyanate group. Preferably Y is selected from NH$_2$, NHMe, OH, SH, NCO, Cl, Br, I, OMe, OEt, OTs, OMs, OTf, OC$_6$H$_4$NO$_2$, NHC(O)L, C(O)L, OC(O)L, SO$_2$L and OC$_6$H$_4$SO$_2$L, wherein L is a suitable leaving group preferably selected from Cl, Br, I, OMe, OEt, OH, OTs, OMs, OTf and OC$_6$H$_4$NO$_2$. More preferably Y is selected from NH$_2$, NHMe, OH, SH, NCO, C(O)L (e.g. C(O)Cl or C(O)OMe), OC(O)OL (e.g. OC(O)OC$_6$H$_4$NO$_2$), SO$_2$L (e.g. SO$_2$Cl) and OC$_6$H$_4$SO$_2$L (e.g. OC$_6$H$_4$SO$_2$Cl), still more preferably from NH$_2$, NHMe, OH, NCO, OC(O)OC$_6$H$_4$NO$_2$, SO$_2$Cl and OC$_6$H$_4$SO$_2$Cl. In particularly preferred methods Y is selected from OH, NH$_2$, NHMe and OC(O)OC$_6$H$_4$NO$_2$.

In a preferred method of the present invention Y is selected from NH$_2$, OH, SH, NCO, Cl, Br, I, OMe, OEt, OTs, OMs, OTf, OC$_6$H$_4$NO$_2$, NHC(O)L, C(O)L, OC(O)L, SO$_2$L and OC$_6$H$_4$SO$_2$L, wherein L is a suitable leaving group preferably selected from Cl, Br, I, OMe, OEt, OH, OTs, OMs, OTf and OC$_6$H$_4$NO$_2$. More preferably Y is selected from NH$_2$, OH, SH, NCO, C(O)L (e.g. C(O)Cl or C(O)OMe), OC(O)OL (e.g. OC(O)OC$_6$H$_4$NO$_2$), SO$_2$L (e.g. SO$_2$Cl) and OC$_6$H$_4$SO$_2$L (e.g. OC$_6$H$_4$SO$_2$Cl), still more preferably from NH$_2$, OH, NCO, OC(O)OC$_6$H$_4$NO$_2$, SO$_2$Cl and OC$_6$H$_4$SO$_2$Cl. In particularly preferred methods Y is selected from OH and OC(O)OC$_6$H$_4$NO$_2$.

In the method of the present invention Z comprises a nucleophilic group, a leaving group, or an isocyanate group. Preferably Z is selected from NH$_2$, OH, SH, NCO, Cl, Br, I, OMe, OEt, OH, OTs, OMs, OTf, OC$_6$H$_4$NO$_2$, NHC(O)L, C(O)L, OC(O)L, SO$_2$L and OC$_6$H$_4$SO$_2$L, wherein L is a suitable leaving group preferably selected from Cl, Br, I, OMe, OEt, OH, OTs, OMs, OTf and OC$_6$H$_4$NO$_2$. More preferably Z is selected from NH$_2$, OTs, OMs, OTf, NCO and OC(O)L (e.g. OC(O)OC$_6$H$_4$NO$_2$), still more preferably from NH$_2$, NCO, OTs and OC(O)L (e.g. OC(O)OC$_6$H$_4$NO$_2$). In particularly preferred methods Z is selected from NCO, OTs, OC(O)OC$_6$H$_4$NO$_2$ and NH$_2$.

In a preferred method of the present invention Z is selected from NH$_2$, OH, SH, NCO, Cl, Br, I, OMe, OEt, OH, OTs, OMs, OTf, OC$_6$H$_4$NO$_2$, NHC(O)L, C(O)L, OC(O)L, SO$_2$L and OC$_6$H$_4$SO$_2$L, wherein L is a suitable leaving group preferably selected from Cl, Br, I, OMe, OEt, OH, OTs, OMs, OTf and OC$_6$H$_4$NO$_2$. More preferably Z is selected from NH$_2$, OTs, OMs, OTf and OC(O)L (e.g. OC(O)OC$_6$H$_4$NO$_2$), still more preferably from NH$_2$, OTs and OC(O)L (e.g. OC(O)OC$_6$H$_4$NO$_2$). In particularly preferred methods Z is selected from OTs and NH$_2$.

In some preferred methods of the present invention the compound of formula (VIII) is selected from the group consisting of CF$_3$CF$_2$CF$_2$O—[CF(CF$_3$)CF$_2$O]$_b$—CF(CF$_3$)—C(O)OH, CF$_3$CF$_2$CF$_2$O—[CF(CF$_3$)CF$_2$O]$_b$—CF(CF$_3$)—C(O)NH$_2$, CF$_3$CF$_2$CF$_2$O—[CF(CF$_3$)CF$_2$O]$_b$—CF(CF$_3$)—C(O)Cl, CF$_3$CF$_2$CF$_2$O—[CF(CF$_3$)CF$_2$O]$_b$—CF(CF$_3$)—C(O)OMe, CF$_3$CF$_2$CF$_2$O—[CF(CF$_3$)CF$_2$O]$_b$—CF(CF$_3$)—CH$_2$OC$_6$H$_4$SO$_2$Cl, CF$_3$CF$_2$CF$_2$O—[CF(CF$_3$)CF$_2$O]$_b$—CF(CF$_3$)—CH$_2$SO$_2$Cl, CF$_3$CF$_2$CF$_2$O—[CF(CF$_3$)CF$_2$O]$_b$—CF(CF$_3$)—CH$_2$OC(O)OC$_6$H$_4$NO$_2$, CF$_3$CF$_2$CF$_2$O—[CF(CF$_3$)CF$_2$O]$_b$—CF(CF$_3$)—CH$_2$OH, CF$_3$CF$_2$CF$_2$O—[CF(CF$_3$)CF$_2$O]$_b$—CF(CF$_3$)—CH$_2$OPh, CF$_3$CF$_2$CF$_2$O—[CF(CF$_3$)CF$_2$O]$_b$—CF(CF$_3$)—CH$_2$NCO, CF$_3$CF$_2$CF$_2$O—[CF(CF$_3$)CF$_2$O]$_b$—CF(CF$_3$)—CH$_2$NH$_2$ and —CF$_3$CF$_2$CF$_2$O—[CF(CF$_3$)CF$_2$O]$_b$—CF(CF$_3$)—CH$_2$NHMe, wherein definitions and preferred definitions of b are as described above in relation to formulae (VI), (IV), (V) and (VII).

More preferably the compound of formula (VIII) is selected from the group consisting of CF$_3$CF$_2$CF$_2$O—[CF(CF$_3$)CF$_2$O]$_b$—CF(CF$_3$)—CH$_2$OC$_6$H$_4$SO$_2$Cl, CF$_3$CF$_2$CF$_2$O—[CF(CF$_3$)CF$_2$O]$_b$—CF(CF$_3$)—CH$_2$SO$_2$Cl, $CF_3CF_2CF_2O$—$[CF(CF_3)CF_2O]_b$—$CF(CF_3)$—$CH_2OC(O)$ $OC_6H_4NO_2$, $CF_3CF_2CF_2O$—$[CF(CF_3)CF_2O]_b$—$CF(CF_3)$—$CH_2OH$, $CF_3CF_2CF_2O$—$[CF(CF_3)CF_2O]_b$—$CF(CF_3)$—$CH_2NCO$, $CF_3CF_2CF_2O$—$[CF(CF_3)CF_2O]_b$—$CF(CF_3)$—$CH_2NH_2$ and —$CF_3CF_2CF_2O$—$[CF(CF_3)CF_2O]_b$—$CF(CF_3)$—$CH_2NHMe$. Definitions and preferred definitions of b are as described above in relation to formulae (VI), (IV), (V) and (VII). Preferably b is an integer from 1 to 100.

Still more preferably the compound of formula (VIII) is $CF_3CF_2CF_2O$—$[CF(CF_3)CF_2O]_b$—$CF(CF_3)$—$CH_2OH$, $CF_3CF_2CF_2O$—$[CF(CF_3)CF_2O]_b$—$CF(CF_3)$—$CH_2OC(O)$ $OC_6H_4NO_2$ or —$CF_3CF_2CF_2O$—$[CF(CF_3)CF_2O]_b$—$CF(CF_3)$—$CH_2NHMe$. Definitions and preferred definitions of b are as described above in relation to formulae (VI), (IV), (V) and (VII).

In some preferred methods of the present invention the compound of formula (VIII) is selected from the group consisting of $CF_3CF_2CF_2O$—$[CF(CF_3)CF_2O]_b$—$CF(CF_3)$—$C(O)OH$, $CF_3CF_2CF_2O$—$[CF(CF_3)CF_2O]_b$—$CF(CF_3)$—$C(O)NH_2$, $CF_3CF_2CF_2O$—$[CF(CF_3)CF_2O]_b$—$CF(CF_3)$—$C(O)Cl$, $CF_3CF_2CF_2O$—$[CF(CF_3)CF_2O]_b$—$CF(CF_3)$—$C(O)OMe$, $CF_3CF_2CF_2O$—$[CF(CF_3)CF_2O]_b$—$CF(CF_3)$—$CH_2OC_6H_4SO_2Cl$, $CF_3CF_2CF_2O$—$[CF(CF_3)CF_2O]_b$—$CF(CF_3)$—$CH_2SO_2Cl$, $CF_3CF_2CF_2O$—$[CF(CF_3)CF_2O]_b$—$CF(CF_3)$—$CH_2OC(O)OC_6H_4NO_2$, $CF_3CF_2CF_2O$—$[CF(CF_3)CF_2O]_b$—$CF(CF_3)$—$CH_2OH$, $CF_3CF_2CF_2O$—$[CF(CF_3)CF_2O]_b$—$CF(CF_3)$—$CH_2OPh$, $CF_3CF_2CF_2O$—$[CF(CF_3)CF_2O]_b$—$CF(CF_3)$—$CH_2NCO$ and $CF_3CF_2CF_2O$—$[CF(CF_3)CF_2O]_b$—$CF(CF_3)$—$CH_2NH_2$, wherein definitions and preferred definitions of b are as described above in relation to formulae (VI), (IV), (V) and (VII).

More preferably the compound of formula (VIII) is selected from the group consisting of $CF_3CF_2CF_2O$—$[CF(CF_3)CF_2O]_b$—$CF(CF_3)$—$CH_2OC_6H_4SO_2Cl$, $CF_3CF_2CF_2O$—$[CF(CF_3)CF_2O]_b$—$CF(CF_3)$—$CH_2SO_2Cl$, $CF_3CF_2CF_2O$—$[CF(CF_3)CF_2O]_b$—$CF(CF_3)$—$CH_2OC(O)$ $OC_6H_4NO_2$, $CF_3CF_2CF_2O$—$[CF(CF_3)CF_2O]_b$—$CF(CF_3)$—$CH_2OH$, $CF_3CF_2CF_2O$—$[CF(CF_3)CF_2O]_b$—$CF(CF_3)$—$CH_2NCO$ and $CF_3CF_2CF_2O$—$[CF(CF_3)CF_2O]_b$—$CF(CF_3)$—$CH_2NH_2$. Definitions and preferred definitions of b are as described above in relation to formulae (VI), (IV), (V) and (VII). Preferably b is an integer from 1 to 100.

Still more preferably the compound of formula (VIII) is $CF_3CF_2CF_2O$—$[CF(CF_3)CF_2O]_b$—$CF(CF_3)$—$CH_2OH$ or $CF_3CF_2CF_2O$—$[CF(CF_3)CF_2O]_b$—$CF(CF_3)$—$CH_2OC(O)$ $OC_6H_4NO_2$. Definitions and preferred definitions of b are as described above in relation to formulae (VI), (IV), (V) and (VII).

In some preferred methods of the invention the compound of formula (XI) is selected from TsO—$CH_2CH_2$—$[OCH_2CH_2]_e$—OTs, MsO—$CH_2CH_2$—$[OCH_2CH_2]_e$—OMs, $NO_2C_6H_4OC(O)O$—$CH_2CH_2$—$[OCH_2CH_2]_e$—$OC(O)OC_6H_4NO_2$, OCN—$CH_2CH_2$—$[CH_2O]_f$—$[OCH_2CH_2]_e$—NCO, $H_2N$—$[CH_2]_3$—$[OCH_2CH_2]_e$—$CH_2$—$NH_2$ and $H_2N$—$[CH(CH_3)CH_2O]_f$—$[CH_2CH_2O]_e$—$[CH_2CH(CH_3)O]_{f'}$—$CH_2CH(CH_3)$—$NH_2$ wherein definitions and preferred definitions of e, f and f' are as set out above in relation to formulae (VI), (IV), (V) and (VII). f and f' may be the same or they may be different. Preferably e is an integer from 1 to 100, e.g. 10 to 30. Preferably f and f' are each independently an integer from 1 to 50, e.g. 1 to 5.

Particularly preferably the compound of formula (XI) is TsO—$CH_2CH_2$—$[OCH_2CH_2]_e$—OTs, $NO_2C_6H_4OC(O)O$—$CH_2CH_2$—$[OCH_2CH_2]_e$—$OC(O)OC_6H_4NO_2$, OCN—$CH_2CH_2$—$[OCH_2CH_2]_e$—NCO, $H_2N$—$[CH_2]_3$—$[OCH_2CH_2]_e$—$CH_2$—$NH_2$ or $H_2N$—$[CH(CH_3)CH_2O]_{f'}$—$[CH_2CH_2O]_e$—$[CH_2CH(CH_3)O]_{f'}$—$CH_2CH(CH_3)$—$NH_2$.

In some preferred methods of the invention the compound of formula (XI) is selected from TsO—$CH_2CH_2$—$[OCH_2CH_2]_e$—OTs, MsO—$CH_2CH_2$—$[OCH_2CH_2]_e$—OMs, $NO_2C_6H_4OC(O)O$—$CH_2CH_2$—$[OCH_2CH_2]_e$OC(O) $OC_6H_4NO_2$ and $H_2N$—$[CH(CH_3)CH_2O]_{f'}$—$[CH_2CH_2O]_e$—$[CH_2CH(CH_3)O]_{f'}$—$CH_2CH(CH_3)$—$NH_2$ wherein definitions and preferred definitions of e, f and f' are as set out above in relation to formulae (VI), (IV), (V) and (VII). f and f' may be the same or they may be different. Preferably e is an integer from 1 to 100, e.g. 10 to 30. Preferably f and f' are each independently an integer from 1 to 50, e.g. 1 to 5. Particularly preferably the compound of formula (XI) is TsO—$CH_2CH_2$—$[OCH_2CH_2]_e$—OTs or $H_2N$—$[CH(CH_3)CH_2O]_{f'}$—$[CH_2CH_2O]_e$—$[CH_2CH(CH_3)O]_{f'}$—$CH_2CH(CH_3)$—$NH_2$.

The surfactants of the present invention may be incorporated into compositions. Thus compositions comprising a surfactant as hereinbefore defined form another aspect of the present invention.

The compounds having a formula selected from the group consisting of (VI), (IV), (V), (VII) and (II) as hereinbefore defined are for use as surfactants. Thus in another aspect the present invention relates to the use of a compound having a formula selected from the group consisting of (VI), (IV), (V), (VII) and (II)) as hereinbefore defined as a surfactant. The surfactants of the invention may be used to stabilise an emulsion, more particularly to stabilise a discontinuous aqueous phase, e.g. one or more aqueous droplets, in a continuous oil phase, e.g. a continuous oil phase comprising a fluorous oil. The perfluoropolyether component of the surfactants of the present invention acts as a fluorophilic tail, and is soluble in an oil phase, e.g. the continuous oil phase of an emulsion, particularly wherein the oil phase comprises a fluorous oil, e.g. a fluorous oil phase. The polyalkylene oxide unit of the surfactants of the invention acts as a hydrophilic headgroup, and is soluble in an aqueous phase, e.g. the discontinuous aqueous phase of an emulsion.

The surfactants of the present invention may be used in the preparation of an emulsion. The present invention thus also relates to the use of a surfactant as hereinbefore described in the preparation of an emulsion.

The present invention also relates to an emulsion comprising a surfactant as hereinbefore described. Preferred emulsions of the present invention comprise a discontinuous aqueous phase, a continuous oil phase and a surfactant as hereinbefore described. The emulsions may comprise aqueous phase, oil phase and surfactants in any amounts suitable to form an emulsion. The skilled man will be readily able to determine such amounts.

Preferably, the continuous oil phase of the emulsions of the invention comprises a fluorous oil. The fluorous oil is preferably a partially fluorinated hydrocarbon, a perfluorocarbon, a hydrofluoroether, or a mixture thereof. Particularly preferably the fluorous oil is a hydrofluoroether. Preferred fluorous oils present in the continuous oil phase of the emulsions of the present invention are Novec™ 7500 (3-ethoxy-1,1,1,2,3,4,4,5,5,6,6,6-dodecafluoro-2-(trifluoromethyl)-hexane), Novec™ 7300 (1,1,1,2,2,3,4,5,5,5-decafluoro-3-methoxy-4-(trifluoromethyl)-pentane), Novec™ 7200 ($C_4F_9OC_2H_5$), Novec™ 7100 ($C_4F_9OCH_3$), Fluorinert™ FC-72, Fluorinert™ FC-84, Fluorinert™ FC-77, Fluorinert™ FC-40, Fluorinert™ FC3283, Fluorinert™ FC-43, Fluorinert™ FC-70, perfluorodecalin and mixtures thereof. More preferred fluorous oils are Novec™ 7500 (3-ethoxy-1,1,1,2,3,4,4,5,5,6,6,6-dodecafluoro-2-(trifluoromethyl)-hexane), Fluorinert™ FC-40, Fluorinert™ FC3283 and perfluorodecalin, and still more preferred is Novec™ 7500 (3-ethoxy-1,1,1,2,3,4,4,5,5,6,6,6-dodecafluoro-2-(trifluoromethyl)-hexane).

In preferred emulsions of the present invention, the discontinuous aqueous phase comprises a plurality of droplets. The droplets preferably have an average diameter of 1 μm to 500 μm, more preferably 10 to 150 μm and still more preferably 30 to 120 μm. This is advantageous because the volume of a droplet is therefore small, and thus the amount of material, e.g. biological material, needed is small. It is preferred that at least some of the droplets comprise one or more analytes. Preferably each droplet comprises an average number of 0 to 100 analytes, more preferably 1 to 20 and still more preferably 1 to 5, e.g. 1 analyte.

In preferred emulsions of the present invention comprising a plurality of droplets, at least some of the droplets further comprise an aqueous and non-aqueous phase, a chemical buffer, a biochemical buffer or a culture or other media. Examples of suitable chemical buffers include ammonium bicarbonate, ammonium acetate and phosphate-buffered saline (PBS). Examples of suitable biochemical buffers include HEPES, PBS and Trizma.

In emulsions of the invention comprising a plurality of droplets wherein at least some of the droplets comprise one or more analytes, the analyte may be any entity of interest. In one group of emulsions of the invention comprising a plurality of droplets wherein at least some of the droplets comprise one or more analytes, the analytes are preferably biological molecules selected from small molecules, amino acids, peptides, proteins, antibodies, enzymes, monosaccharides, disaccharides, oligosaccharides, polysaccharides, nucleic acids, oligonucleotides, nucleotides, metabolites, cofactors and artificially engineered molecules. More preferably the biological molecules are selected from antibodies, enzymes, oligonucleotides and metabolites and still more preferably from antibodies and metabolites. Optionally the biological molecules may be contained in cells (e.g. mammalian cells, plant cells, algal cells, yeast cells, hybridomas, microorganisms), cell organelles (e.g. cell nuclei, mitochondria), viruses or prions.

In another group of emulsions of the invention comprising a plurality of droplets wherein at least some of the droplets comprise one or more analytes, the analytes are biological analytes, e.g. cells, sub-cellular complexes of cellular building blocks or components. The biological analytes are preferably selected from cells (e.g. mammalian cells, plant cells, algal cells, microbial cells, yeast cells), primary B-cells, T-cells, hybridomas, microorganisms, viruses, bacteria, or prions, cell organelles (e.g. cell nuclei, mitochondria) or exosomes, more preferably from B-cells, T-cells, hybridomas and microorganisms, and still more preferably from hybridomas and microorganisms. When the biological analyte is a cell, the cell is preferably selected from mammalian cells, plant cells, algal cells, microbial cells, more preferably from mammalian cells and microbial cells and still more preferably from mammalian cells. Preferably molecules are produced in, excreted or secreted from the cells, e.g. molecules are excreted or secreted from the cells. When the biological analyte is a cell organelle, the cell organelle is preferably selected from cell nuclei and mitochondria.

In a further group of emulsions of the invention comprising a plurality of droplets wherein at least some of the droplets comprise one or more analytes, the analytes are assay components which are preferably selected from beads, nanoparticles, crystals, micelles, quantum dots, detection reagents, antibodies, enzyme co-factors, nucleic acid amplification reagents, oligonucleotide sequencing reagents, cell transformation reagents, cell transduction mixtures and genome editing reagents. More preferably the assay components are selected from beads, detection reagents, nucleic acid amplification reagents and genome editing reagents, still more preferably detection reagents.

When at least some of the droplets contain a living entity, e.g. cell or bacterium, the aqueous phase preferably comprises a culture or growth medium. Any conventional medium may be used. The medium may, for example, comprise glucose, vitamins, amino acids, proteins, salts, pH indicators and density matching reagents, e.g. Ficoll. Sufficient medium must be provided to keep the entity alive for the duration of the analysis, reaction or other process of interest, e.g. sorting in a microfluidic device.

The present invention also relates to a method of preparing an emulsion as hereinbefore described, comprising:
(i) preparing an aqueous phase;
(ii) preparing an oil phase; and
(iii) mixing the aqueous phase, the oil phase and a surfactant as hereinbefore described to form the emulsion.

In one group of preferred methods of preparing an emulsion the surfactant is mixed with (e.g. dissolved in) the oil phase prior to mixing with said aqueous phase. Preferably, the surfactant is dissolved in the oil phase at a concentration of 0.001% (w/w) to 20% (w/w), more preferably 0.1% (w/w) to 10% (w/w) and still more preferably 0.5% (w/w) to 5% (w/w). Preferably, the aqueous phase comprises at least one analyte. In some preferred methods the oil phase may be a solution of the surfactant in a fluorous solvent. In other words, the surfactant may be dissolved in a fluorous solvent to give the oil phase.

In alternative preferred methods of preparing an emulsion the surfactant is mixed with (e.g. dissolved in) the aqueous phase prior to mixing with the oil phase.

In further preferred methods of preparing an emulsion the surfactant is mixed with (e.g. dissolved in) the aqueous phase and is separately mixed with (e.g. dissolved in) the oil phase prior to mixing of the aqueous phase with the oil phase. Any conventional mixing method may be used, e.g. T-junction, step emulsification, flow focus junction etc.

In preferred methods of preparing an emulsion as hereinbefore described the mixing is by a flow focus junction of a microfluidic device, e.g. a microfluidic device as disclosed in WO 2012/022976 and WO 2015/015199. This is advantageous because it enables very small aqueous phases, e.g. microdroplets, to be produced, with volumes typically in the order of picolitres or nanoliters.

Further preferred features of the method of preparing an emulsion are the same as the preferred features of the emulsion described above. Thus preferably the emulsion, the aqueous phase and the oil phase are as defined above in relation to the emulsion.

Experiments, assays, reactions and processes may be carried out in the emulsions of the present invention. The discontinuous aqueous phase of the emulsion, e.g. aqueous droplets, may serve as the site for the experiments, assays, reactions and processes. The surfactants of the present invention stabilise the emulsion, e.g. a discontinuous aqueous phase in an oil phase, allowing the experiment, assay, reaction or process to be carried out in the emulsion. The experiment, assay, reaction or process may therefore be carried out without the discontinuous aqueous phase, e.g. aqueous droplets, coalescing. The experiment, assay, reaction or process may involve one or more analytes present in the aqueous phase of the emulsion. Thus a method of performing one or more experiments, assays, reactions and processes within an emulsion, e.g. within the discontinuous aqueous phase (preferably aqueous droplets) of an emulsion as hereinbefore described forms another aspect of the present invention. The experiments, assays, reactions and processes carried out in the emulsions of the present invention may be carried out in a microfluidic channel or in a microfluidic device, e.g. the experiments, assays, reactions and processes may be carried out in one or more channels of a microfluidic device.

The present invention thus also relates to a method of performing one or more chemical and/or biological reactions, and/or biological processes in the discontinuous aqueous phase of an emulsion as hereinbefore described.

In one aspect the method of performing one or more chemical and/or biological reactions, and/or biological processes in the discontinuous aqueous phase of an emulsion as hereinbefore described is preferably a method of performing one or more chemical and/or biological reactions. The chemical and/or biological reaction may be an enzymatic reaction. Alternatively, the chemical and/or biological reaction is a molecular binding, molecular interaction, cellular interaction or conformational change resulting in a measurable signal. Preferably the chemical and/or biological reaction is an enzyme reaction, a molecular binding or a molecular/cellular interactions.

In another aspect the method of performing one or more chemical and/or biological reactions, and/or biological processes in the discontinuous aqueous phase of an emulsion as hereinbefore described is preferably a method of performing one or more biological processes. The biological process may be antibody secretion or enzyme secretion by cells, or enzyme production inside cells. Alternatively the biological process is antibody binding. In alternative methods the biological process may be a nucleic acid amplification process, partial or full nucleic acid replication process or nucleic acid transcription process. Alternatively, the biological process may be cell proliferation, cell metabolism, cell transfection, cell transduction, cell signalling, cell apoptosis or cell death. Preferably the biological process is PCR. The process used could be for digital PCR.

In another aspect of the method of performing one or more biological processes the biological process may be a genome editing process. The biological process may be sample preparation, e.g. oligonucleotide sample preparation process for sequencing. The biological process may be nucleic acid sequencing. The molecules being sequenced could be RNA or DNA and the sequencing could be at the genomic, epigenomic or transcriptomic level.

The method of performing one or more chemical and/or biological reactions, and/or biological processes in the discontinuous aqueous phase of an emulsion as hereinbefore described may comprise one or more chemical reactions, one or more biological reactions, one or more biological processes or a mixture thereof. Preferred chemical and/or biological reactions, and/or biological processes are as described above.

Preferably, the method of performing one or more chemical and/or biological reactions, and/or biological processes in the discontinuous aqueous phase of an emulsion as hereinbefore described is carried out in a microfluidic channel or microfluidic device. This enables chemical and/or biological reactions and/or biological processes to be performed on a very small scale, e.g. in microdroplets, and so very little material, e.g. biological material, is required. The microfluidic channel or device is preferably controlled by an automated device and software.

Preferably, the method of performing one or more chemical and/or biological reactions, and/or biological processes in the discontinuous aqueous phase of an emulsion as hereinbefore described is carried out under thermal, pH or environmental cycling conditions.

The surfactants and emulsions of the present invention have many useful applications. They particularly have many potential uses in microfluidics applications. For example, the surfactants and/or emulsions hereinbefore defined may be used in methods of sorting droplets, coalescing droplets or introducing fluid into a droplet. The surfactants and/or emulsions may also be used in methods of extracting a protein from a fluid. These methods are preferably carried in a microfluidic device.

The present invention thus also relates to a method for sorting droplets in a microfluidic device. A preferred method for sorting droplets in a microfluidic device comprises:
(i) providing a stream of aqueous droplets in an emulsion as hereinbefore defined in a channel of the microfluidic device;
(ii) illuminating the stream from a first direction;
(iii) detecting light from analytes within the droplets in a second direction; and
(iv) sorting the droplets into one of a plurality of differentiated streams responsive to the detected light or a measurable signal. Preferably, the method comprises sorting the droplets into one of a plurality of differentiated streams responsive to the detected light.

An alternative method for sorting droplets in a microfluidic device comprises:
(i) providing a stream of aqueous droplets in an emulsion as hereinbefore defined in a channel of the microfluidic device;
(ii) measuring and detecting analytes or entities within the droplets; and
(iii) sorting the droplets into one of a plurality of differentiated streams responsive to a detected change or a measurable signal.

The present invention also relates to a method of coalescing droplets in a microfluidic device. One preferred method of coalescing droplets in a microfluidic device comprises:
(i) providing at least two aqueous droplets in an emulsion as hereinbefore described in a channel of the microfluidic device; and
(ii) exposing the aqueous droplets to an electric field, thereby causing coalescence of the at least two aqueous droplets into a single droplet.

Another preferred method of coalescing droplets in a microfluidic device comprises:
(i) providing at least two aqueous droplets in an emulsion as hereinbefore defined in a channel of the microfluidic device; and
(ii) exposing the aqueous droplets to a physical constriction thereby causing coalescence of the at least two aqueous droplets into a single droplet.

An alternative preferred method of coalescing droplets in a microfluidic device comprises:
(i) providing at least two aqueous droplets of different sizes in an emulsion as hereinbefore defined in a channel of the microfluidic device; and
(ii) bringing the aqueous droplets into close physical proximity thereby causing coalescence of the at least two aqueous droplets into a single droplet.

A further preferred method of coalescing droplets in a microfluidic device comprises:
- (i) providing at least one aqueous droplet in an emulsion as hereinbefore defined in a channel of the microfluidic device; and
- (ii) introducing in an aqueous sample from a different channel
- (iii) bringing the aqueous droplet and sample into close physical proximity thereby causing coalescence of the at least two aqueous samples into a single droplet.

Yet another preferred method of coalescing droplets in a microfluidic device comprises:
- (i) providing at least two aqueous droplets of different sizes in an emulsion as hereinbefore defined in a channel of the microfluidic device; and
- (ii) treating the aqueous droplets with acoustic energy thereby causing coalescence of the at least two aqueous droplets into a single droplet.

Another preferred method of coalescing droplets in a microfluidic device comprises:
- (i) providing at least one aqueous droplet in an emulsion as hereinbefore defined in a channel of the microfluidic device; and
- (ii) introducing in an aqueous stream;
- (iii) treating the aqueous droplet and aqueous samples with acoustic energy thereby causing coalescence of the at least two aqueous samples into a single droplet.

An alternative preferred method of coalescing droplets in a microfluidic device comprises:
- (i) providing at least two aqueous droplets of different sizes in an emulsion as hereinbefore defined in a channel of the microfluidic device; and
- (ii) treating/manipulating the aqueous droplets with optical tweezers and/or other type of light manipulation thereby causing coalescence of the at least two aqueous droplets into a single droplet A further preferred method of coalescing droplets in a microfluidic device comprises:
- (i) providing at least one aqueous droplet in an emulsion as hereinbefore defined in a channel of the microfluidic device; and
- (ii) introducing in an aqueous stream in a different microfluidic channel;
- (iii) treating/manipulating the aqueous samples with optical tweezers and/or other type of light manipulation thereby causing coalescence of the at least two aqueous samples into a single droplet The present invention also relates to a method of introducing a fluid into a droplet in a microfluidic device, the method comprising:
- (i) providing an aqueous droplet in an emulsion as hereinbefore described in a channel of the microfluidic device; and
- (ii) contacting the aqueous droplet with a stream of fluid, thereby introducing the fluid into the aqueous droplet.

The present invention also relates to a method of splitting droplets in a microfluidic device. One preferred method of splitting droplets in a microfluidic device comprises:
- (i) providing a microfluidic device comprising a microfluidic junction, said microfluidic junction comprising a first microfluidic channel, a second microfluidic channel and a third microfluidic channel;
- (ii) providing an aqueous droplet in an emulsion as hereinbefore defined in said first microfluidic channel; and
- (iii) passing the aqueous droplet through the microfluidic junction, thereby splitting said aqueous droplet into at least a first daughter droplet and a second daughter droplet, the first daughter droplet in the second microfluidic channel and the second daughter droplet in the third microfluidic channel.

A second preferred method of splitting droplets in a microfluidic device comprises:
- (i) providing at least one aqueous droplet in an emulsion as hereinbefore defined in a channel of the microfluidic device; and
- (ii) splitting the aqueous droplet to generate at least two droplets using an electric field, thereby causing formation of the at least two aqueous droplets from a single droplet.

A further preferred method of splitting droplets in a microfluidic device comprises:
- (i) providing at least one aqueous droplet in an emulsion as hereinbefore defined in a channel of the microfluidic device; and
- (ii) splitting the aqueous droplet to generate at least two droplets using physical collision and/constriction and/or barrier(s) and/or any combination of before mentioned actions thereby causing formation of the at least two aqueous droplets from a single droplet.

Another preferred method of splitting droplets in a microfluidic device comprises:
- (i) providing at least one aqueous droplet in an emulsion as hereinbefore defined in a channel of the microfluidic device; and
- (ii) splitting the aqueous droplet to generate at least two droplets using optical tweezers and/or light energy thereby causing formation of the at least two aqueous droplets from a single droplet.

The present invention also relates to a method of extracting a molecule from a fluid, the method comprising:
- (i) dissolving a surfactant as hereinbefore described in carbon dioxide to form a carbon dioxide/surfactant mixture;
- (ii) adding a fluid comprising the molecule to the carbon dioxide/surfactant mixture, thereby extracting the molecule from the fluid into the carbon dioxide. Preferably, the method is carried out in a microfluidic device.

In preferred methods of extracting a molecule from a fluid, the molecule is a protein or a nucleic acid. More preferably, the molecule is a protein.

The methods of the invention described herein (e.g. method of preparing an emulsion, method comprising performing one or more chemical and/or biological reactions, and/or biologicial processes in the discontinuous phase of an emulsion, method for sorting droplets in a microfluidic device, method of coalescing droplets in a microfluidic device, method of introducing a fluid into a droplet in a microfluidic device, method of splitting droplets in a microfluidic device, method of extracting a molecule from a fluid) may be carried out simultaneously or sequentially (e.g. sequentially) in any combination and order. The carrying out of two or more methods of the invention may be known as a workflow of functions.

A preferred workflow of functions comprises the steps of:
- (i) preparing an emulsion as hereinbefore defined, comprising a) preparing an aqueous phase, b) preparing an oil phase, and c) mixing said aqueous phase, said oil phase and a surfactant as hereinbefore defined to form said emulsion in a microfluidic device, wherein the aqueous phase contains cells (e.g. mammalian cells, plant cells, algal cells, yeast cells, hybridomas, microorganisms), cell organelles (e.g. cell nuclei, mitochondria), viruses, or prions in a biological media; the oil phase consists of a fluorous solvents as hereinbefore defined and a surfactant as hereinbefore defined; the resultant emulsion comprises a plurality of droplets, and each droplet contains maximum one cell (e.g. mammalian cells, plant cells, algal cells, yeast cells, hybridomas, microorganisms), cell organelle (e.g. cell nuclei, mitochondria), virus, or prion;

(ii) performing a first biological processes as hereinbefore defined inside the said droplets from step (i), wherein the biological processes are cell proliferation, enzyme secretion by cells, enzyme production in cells and enzyme reaction;

(iii) sorting droplets as hereinbefore defined in a microfluidic device, comprising a) providing a stream of said aqueous droplets from step (ii) in an emulsion as hereinbefore defined in a channel of the microfluidic device; illuminating the stream from a first direction; detecting light from analytes within the droplets in a second direction, wherein detecting light is a scattered light or a fluorescence from analytes; sorting the droplets into one of a plurality of differentiated streams responsive to the detected light or a measurable signal;

(iv) optionally introducing a fluid into the said sorted droplets from step (iii) as hereinbefore defined in a microfluidic device, wherein the fluid comprises at least one biological molecule, wherein the biological molecule is selected from small molecules, proteins, enzymes, peptides, amino acids, polysaccharides, oligosaccharides, disaccharides, monosaccharides, nucleic acids, oligonucleotides, nucleotides, cofactors, and cell lysing reagents;

(v) optionally performing a second biological processes as hereinbefore defined inside the said droplets from step (iv), wherein the said biological processes are cell lysis and an enzyme reaction, wherein the said enzyme is secreted by the said cell or produced inside the said cell in step (ii), and the said enzyme reaction is to convert a said biological molecules in step (iv) into its corresponding products;

(vi) optionally quenching the said enzyme reaction in step (v) by a) treating the said droplets from step (v) at an elevated temperature for a certain period of time, wherein the temperature is from 50° C. to 98° C., and the period of time is from 10 seconds to 1 hour; b) introducing a fluid into the said droplets from step (v) as hereinbefore defined in a microfluidic device, wherein the fluid comprises an acid, an alkaline, or an enzyme inhibitor; c) storing the said droplets from step (v) at a temperature from 4° C. to 10° C.;

(vii) splitting droplets from step (iii) or (vi) as hereinbefore defined in a microfluidic device comprising a) providing droplets from step (iii) or (vi) in a first microfluidic channel of a microfluidic junctions comprising three microfluidic channels on the microfluidic device; and passing the aqueous droplet through the microfluidic junction, thereby splitting the said droplet into two daughter droplets, the first daughter droplet in the second microfluidic channel and the second daughter droplet in the third microfluidic channel;

(viii) analysing the product molecule produced from the said enzyme reaction in step (iii) or (v) inside the first daughter droplet using mass spectrometry (MS) method after evaporating and ionizing the contents of the first daughter droplet via a microfluidic electrospray ionization (i.e. ESI) emitter;

(ix) sorting the corresponding second daughter droplet in a microfluidic device responsive to MS analysis results in step (viii).

The present invention also relates to a method of measuring signal inside droplets and dispensing droplets individually or in bulk for further processing as hereinbefore defined.

The present invention also relates to various uses of the surfactants and emulsions hereinbefore described.

Thus the present invention also relates to use of a surfactant as hereinbefore described in a microfluidic channel or device.

The present invention also relates to use of a surfactant as hereinbefore described in a molecular isolation in larger fluidic devices, containers or vats.

Larger fluidic devices, containers or vats refers to devices, containers or vats which are larger than microfluidic devices. The skilled person will readily be able to distinguish between a microfluidic device and a larger device, container or vat. Preferably the larger fluidic devices, containers or vats are multi-litre sized, i.e. they have a multi-litre capacity.

The present invention also relates to use of a surfactant as hereinbefore described in an automated device with associated software that controls a microfluidic channel or device.

The present invention also relates to use of an emulsion as hereinbefore described in a microfluidic channel or device.

The present invention also relates to use of an emulsion as hereinbefore described in an automated device with associated software that controls a microfluidic channel or device.

The surfactants and emulsions hereinbefore described are suitable for use in a wide variety of applications.

Thus the present invention also relates to a surfactant as hereinbefore described for use in a microfluidic channel or device.

The present invention also relates to an emulsion as hereinbefore described for use in a microfluidic channel or device.

The present invention also relates to a surfactant as hereinbefore described for use in a molecular isolation in larger fluidic devices, containers or vats.

The present invention also relates to a surfactant as hereinbefore described for use in an automated device with associated software that controls a microfluidic channel or device.

The present invention also relates to an emulsion as hereinbefore described for use in an automated device with associated software that controls a microfluidic channel or device.

BRIEF DESCRIPTION OF FIGURES

These and other aspects of the invention will now be further described, by way of example only, with reference to the accompanying figures in which.

EXAMPLES

Materials

All starting materials employed are commercially available. Krytox™ 157 FSL (MW=2103 Dalton) was obtained from DuPont. Jeffamine® 900 and polyethylene glycol (MW=950-1050 Dalton) were obtained from Sigma Aldrich.

FC72, Anhydrous Novec 7100™ and Novec 7500™ were obtained from 3M. Oxalyl chloride, polymer-supported 4-dimethylaminopyridine, DBU (1,8-diazabicyclo(5.4.0)undec-7-ene), anhydrous methanol, sodium borohydride, diglyme, trimethylamine, methylamine, pyridine, methylmorpholine, poly(ethylene glycol) bis(3-aminopropyl) terminated, p-nitrophenylorthochloroformate, anhydrous tetrahydrofuran, anhydrous toluene, phenylsilane, polymer-supported piperidine, dichloromethane, 4-toluene sulfonylchloride, ammonium hydroxide and Fe$_3$(CO)$_{12}$ were obtained from Sigma Aldrich.

Anhydrous dimethylformamide (DMF), anhydrous sodium sulphate, ammonium carbonate, hydrochloric acid, anhydrous magnesium sulfate, anhydrous diethyl ether, toluene, hexane, 3-aminopropyl silica gel, sodium hydride and methanol, were obtained from Sigma Aldrich.

Analysis Methods

Infra-Red (IR) spectroscopy analysis was performed using a Perkin Elmer Spectrum One IR machine with diamond ATR accessory.

Nuclear Magnetic Resonance (NMR) spectroscopy analysis was performed using a 500 MHz Bruker AVANCE III HD NMR spectrometer with DCH-Cryoprobe.

Example 1: Synthesis of Surfactant (IIa)

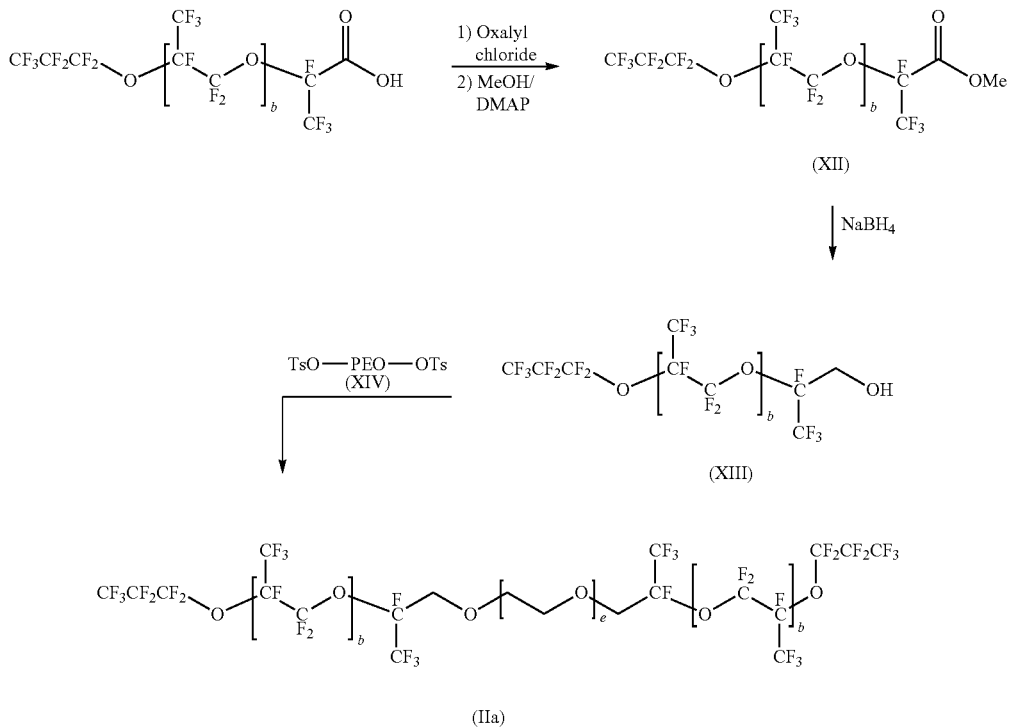

Step 1

Figure 1:
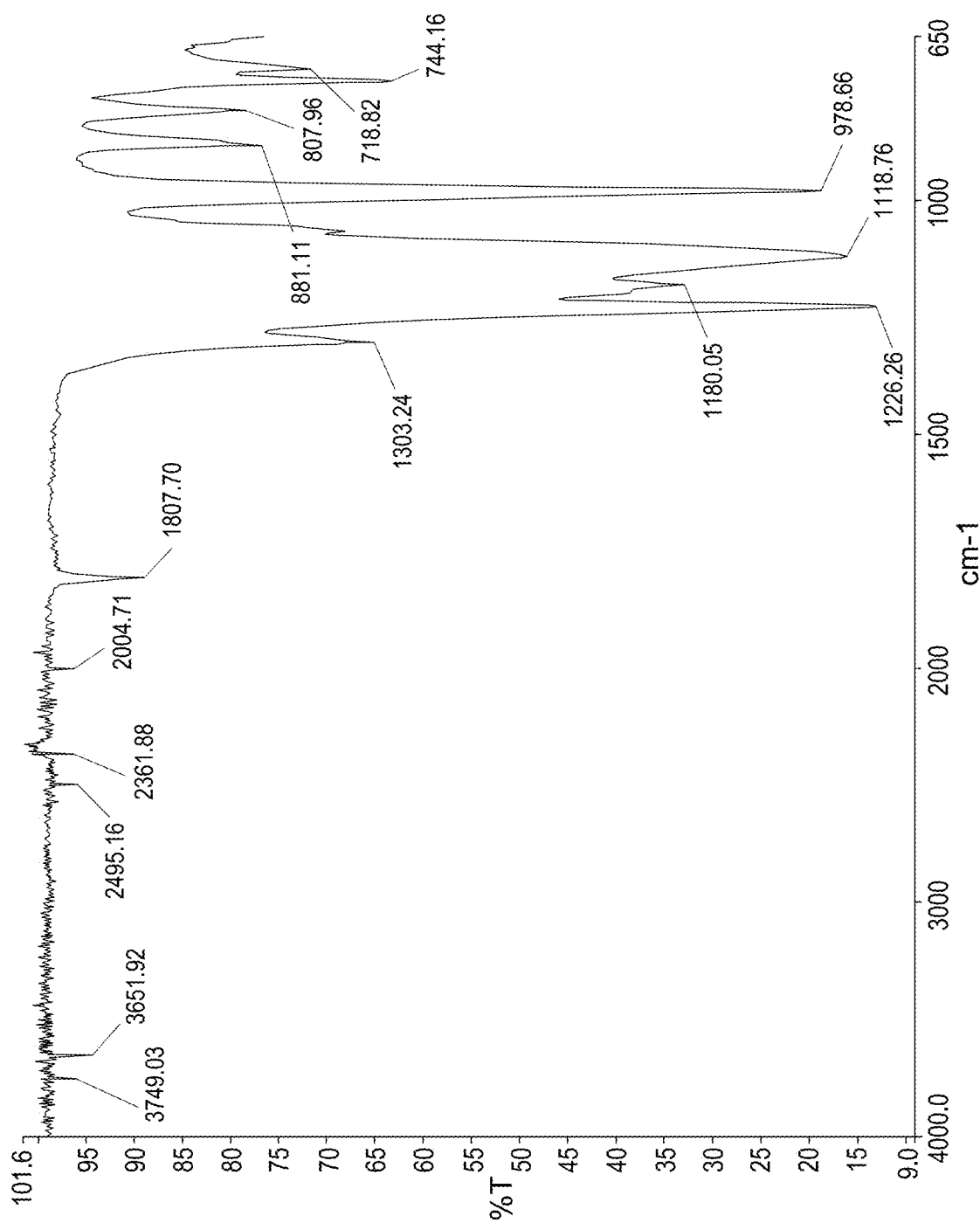
FIG. 1 is an IR spectrum of the acyl chloride product derived from the reaction of Krytox 157 FSL with oxalyl chloride.

90 g of Krytox™ 157 FSL (Mw=2103 Daltons) were placed in a 250 mL round bottom flask, equipped with a magnetic stirrer bar and sealed with a rubber seal. The flask was evacuated and refilled with nitrogen three times to de-gas the Krytox™ polymer. 75 mL of anhydrous Novec™ 7100 was added by syringe to dissolve the Krytox™. Then 105 mL of oxalyl chloride was added by syringe at room temperature followed by catalytic amounts of anhydrous DMF (one drop from a syringe needle). The reaction was stirred at room temperature overnight, decanted into a clean 250 mL round bottom flask and evaporated to dryness. Yield of acyl chloride (off-white opaque oil): quantitative. IR carbonyl stretch at 1807 cm$^{-1}$. The IR spectrum for the acyl chloride product is shown in FIG. 1.

Step 2

Figure 2:
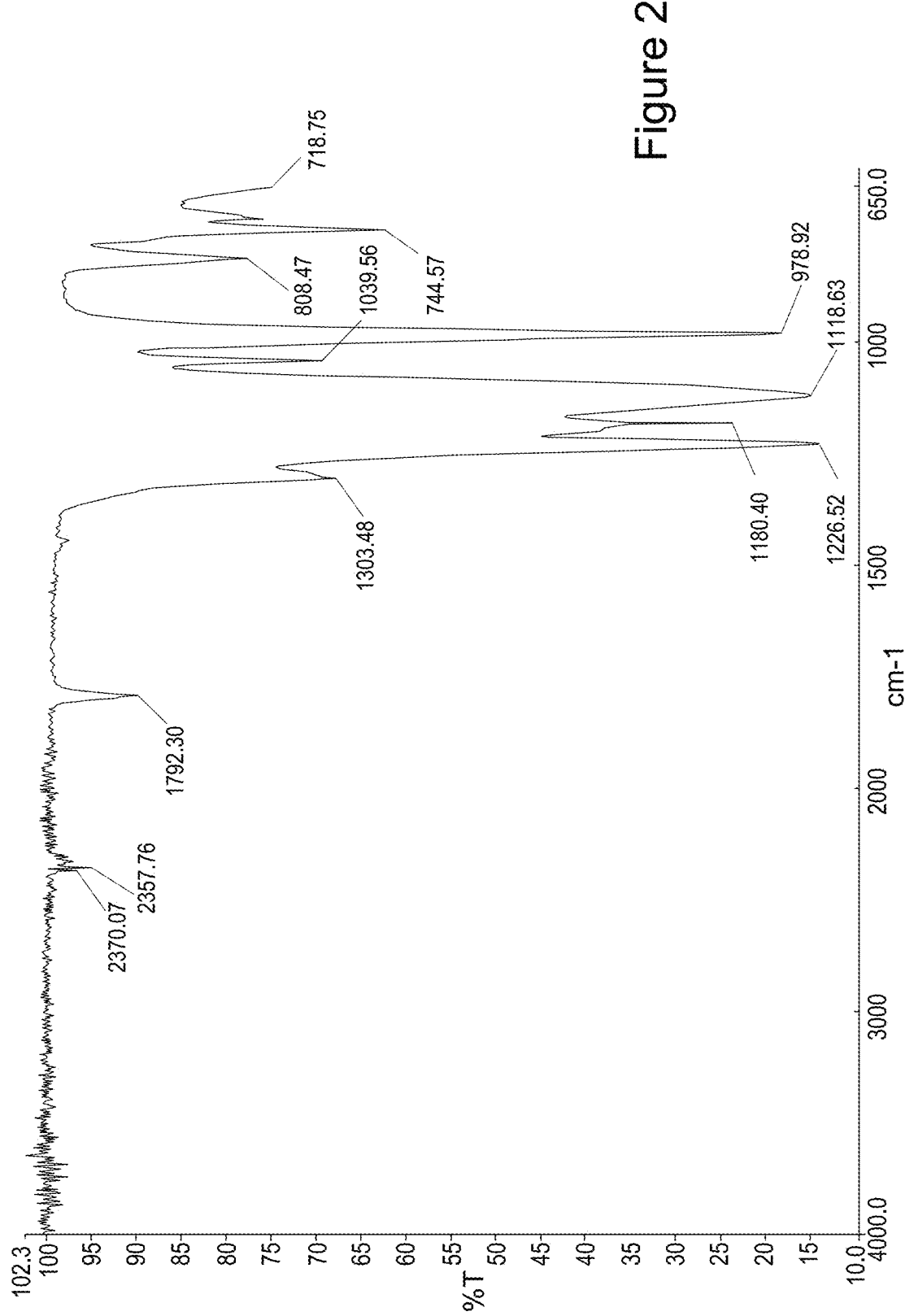
FIG. 2 is an IR spectrum of methyl ester (XII)
Figure 3:
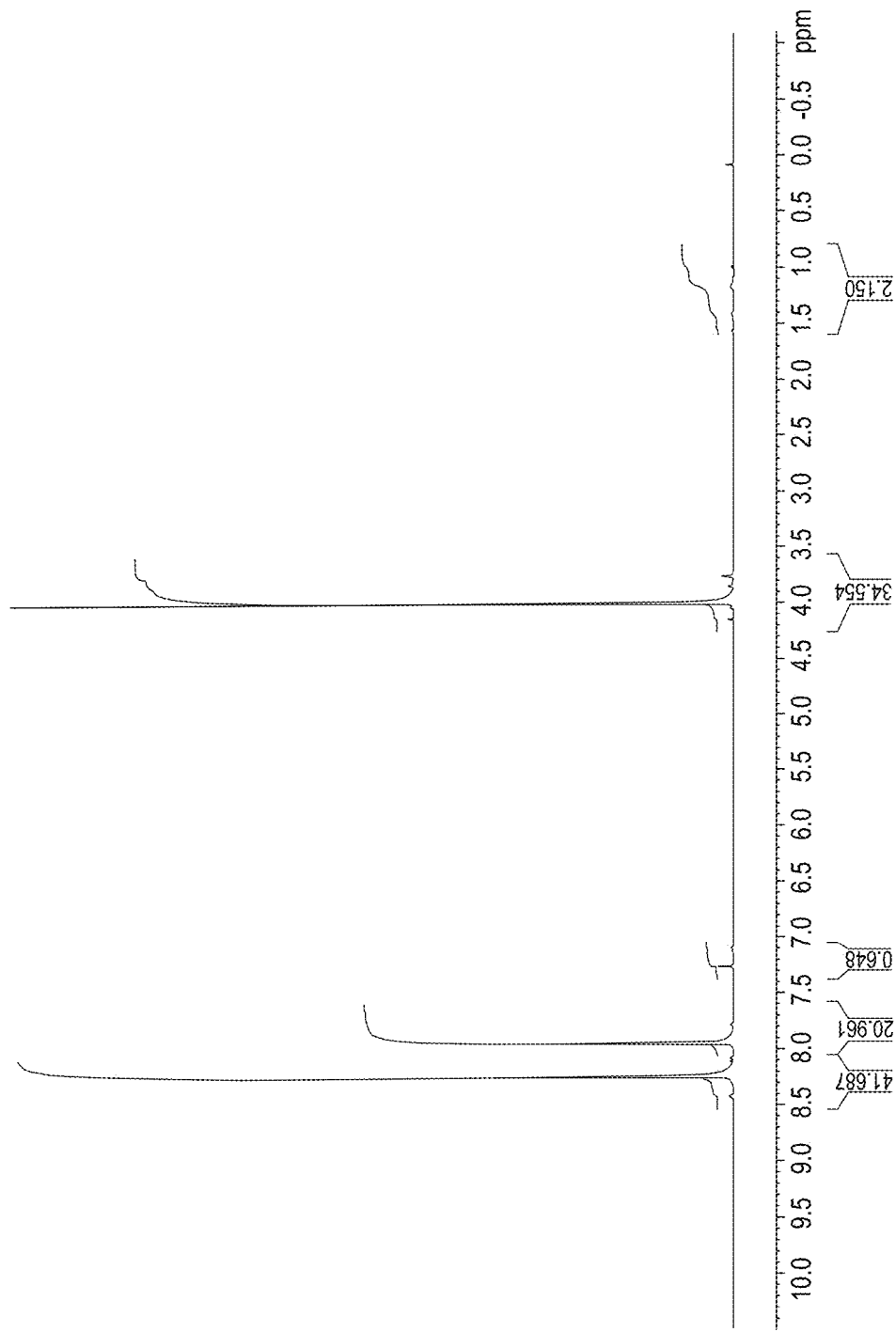
FIG. 3 is a $^1$H NMR spectrum of methyl ester (XII)

17 g of the acyl chloride product from step 1 were dissolved in anhydrous Novec™ 7100 and 2 g of polymer supported 4-dimethylaminopyridine (1.5 eq.) was added. The mixture was protected with nitrogen and 5 mL of anhydrous methanol was syringed in at room temperature. The reaction was stirred at room temperature overnight. The polymer supported 4-dimethylaminopyridine was filtered off and the filtrate evaporated to dryness. Yield of methyl ester (XI) (clear oil): 16.9 g (99.4%). IR carbonyl stretch at 1792 cm$^{-1}$, $^1$H NMR peak at 4.0 (s). The IR spectrum for the methyl ester product (XII) is shown in FIG. 2. The $^1$H NMR spectrum for the methyl ester product (XII) is shown in FIG. 3.

Step 3

Figure 4:
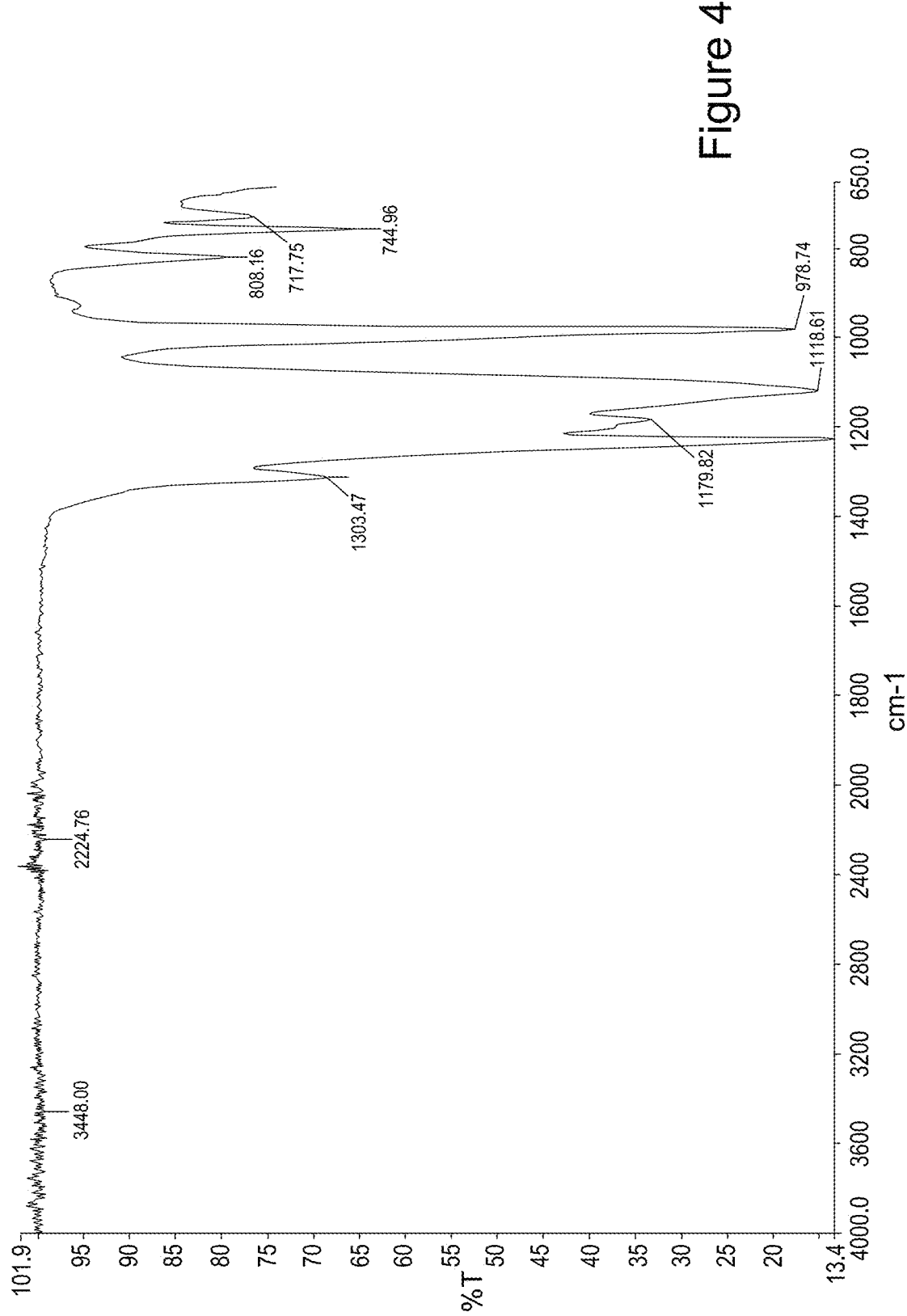
FIG. 4 is an IR spectrum of alcohol (XIII)
Figure 5:
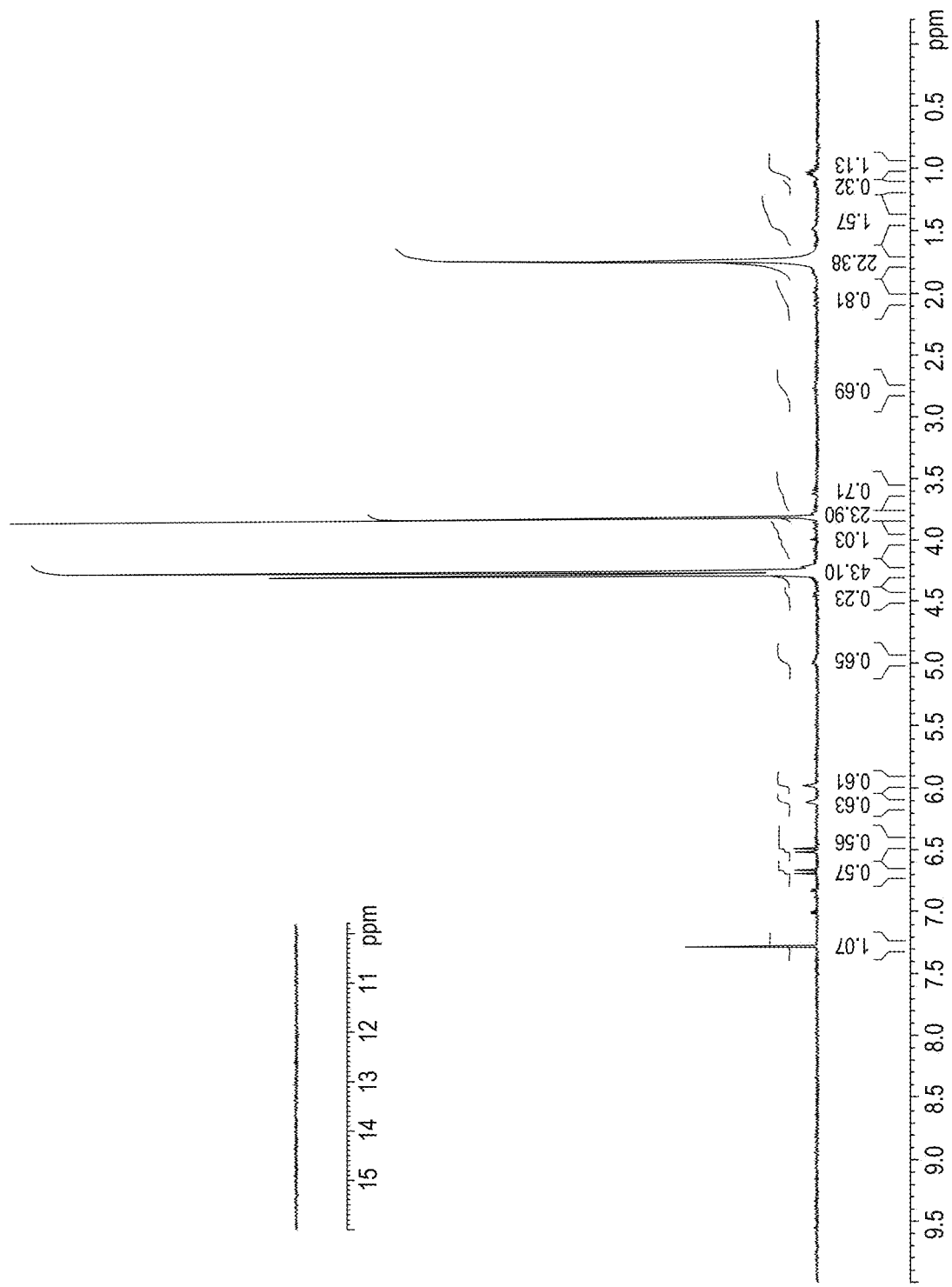
FIG. 5 is a $^1$H NMR spectrum of alcohol (XIII)

3 g of sodium borohydride was placed in a 100 mL round bottom flask and 5 mL of anhydrous Novec™ 7100 and 4 mL of diglyme were added. The mixture was placed under nitrogen in an ice bath. 16.9 g of the methyl ester product (XII) from step 2 was dissolved in 15 mL of anhydrous Novec™ 7100 and slowly added to the suspended sodium borohydride by syringe. Then the flask was fitted with a reflux condenser, protected with nitrogen and heated to 75° C. for one hour. The reaction was allowed to cool to room temperature, was diluted to 150 mL with Novec™ 7100 and quenched by pouring into 100 mL aqueous ammonium chloride/hydrochloric acid buffer (pH=7 after quench). The phases were separated and the fluorophilic phase extracted with 100 mL of water and dried over anhydrous sodium sulphate. The drying agent was removed by filtration and the filtrate evaporated to dryness. Yield of alcohol (XIII) (clear oil): 14.4 g (86%), $^1$H NMR peaks at 3.8 (s) and 4.25 (dd). The IR spectrum for the alcohol product (XIII) is shown in FIG. 4. The $^1$H NMR spectrum for the alcohol product (XIII) is shown in FIG. 5.

Step 4

Figure 6:
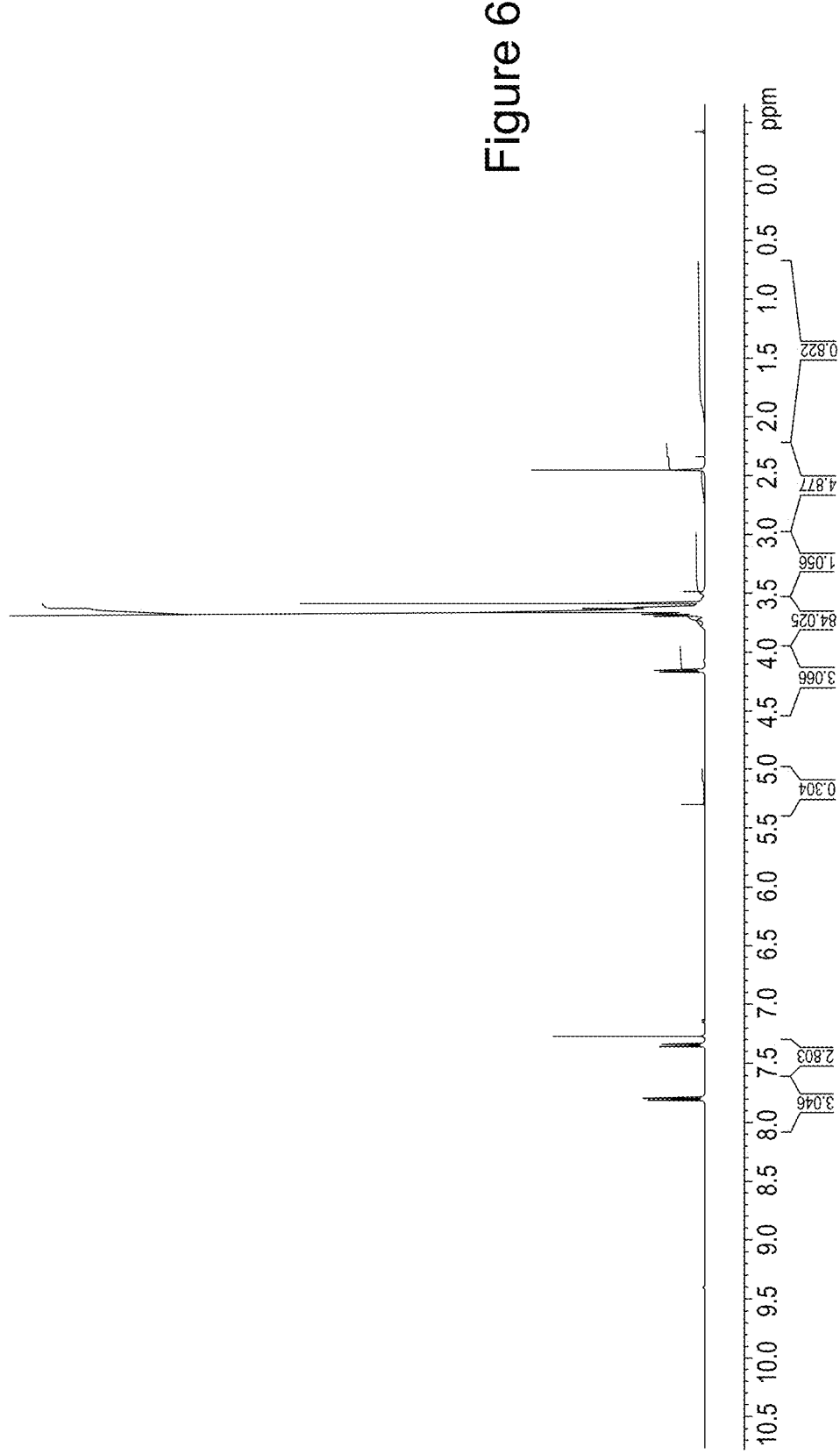
FIG. 6 is a $^1$H NMR spectrum of tosylated polyethylene glycol (XIV)

50 g of polyethylene glycol (Mw=950-1050 Dalton) was dissolved in 300 mL of dichloromethane and protected with nitrogen. 16.2 mL of pyridine was added by syringe followed by 25.7 g of 4-toluene sulfonylchloride in 100 mL of dichloromethane. The reaction was stirred at room temperature overnight. The reaction was extracted twice with 100 mL of 1 M hydrochloric acid, dried with 200 mL of saturated brine and dried over anhydrous magnesium sulfate. The drying agent was filtered off and the clear filtrate was evaporated to dryness. The oily residue was extracted three times with 50 mL of anhydrous diethyl ether and then dried in vacuo. The oily residue was refluxed in a Dean-Stark apparatus in 100 mL of toluene where a further 1 mL of water was removed. The solution was evaporated to dryness. Yield of tosylated polyethylene glycol (XIV) (off white clear oil): 47 g (72%). The $^1$H NMR spectrum for the tosylated polyethylene glycol product (XIV) is shown in FIG. 6.

Step 5

Figure 7:
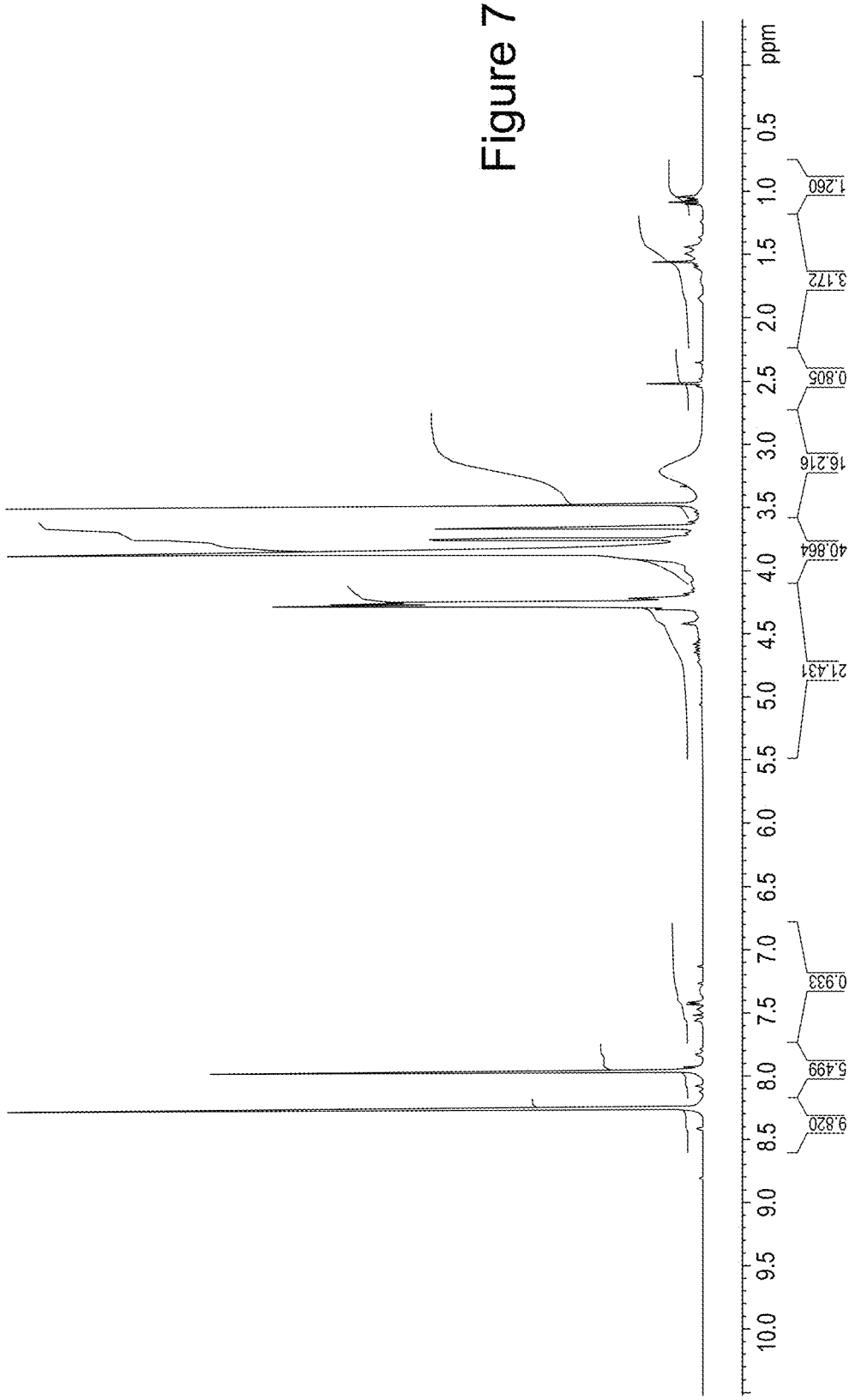
FIG. 7 is a $^1$H NMR spectrum of surfactant (IIa)

0.86 g of sodium hydride was suspended in 40 mL of anhydrous Novec™ 7100 and protected with nitrogen. 75.2 g of the alcohol product (XIII) from step 3 was dissolved in 35 mL of anhydrous Novec™ 7100 and added to the sodium hydride suspension. The suspension was warmed to 40° C. for three hours until no more gas evolved. The reaction was allowed to cool to room temperature. 22.6 g of the tosylated polyethylene glycol product (XIV) from step 4 was dissolved in 100 mL of anhydrous tetrahydrofuran and added to the suspension in 25 mL aliquots by syringe. The reaction was stirred at room temperature overnight and then heated to 65° C. for one day. The reaction was cooled to room temperature and extracted twice with 75 mL of methanol. The fluorous layer was concentrated to near dryness and the oily residue was purified by column chromatography eluting with 10% methanol in Novec™ 7100. Yield of surfactant (IIa): 12.9 g. The $^1$H NMR spectrum of the surfactant product (IIa) is shown in FIG. 7.

Example 2: Synthesis of Surfactant (IIb)

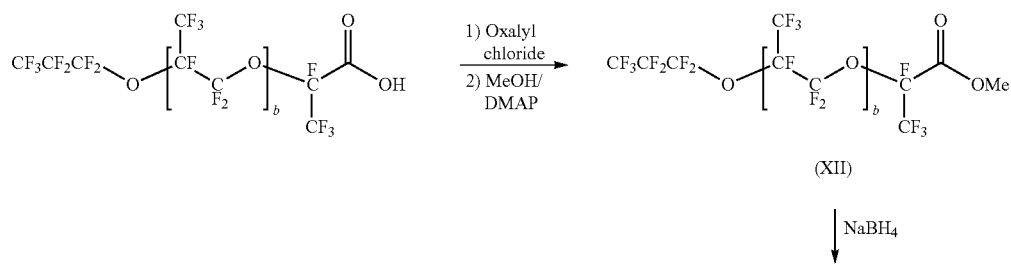

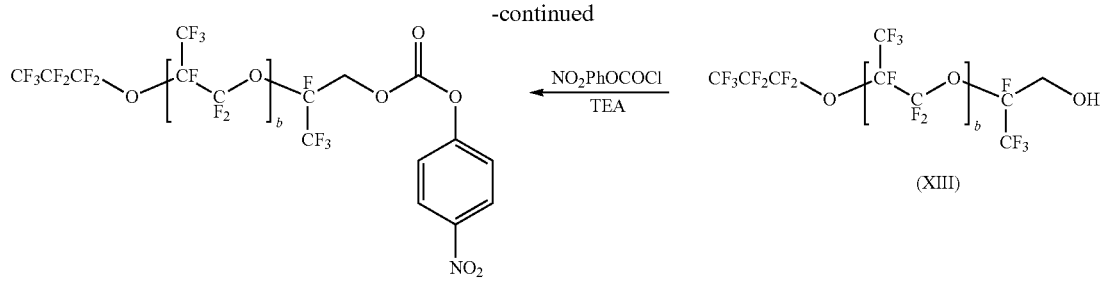

(XV)

(XIII)

Jeffamine
PS-piperidine

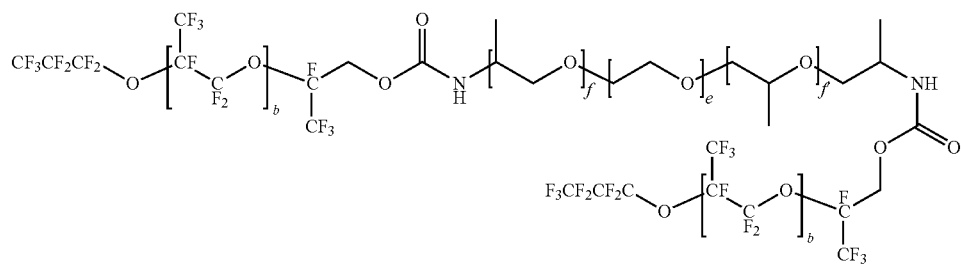

(IIb)

Steps 1 to 3 were carried out in the same manner as for Example 1.

Step 4

Figure 8:
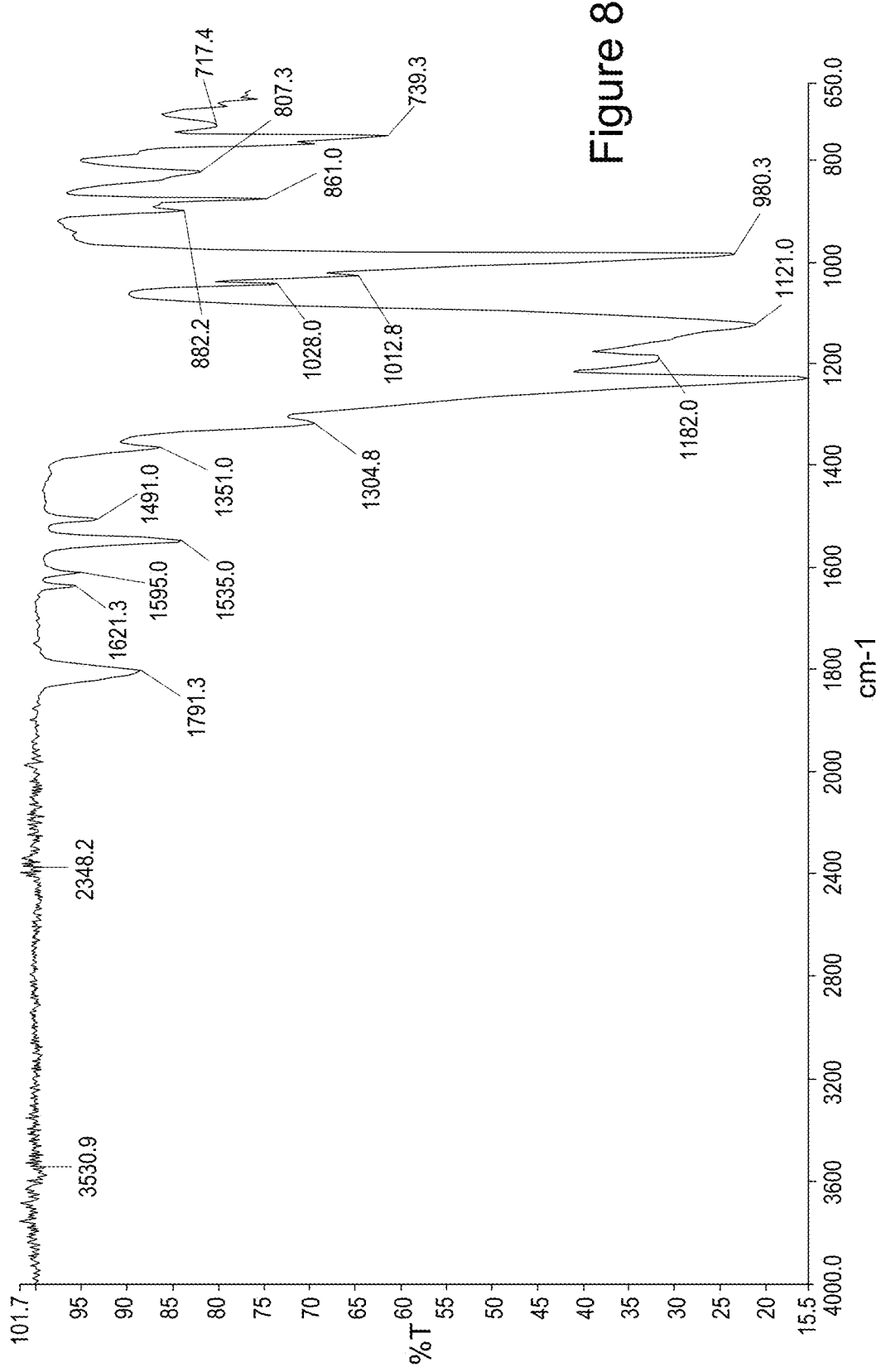
FIG. 8 is an IR spectrum of activated carbonate ester product (XV)
Figure 9:
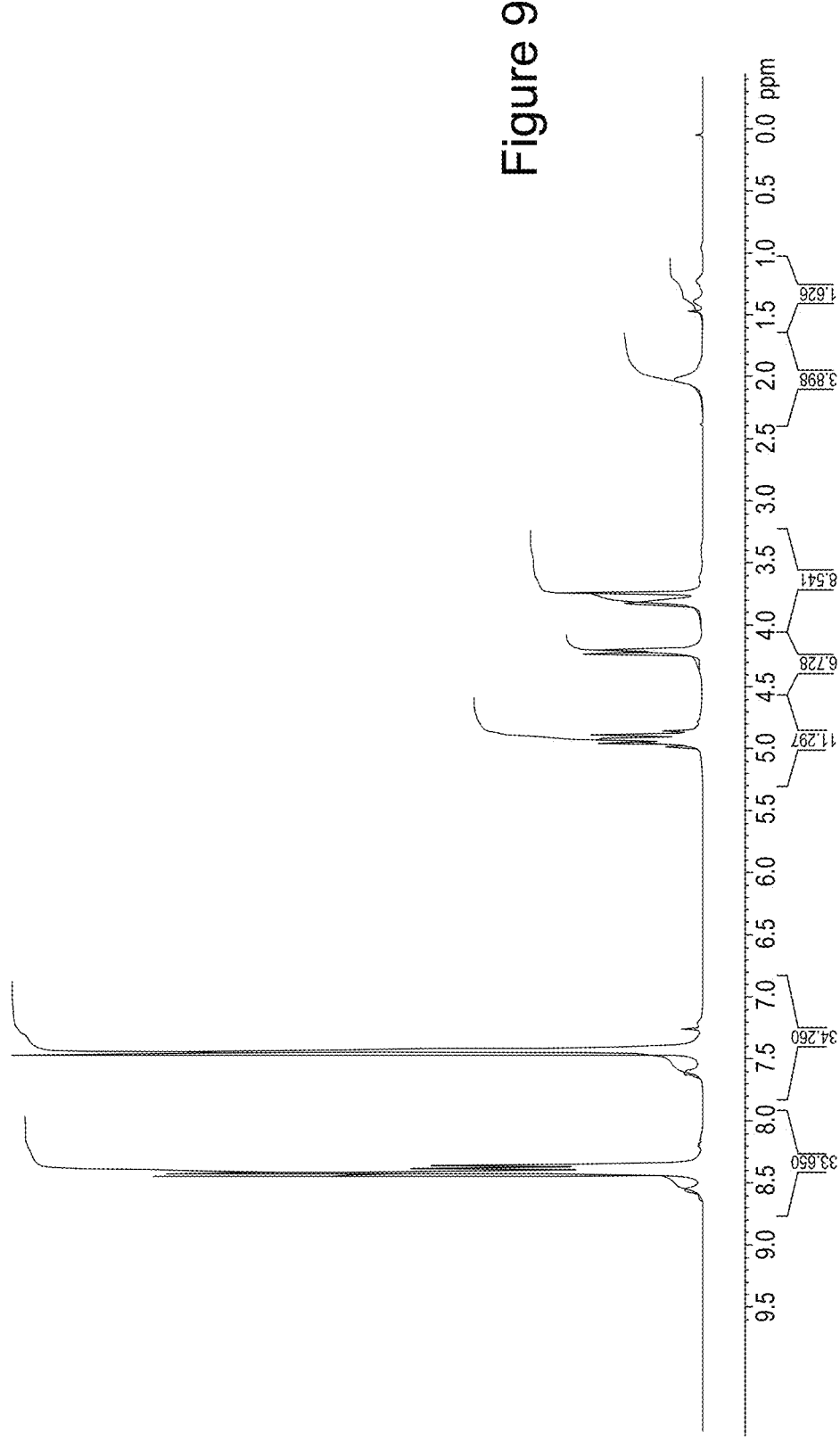
FIG. 9 is a $^1$H NMR spectrum of activated carbonate ester product (XV)

10.5 g of the alcohol product (XIII) from step 3 was placed in a 100 mL round bottom flask, equipped with a magnetic stirrer bar, sealed with a rubber seal and evacuated and refilled with nitrogen three times. Then 20 mL of anhydrous Novec™ 7100 were added by syringe followed by 2.8 mL of trimethylamine and 0.12 mL of pyridine. The solution was cooled in a water-ice bath and p-nitrophenylorthochloroformate in 10 mL of anhydrous tetrahydrofuran was slowly added by syringe. An off-white precipitate formed. The reaction was allowed to warm to room temperature and stirred for four days. The reaction was quenched with 50 mL of aqueous ammonium carbonate solution, the layers separated and the organic layer was extracted with a further 50 mL of aqueous ammonium carbonate. The fluorous layer was evaporated to dryness and purified by column chromatography. Yield of activated carbonate ester (XV) (clear oil): 6.15 g (54%). $^1$H NMR peaks at 4.95 (m), 7.4 (d) and 8.85 (d). The IR spectrum for the activated carbonate ester product (XV) is shown in FIG. 8. The $^1$H NMR spectrum for the activated carbonate ester product (XV) is shown in FIG. 9.

Step 5

Figure 10:
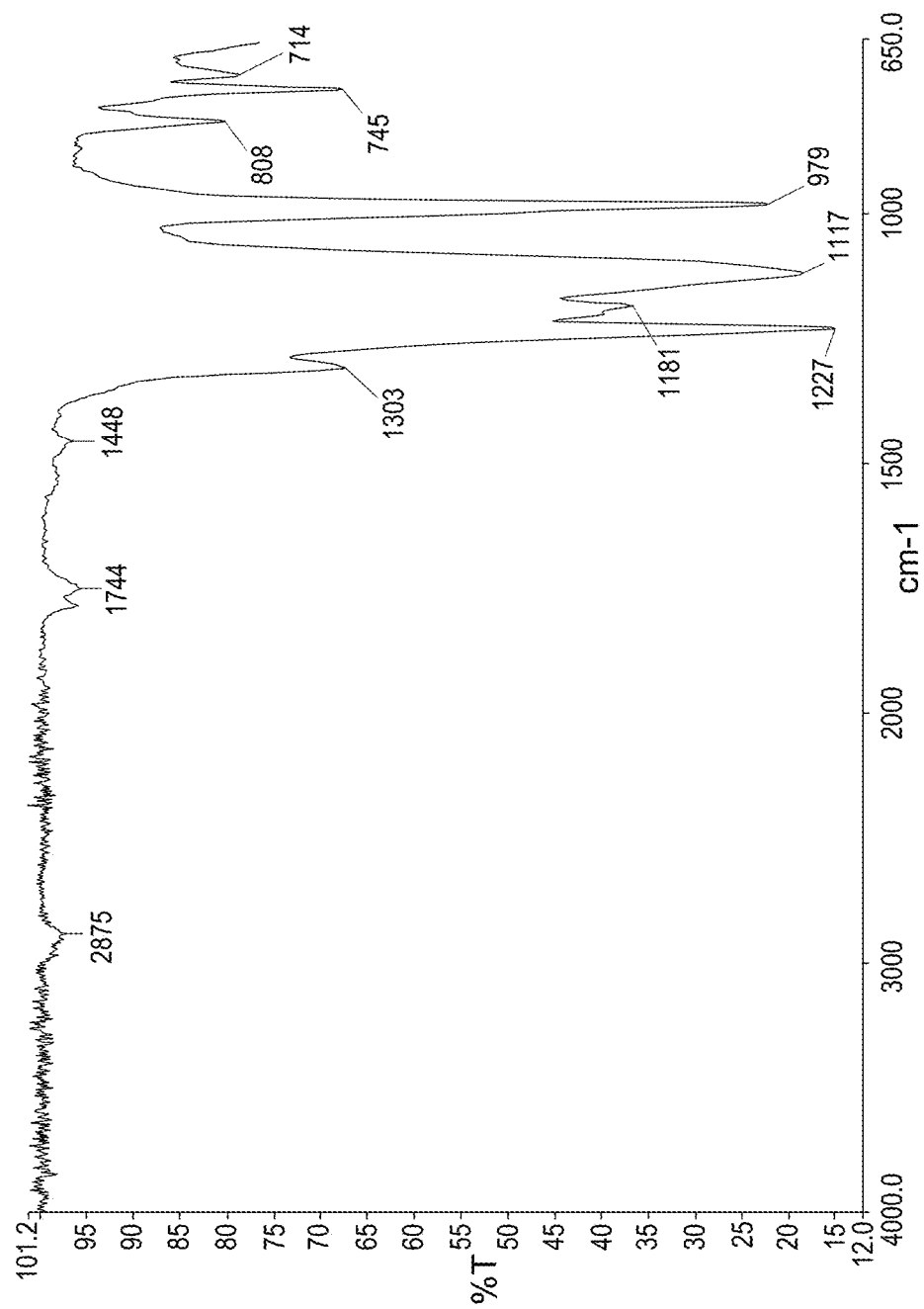
FIG. 10 is an IR spectrum of surfactant (IIb)
Figure 11:
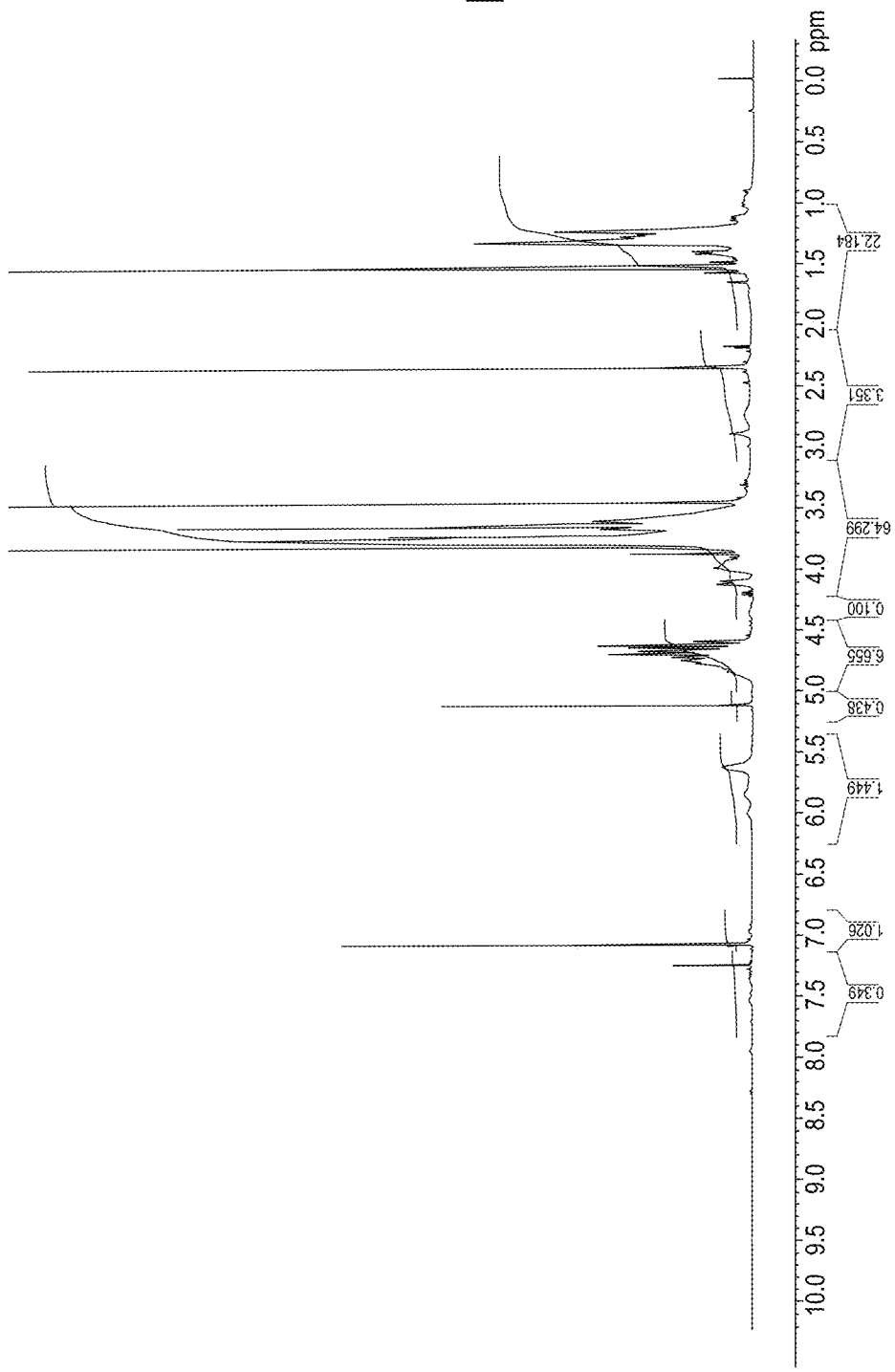
FIG. 11 is a $^1$H NMR spectrum of surfactant (IIb)

1.08 g of Jeffamine 900 was placed in a 100 mL round bottom flask. 6 g of the activated carbonate ester product (XV) from step 4 was dissolved in 15 mL of Novec™ 7100 and added to the Jeffamine. 1 g of polymer supported piperidine was added and the reaction was stirred at room temperature protected under nitrogen for three days. The polymer supported piperidine had coagulated/clumped and turned bright yellow. The reaction was filtered off and the clear filtrate was purified by column chromatography with 10% methanol in Novec™ 7100 as the eluent. Yield of surfactant (IIb) (yellow waxy solid): 2.84 g (42%). IR carbonyl stretch at 1743 cm$^{-1}$. The IR spectrum for the surfactant product (IIb) is shown in FIG. 10. The $^1$H NMR spectrum for the surfactant product (Mb) is shown in FIG. 11.

Example 3: Synthesis of Surfactant (IIc)

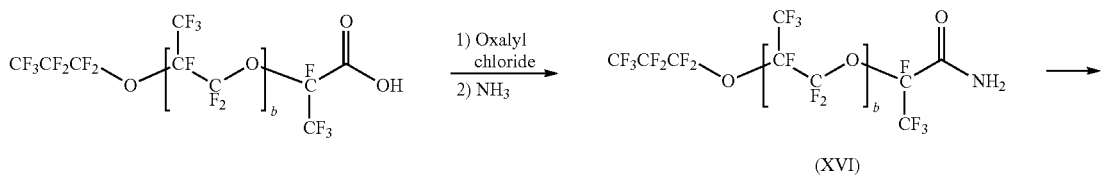

(XVI)

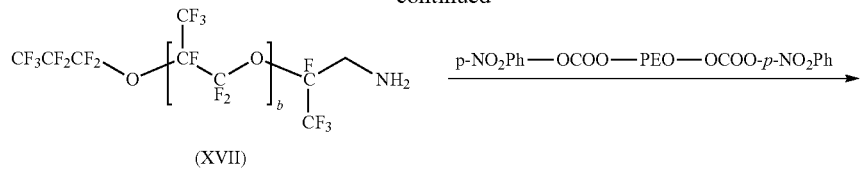

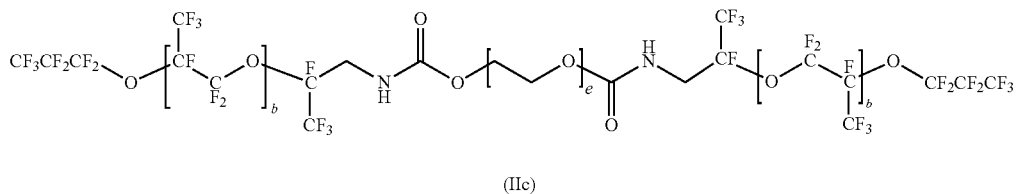

Step 1 was carried out in the same manner as for Example 1.

Step 2

Figure 12:
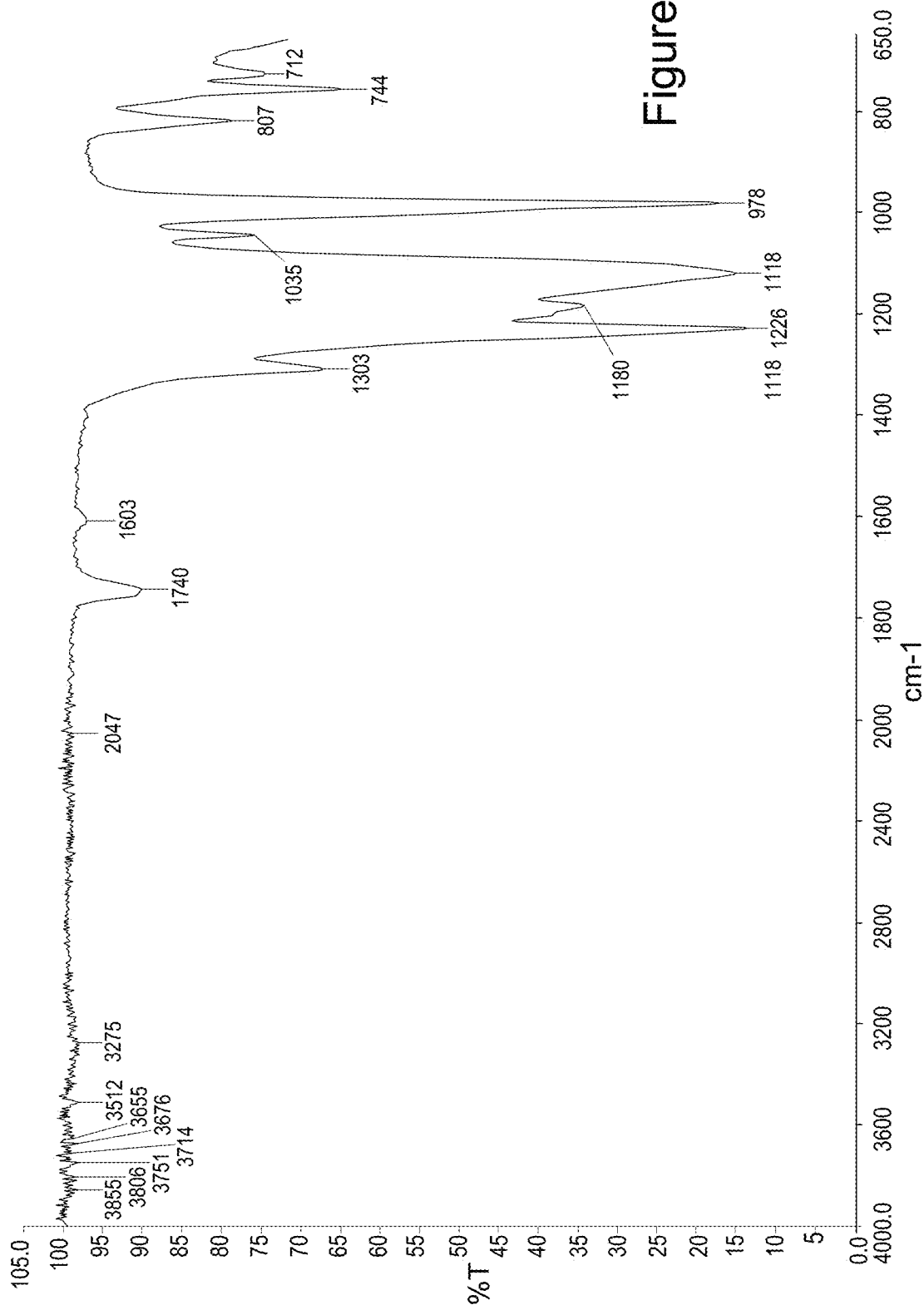
FIG. 12 is an IR spectrum of amide (XVI)
Figure 13:
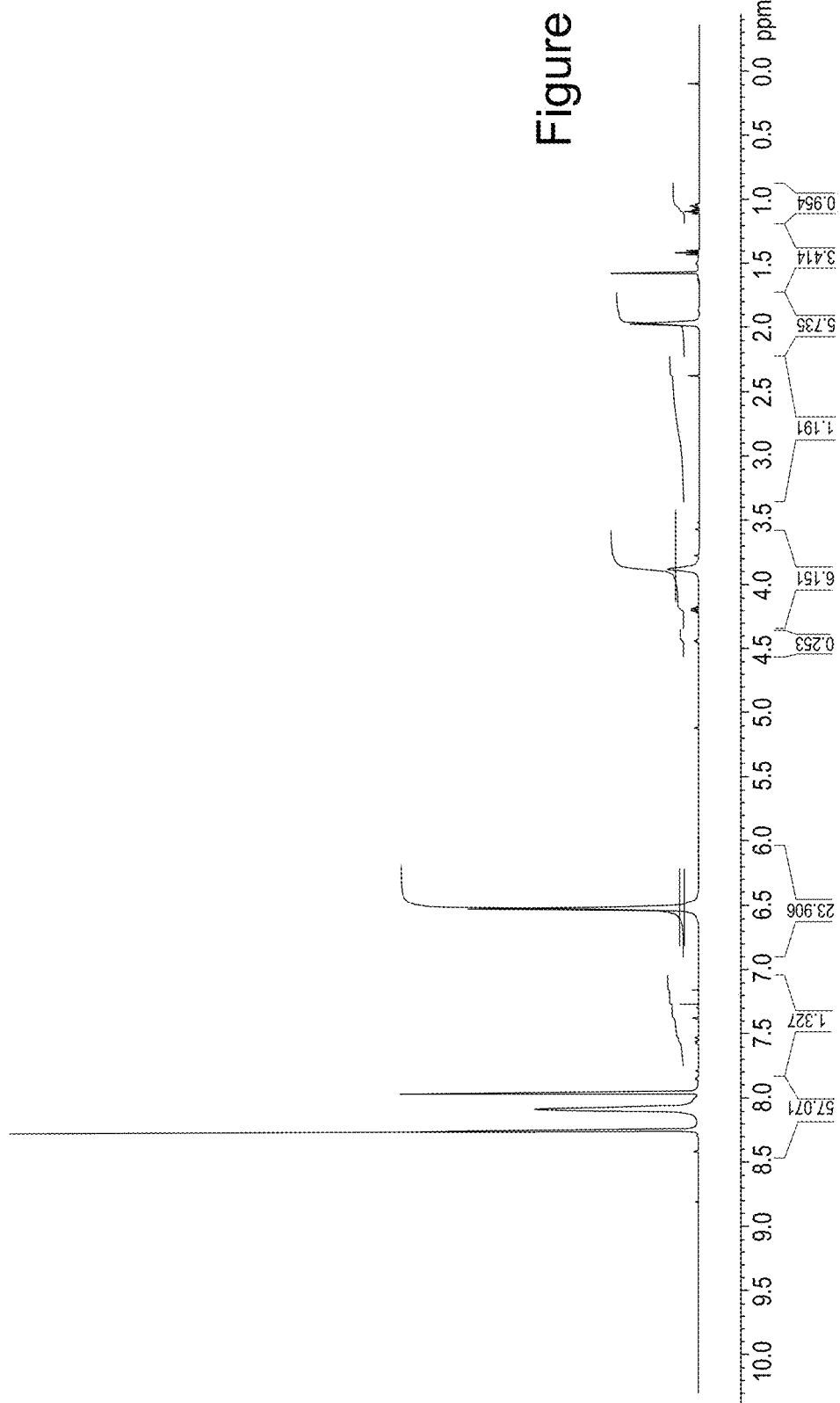
FIG. 13 is a $^1$H NMR spectrum of amide (XVI)

To a stirred solution of the acyl chloride product from step 1 (45.14 g; Mw=2329.5; 19.37 mmol) in Novec 7500 (50 mL), that was cooled to ~4° C. in an ice bath under $N_2$, was added ammonium hydroxide (48.5 mL, 7.989 M, 20 mol equivalents) via a syringe and the reaction mixture was stirred rapidly overnight. 50 mL methanol and 20 mL THF were added to the reaction solution with high speed stirring, and then the mixture was allowed to settle. The top layer (mainly a mixture of water/methanol/THF) was separated off and discarded. To the remaining bottom layer, was added 50 mL methanol and 20 mL THF again with high speed stirring, followed by evaporation to remove most of the volatile component. To the residue, was added 55 mL Novec 7100 and 20 mL methanol. The resultant solution was stirred at 700 rpm for 10 minutes. Then, the solution was allowed to settle in a separation funnel, and the top layer was separated and discarded. The collected fluorous phase was washed once more with 20 mL water and then dissolved in 50 mL methanol and 50 mL THF. The resultant clear solution was dried with anhydrous magnesium sulphate. After filtration, the filtrate solution was concentrated to dryness in vacuo giving amide product (XVI) as a colourless oil (yield: 47.537 grams, 98%). IR: 1740 $cm^{-1}$. The IR spectrum for the amide product (XVI) is shown in FIG. 12. The $^1H$ NMR spectrum for the amide product (XVI) is shown in FIG. 13.

Step 3

To solid $Fe_3(CO)_{12}$ (1.05 g) under nitrogen, was added anhydrous toluene (52 mL) at room temperature with stirring. To the resultant dark green solution (~0.04 M), was added a solution of the amide product (XVI) from step 2 (47.18 grams, Mw=2310, 20.42 mmol) in anhydrous Novec 7500 (92 mL) via a syringe, followed by addition of phenylsilane (10.08 mL, 81.7 mmol) using a separate syringe. The mixture was stirred at 132° C. (aluminium block temperature) for 2 days. On cooling to room temperature, a mixture of 15 mL methanol, 7 mL 5N HCl aqueous solution and 8 mL water were added portionwise into the reaction using a Pasteur pipette with stirring, followed by a mixture of 25 mL methanol and 25 mL 2N NaOH aq. solution, and finally 10 mL 2N NaOH. After stirring for a further 10 minutes, the resultant mixture was filtered over celite. The red aqueous top layer and fluorous bottom layer were separated in a separating funnel and the aqueous phase was back extracted with 50 mL Novec 7500. The combined organic phase was dried with anhydrous sodium sulphate. After filtration, it was concentrated in vacuo giving a yellow-brown oil, 43.4 grams. The concentrated residue was dissolved again in 80% Novec 7100/hexane (65 mL), and purified on an Interchim SiHC cartridge (220 g, 50 μm diameter spherical silica gel) and was eluted as follows: (1) 80% Novec 7100/Hexane (700 mL), (2) Novec 7100 (2000 mL), (3) 0.5% MeOH/Novec 7100 (800 mL) and finally (4) pure Novec7100 (1000 mL) consecutively.

Figure 14:
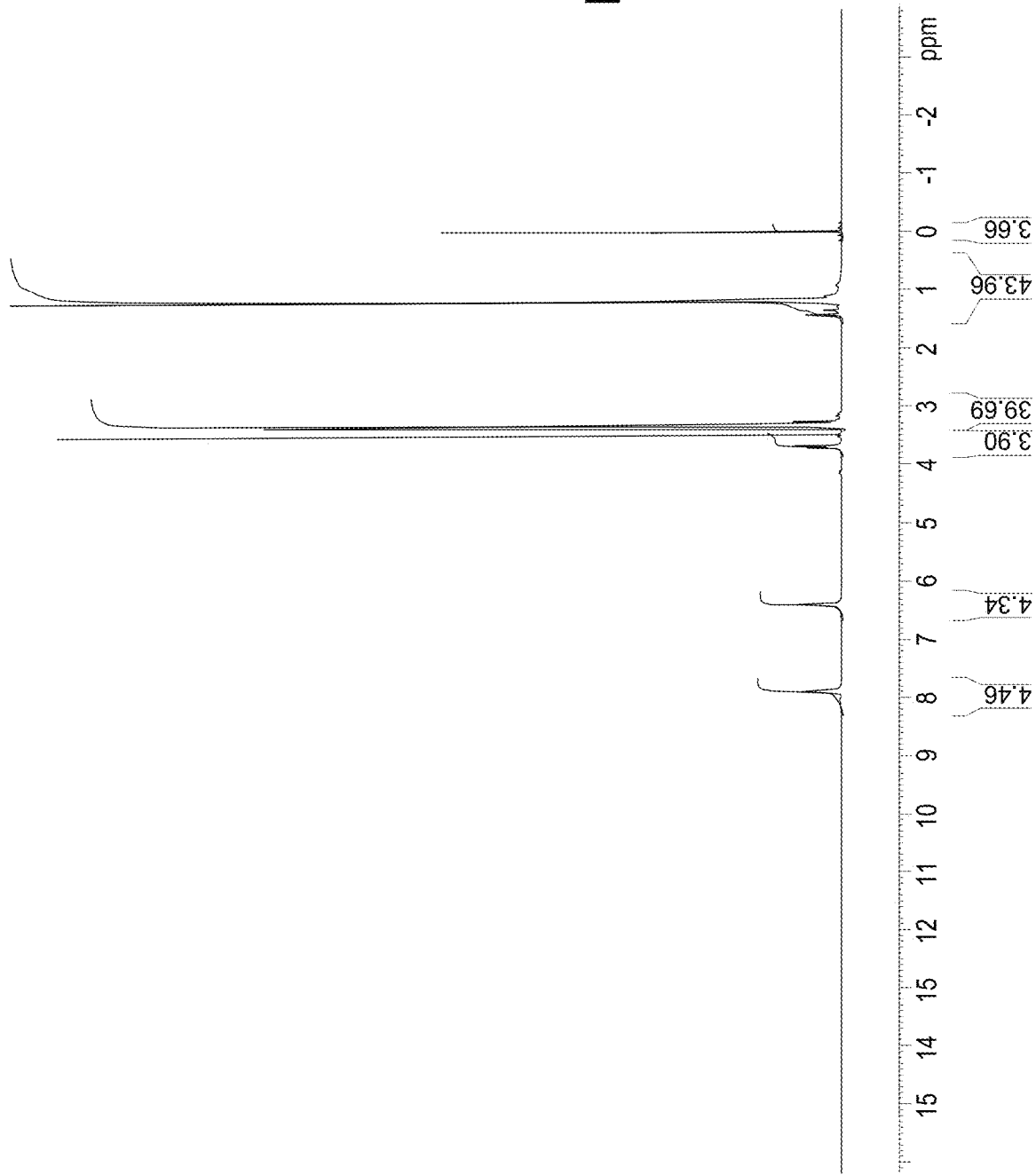
FIG. 14 is a $^1$H NMR spectrum of amine (XVII)

The product containing fractions were combined and concentrated in vacuo to give amine product (XVII) as a white hazy oil (yield: 26.908 grams, 57.37%). The $^1H$ NMR spectrum for the amine product (XVII) is shown in FIG. 14.

Step 4

To a stirred solution of the amine product (XVII) from step 3 (4.313 grams, Mw=2231, 1.933 mmol) in anhydrous Novec 7100 (8.0 mL) and THF (1.4 mL), was added Hunig's base (0.35 mL, 2.03 mmol) via syringe, followed by a warm solution of p-$NO_2$Ph-OCOO—PEO-OCOO-p-$NO_2$Ph (1 gram, Mn~1098, 0.91 mmol) in THF (7 mL) together with DBU (0.306 mL, 2.03 mmol). The mixture was then stirred at 40° C. for two days, and then evaporated to dryness. The residue was dissolved in in Novec7100 (50 mL), and the solution was treated with 4 g of 3-aminopropyl silica gel with gentle stirring for 10 minutes. After filtration of the solid, the filtrate was treated with another 2 g of 3-aminopropyl silica gel with gentle stirring for 10 minutes. The same procedure was repeated once more with 0.7 g of 3-aminopropyl silica gel. The final filtrate was concentrated in vacuo to dryness to give a pale yellow oil, which was purified on an Interchim SiHC cartridge (25 g, 50 μm diameter spherical silica gel). The cartridge was eluted as follows: (1) Novec 7100 (100 mL), (2) 3% MeOH/Novec 7100 (100 mL), (3) 6% MeOH/Novec 7100 (100 mL) and finally (4) 10% MeOH/Novec 7100 (300 mL) consecutively. The product containing fractions were combined and concentrated in vacuo to give carbamate product (IIc) as a white hazy oil (yield: 377 mg).

Example 4: Synthesis of Surfactant (IIg)

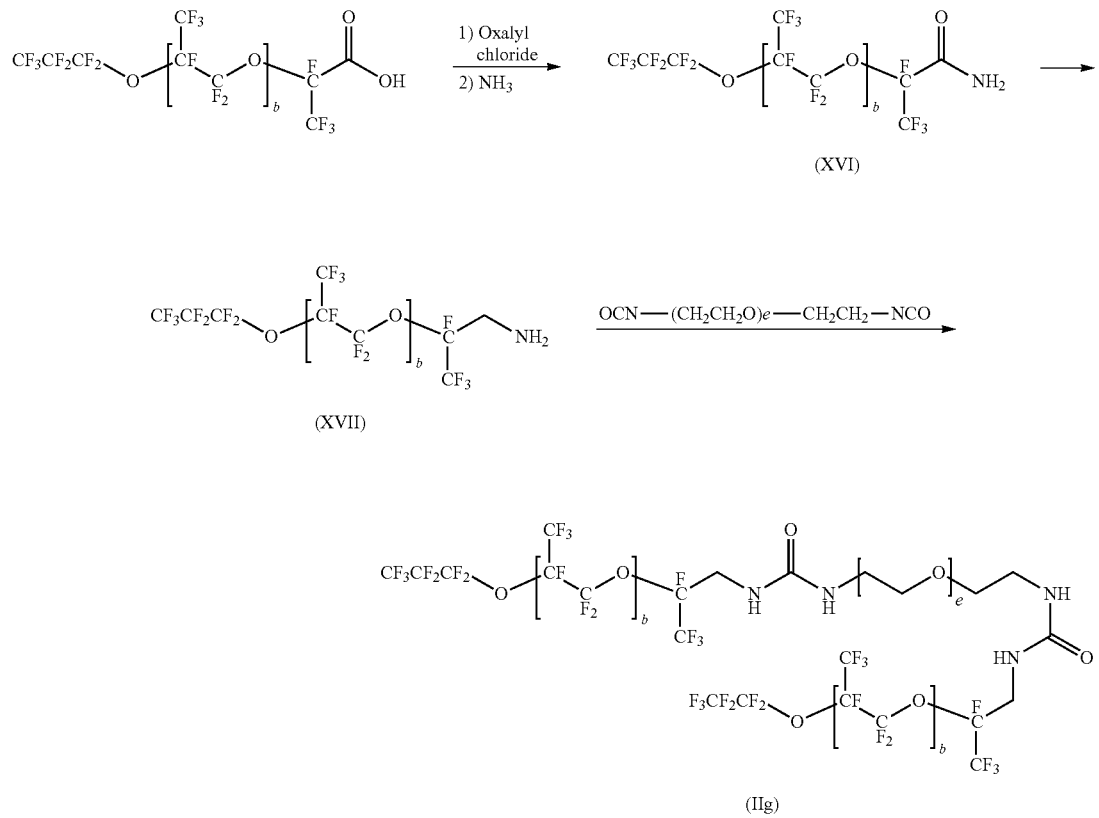

Steps 1 to 3 were carried out in the same manner as for Example 3.

Step 4

To a stirred solution of PEG-bis(isocyanate) (0.988 g, Mn~2000, 0.49 mmol) in anhydrous THF (10 mL) at 35° C., was added the amine product (XVII) from step 3 (4.536 grams, Mw=2231, 1.976 mmol) in Novec 7500 (7.5 mL) and followed by DBU (0.225 mL, 1.482 mmol). The resultant mixture was stirred at 35° C. overnight. Then to it, was added 3-aminopropyl silica gel (2.604 g) and Novec 7100 (5 mL). The suspension was gently stirred at room temperature for 20 minutes. After filtration of the solid, the filtrate was treated with another 1.06 g 3-aminopropyl silica gel with gentle stirring for further 10 minutes. The final filtrate was concentrated in vacuo to dryness to give a yellow oil, which was purified on an Interchim SiHC cartridge (25 g, 50 μm diameter spherical silica gel). The cartridge was eluted as follows: (1) Novec 7100 (100 mL), (2) 3% MeOH/Novec 7100 (100 mL), (3) 6% MeOH/Novec 7100 (100 mL) and finally (4) 10% MeOH/Novec 7100 (300 mL) consecutively. The product containing fractions were combined and concentrated in vacuo to give urea product (IIg) as a light yellow oil (yield: 477 mg).

Example 5: Synthesis of Surfactant (IIj)

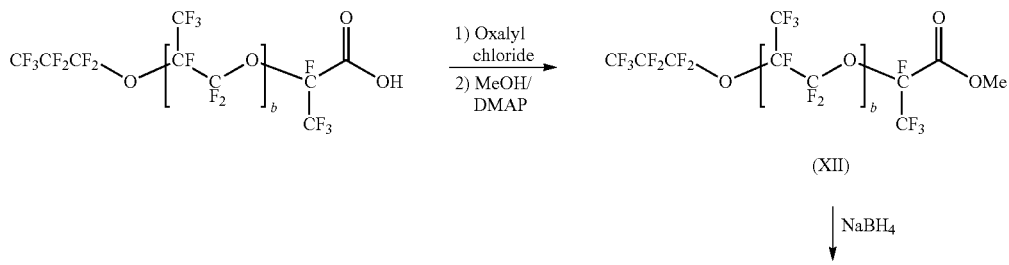

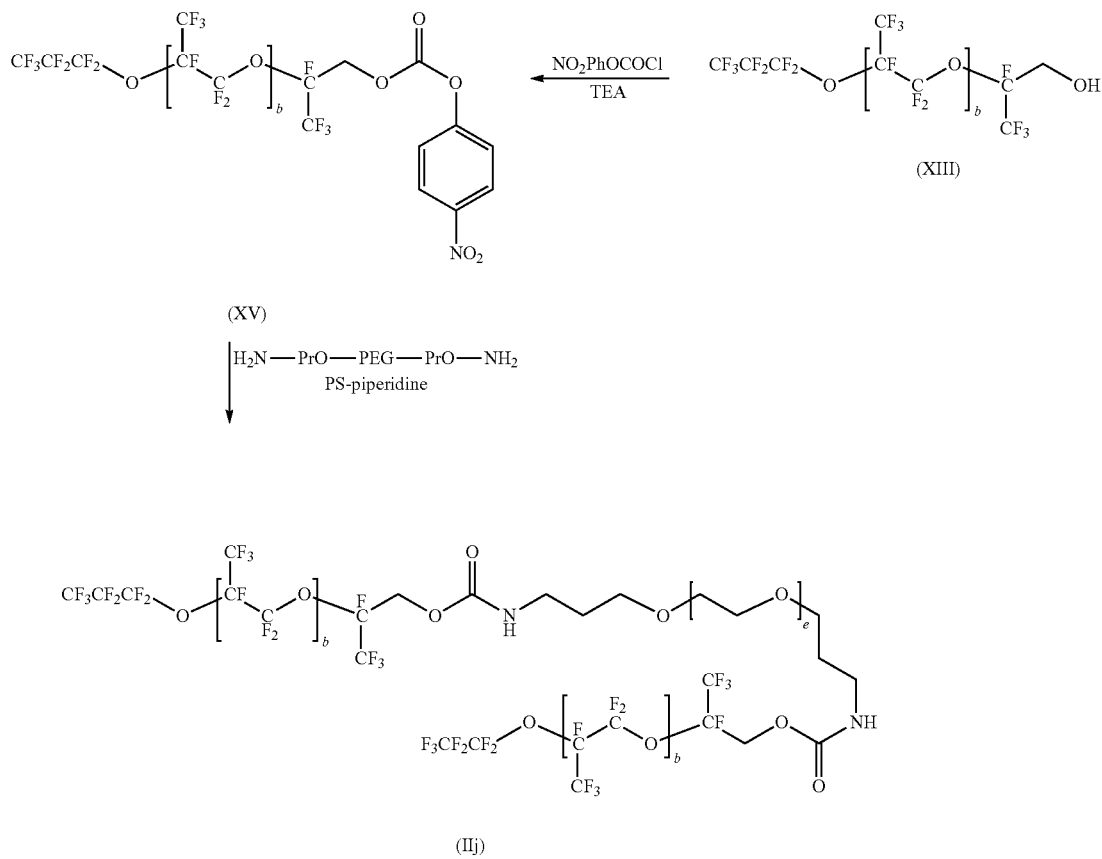

Steps 1 to 4 were carried out in the same manner as for Example 1 and Example 2.

Step 5

The activated Krytox carbonate ester product (XV), 38.09 grams, 15.47 mmol) from step 4 was placed in a 250 mL round bottom flask fitted with magnetic stirrer bar and 50 mL dropping funnel with septum. The apparatus was degassed by applying vacuum and refilled with nitrogen 3 times. Dry Novec 7100 (stored over anhydrous $Na_2SO_4$, 30 mL) was added by syringe to dissolve the activated carbonate ester, followed by anhydrous tetrahydrofuran (50 mL) by syringe. Poly(ethylene glycol) bis(3-aminopropyl) terminated (Mn~1500, 10.44 grams, 6.96 mmol) was dissolved in anhydrous tetrahydrofuran (25 mL) and dry Novec 7100 (stored over anhydrous $Na_2SO_4$, 15 mL) under nitrogen protection in a 100 mL round bottom flask fitted with septum. 4-Methylmorpholine (2.8 mL=2.58 grams, 23.21 mmol) was added by syringe to the poly(ethylene glycol) bis(3-aminopropyl) terminated solution. The solution with 4-methylmorpholine was then added to the dropping funnel and added slowly to the stirring activated Krytox carbonate ester over 30 minutes. The reaction was stirred at 35° C. heating block temperature for 17 hours. The reaction was then evaporated to dryness. The residue was re-dissolved in 200 mL of Novec 7100. 3-Aminopropyl functionalised silica gel (15 grams, 15 mmol) was added to the solution, stirred for 10 minutes and removed by filtration over a filter frit. Another 15 grams (15 mmol) of 3-aminopropyl functionalised silica gel was added four more times and removed by filtration over a frit. After the fifth aliquot of 3-aminopropyl functionalised silica gel, the mixture was filtered over Celite and filter paper under suction. The removal of 4-nitrophenol related impurities was complete when a small amount of 3-aminopropyl functionalised silica gel (20 mg) showed no traces of yellow when a few drops of the filtrate were added. The clear filtrate was evaporated to dryness on a rotary evaporator (40° C., 270 mbar, then 50° C., 0-5 mbar) to an opaque, colourless oily wax (15 g). The waxy residue was dissolved in 50 mL of Novec 7100.

Figure 15:
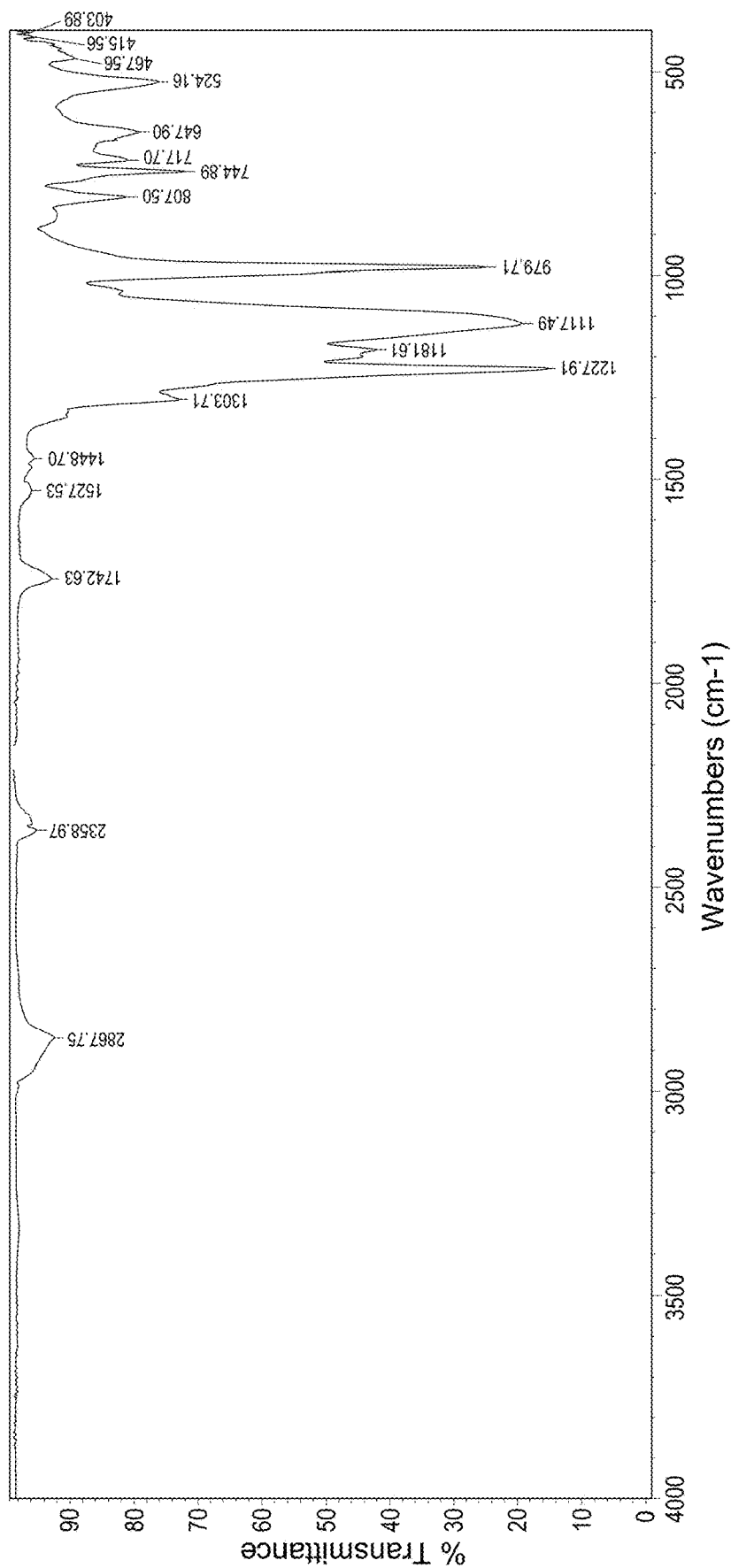
FIG. 15 is an IR spectrum of surfactant (IIj)
Figure 16:
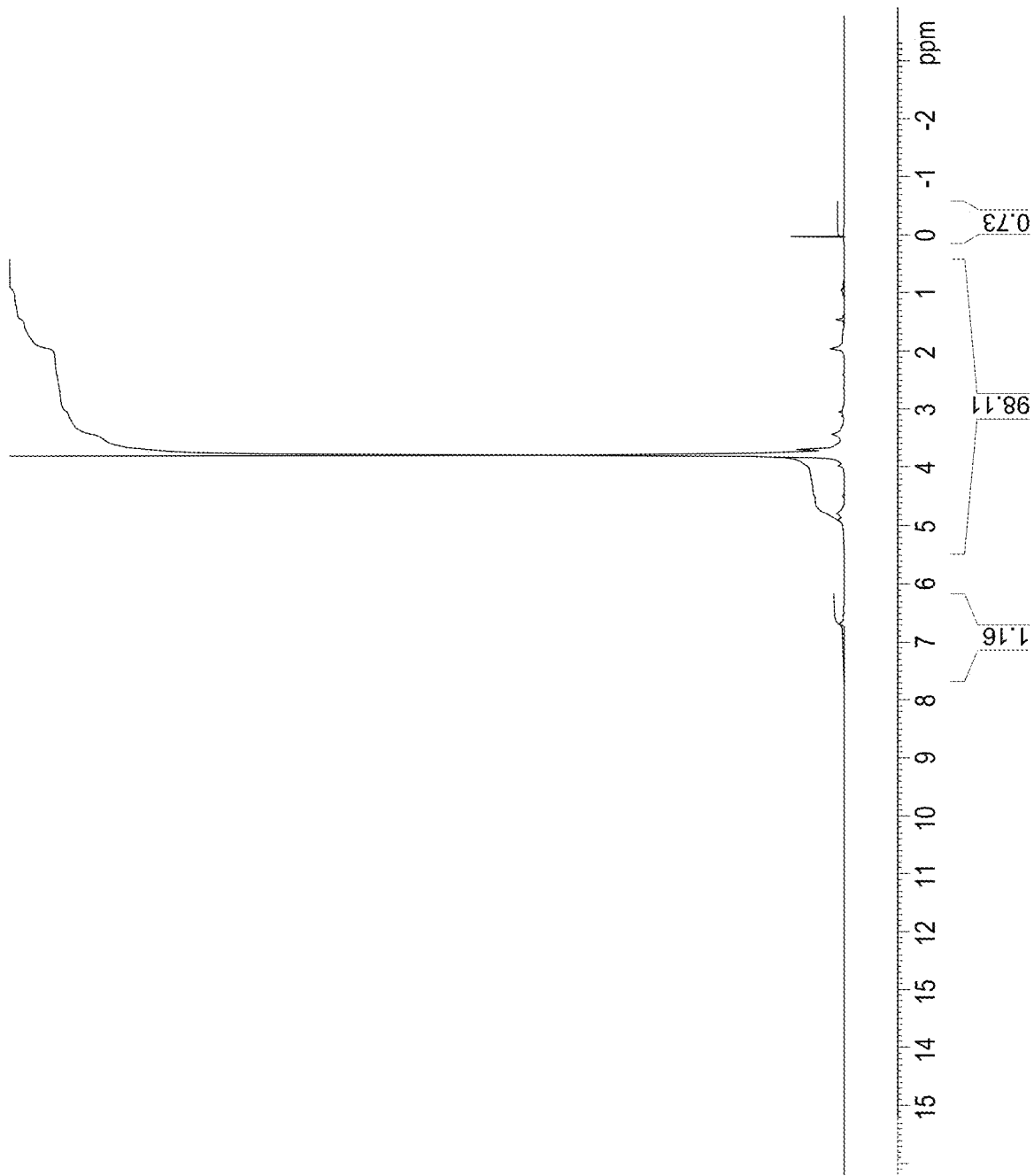
FIG. 16 is a $^1$H NMR spectrum of surfactant (IIj)

A flash chromatography cartridge (Puriflash HC Spherical Silica, 50 um, 25 g) was primed with 100 mL Novec 7100 (p=8 psi). The solution of crude surfactant was applied by syringe. The column was eluted using 100 ml of neat Novec 7100, then 100 mL of 5% methanol in Novec 7100 and finally 300 mL of 10% methanol in Novec 7100. Ten fractions of 50 mL each were collected. Fractions 6-8 were combined and evaporated to dryness on a rotary evaporator (40° C., 270 mbar, then 70° C., 0-5 mbar) to yield a clear waxy solid IIj (total yield: 3.863 grams, 9%). The IR spectrum for the surfactant product (IIj) is shown in FIG. 15. The $^1$H NMR spectrum for the surfactant product (IIj) is shown in FIG. 16.

Example 6: Proposed Synthesis of Surfactant (IIh)

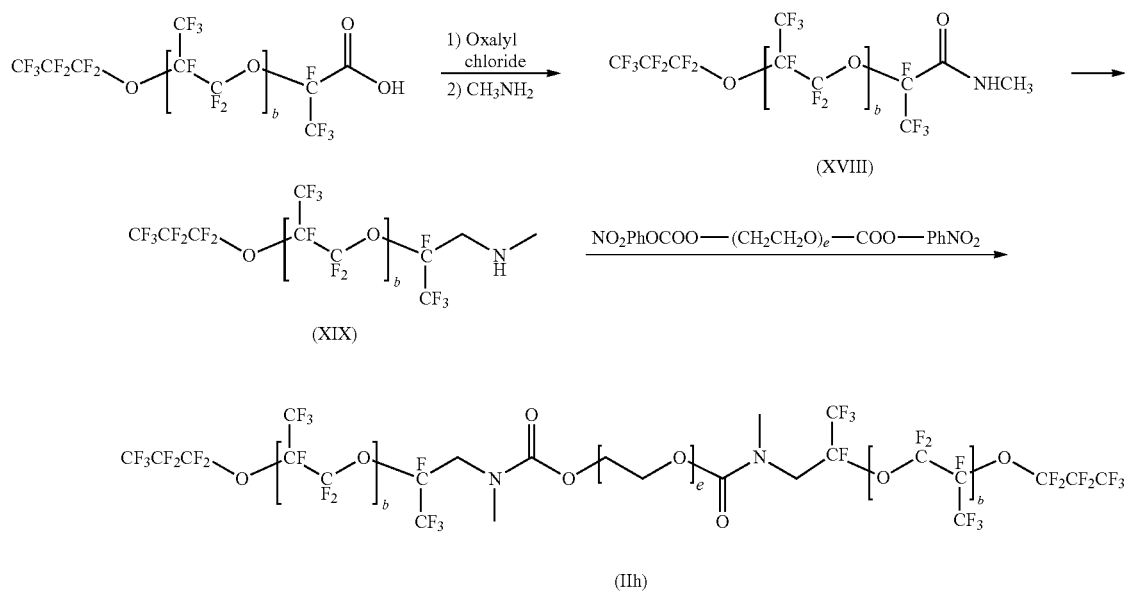

Step 1 is carried out in the same manner as for Example 1.

Step 2

To a stirred solution of the acyl chloride product from step 1 in Novec 7100 that is cooled in an ice bath, is added a cool aqueous solution of methylamine. The reaction mixture is then allowed to warm to room temperature, and stirring continued overnight. The reaction solution is mixed with saturated brine, and the mixture filtered. The water layer is separated off and the organic fraction dried with anhydrous sodium sulphate, filtered and concentrated in vacuo giving an oil, which was dissolved in FC72. The mixture is filtered through celite and concentrated in vacuo to give amide product (XVIII).

Step 3

To solid $Fe_3(CO)_{12}$ under nitrogen, is added anhydrous toluene at room temperature with stirring. To the resultant dark green solution is added a solution of the amide product (XVIII) from step 2 in anhydrous Novec 7500, followed by addition of phenylsilane. The mixture is stirred at 130° C. (aluminium block temperature) for 2 days. On cooling to room temperature, methanol and HCl aq. solution are added into the reaction. The resultant solid is filtered off, and washed with Novec 7100. The aqueous phase and fluorous layer are then separated and the aqueous phase back extracted with Novec 7100. The combined organic phase is dried with anhydrous sodium sulphate, filtered and concentrated in vacuo giving an oil, which is dissolved in a mixture of hexane and Novec 7100. The mixture is purified on an Interchim SiHC cartridge (25 g, 15 μm diameter spherical silica gel) to give amine product (XIX).

Step 4

To a stirred solution of the amine product (XIX) from step 3 in anhydrous Novec 7100 and THF, is added Hunig's base followed by a warm solution of $NO_2PhOCOO$—$(CH_2CH_2O)_eCO_2PhNO_2$ in THF together with DBU. The mixture is then stirred at 40° C. for two days, and evaporated to dryness. The residue is dissolved in in Novec7100 and the solution is treated with 3-aminopropyl silica gel with gentle stirring. The mixture is filtered and the filtrate concentrated in vacuo. The resultant residue is purified on an Interchim SiHC cartridge to give carbamate product (IIh).

Example 7: Proposed Synthesis of Surfactant (IIi)

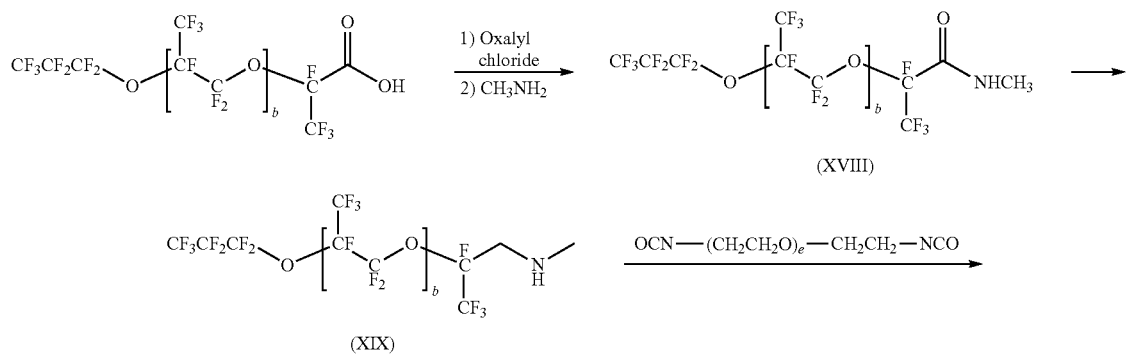

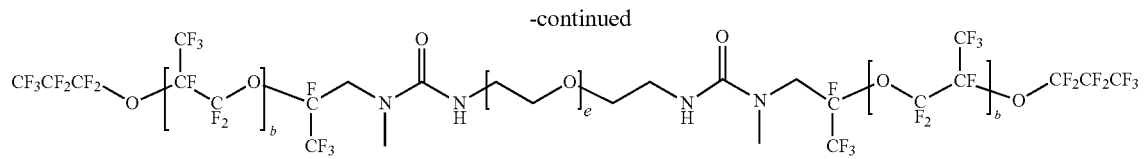

(IIi)

Steps 1 to 3 are carried out in the same manner as for Example 6.

Step 4

To a stirred solution of PEG-bis(isocyanate) in anhydrous THF at 35° C., is added the amine product (XIX) from step 3 in Novec 7500, followed by DBU. The resultant mixture is stirred at 35° C. overnight then 3-aminopropyl silica gel and Novec 7100 is added. The mixture is stirred at room temperature and then filtered. The filtrate is concentrated in vacuo and the residue purified on an Interchim SiHC cartridge to give urea product (IIi).

Example 8: Proposed Synthesis of Surfactant (IId)

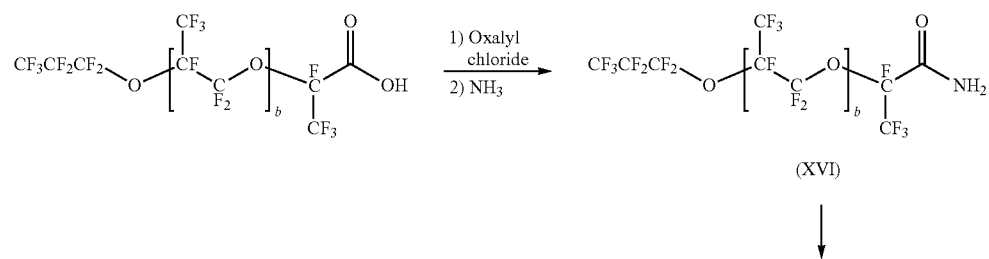

(XVI)

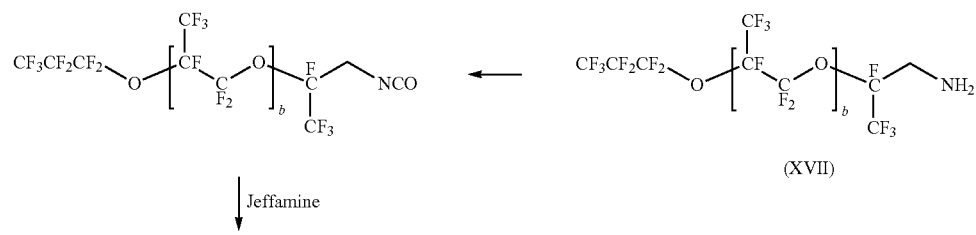

(XVII)

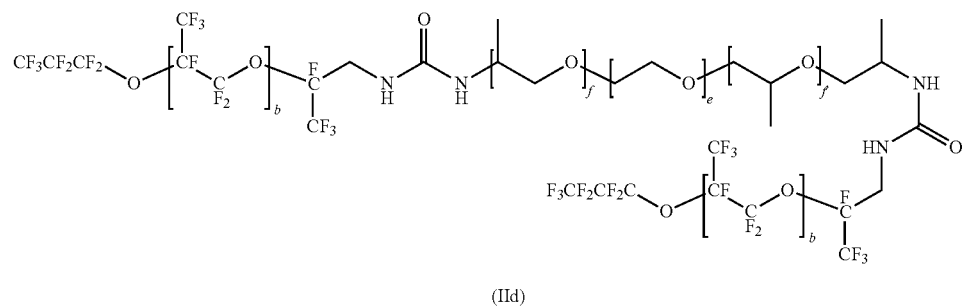

(IId)

Steps 1 to 3 are carried out in the same manner as for Example 3.

Step 4

The amine product from step 3 is converted to the corresponding isocyanate.

Step 5

The isocyanate product from step 4 is reacted with Jeffamine 900 to provide the surfactant product (IId).

Example 9: Proposed Synthesis of Surfactant (IIe)

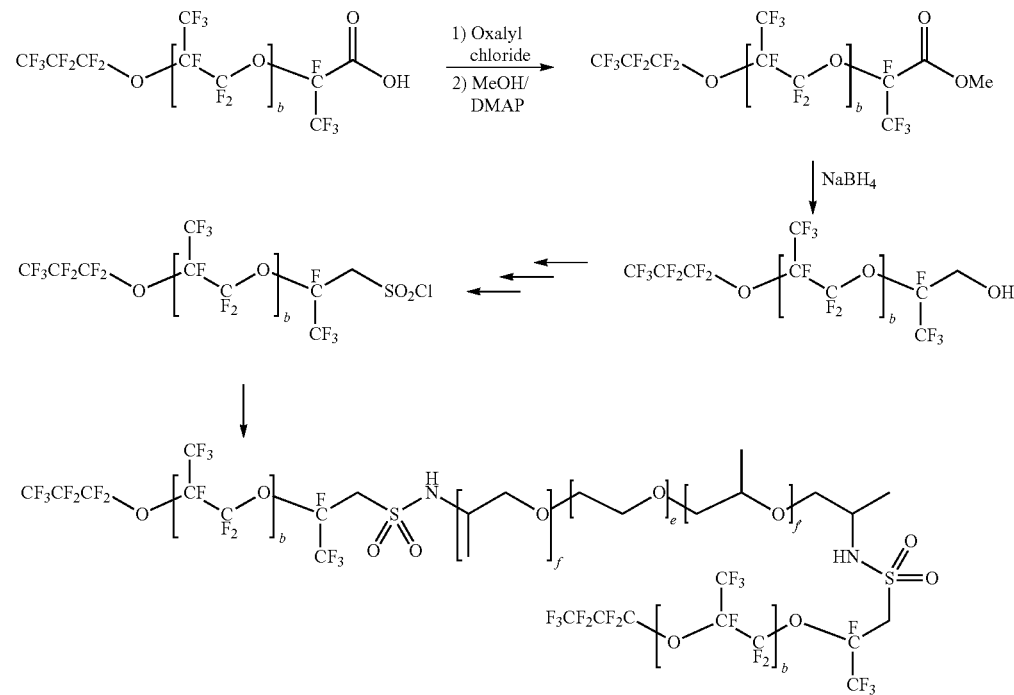

Steps 1 to 3 are carried out in the same manner as for Example 1.

Step 4

The alcohol product from step 3 is converted to the sulfonyl chloride.

Step 5

The sulfonyl chloride product from step 4 is reacted with Jeffamine 900 to provide the surfactant product (IIe).

Example 10: Proposed Synthesis of Surfactant (IIf)

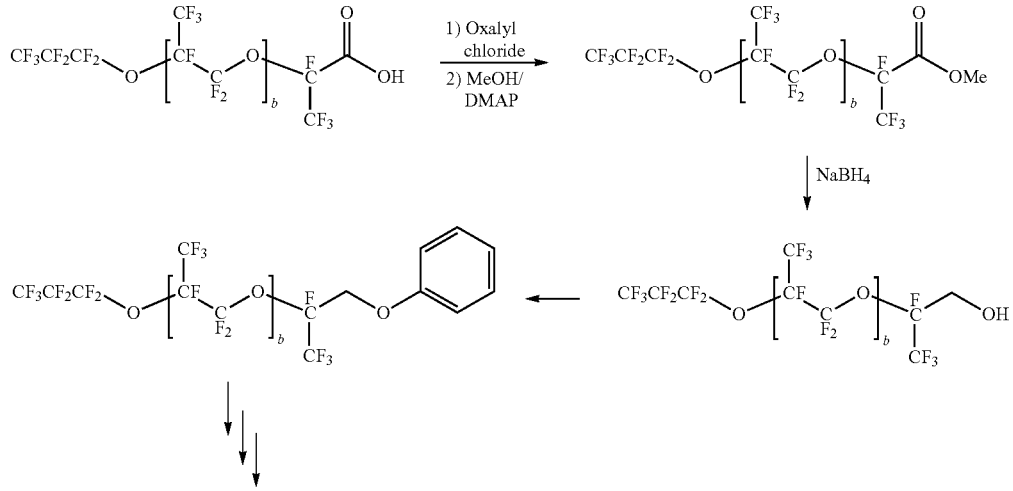

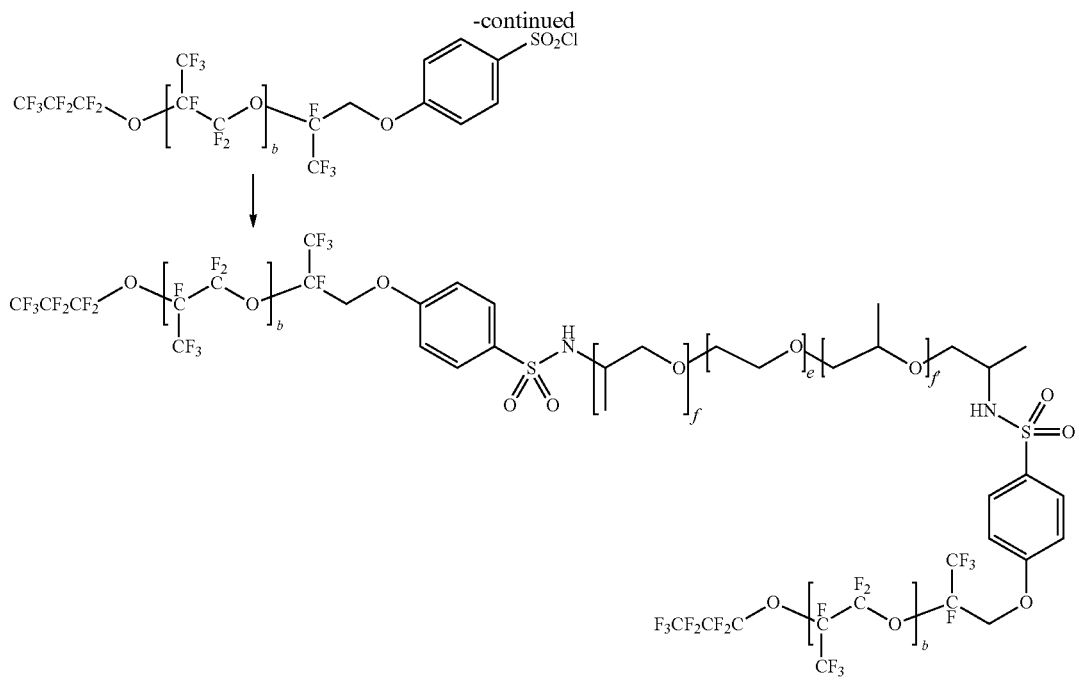

Steps 1 to 3 are carried out in the same manner as for Example 1.

Step 4

The alcohol product from step 3 is converted to the corresponding phenyl ether.

Step 5

The phenyl ether product from step 4 is converted to the sulfonyl chloride.

Step 6

The sulfonyl chloride product from step 5 is reacted with Jeffamine 900 to provide the surfactant product (IIf).

Example 11: Emulsion Generation Using Surfactants

Figure 17:
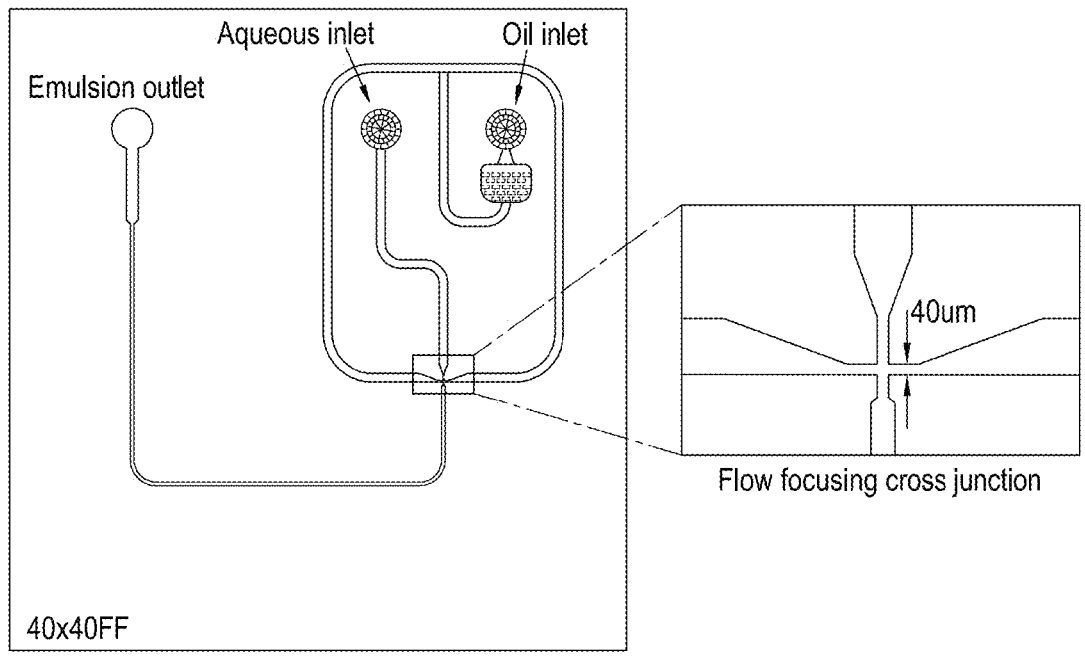
FIG. 17 is a diagrammatic illustration of a polydimethylsiloxane (PDMS) biochip with a flow focusing cross junction nozzle of 40 µm×40 µm.

Emulsion droplets were generated on a polydimethylsiloxane (PDMS) Pico-Gen™ biochip (Sphere Fluidics Limited) with a flow focusing cross junction nozzle of 40 μm×40 μm. This biochip is illustrated diagrammatically in FIG. 17 which shows the emulsion outlet (1) (at the top left of the diagram), aqueous inlet (2) (indicated by the left hand side arrow in the main diagram), oil inlet (3) (indicated by the right hand side arrow in the main diagram) and flow focusing cross junction (4) (indicated by the arrows in the magnified inset).

Novec™ 7500 was used as the continuous oil phase and polymerase chain reaction (PCR) mix solution (see below table) was used as the aqueous phase. 5% (w/w) of purified surfactant (IIa) from Example 1 or surfactant (IIb) from Example 2 was dissolved in the continuous oil phase prior to mixing of the oil and aqueous phases in the microfluidic device. Table 1 shows the composition of the PCR mix solution.

PCR Mix Solution

Platinum® Taq DNA Polymerase kit (Life Technologies, #10966)

Jurkat genomic DNA sample (Thermo Fisher Scientific, #SD1111)

ACTB primer set (Jena Bioscience GmbH, #PCR-253)

dNTP Mix, 10 mM each (Thermo Fisher Scientific, #R0191)

Nuclease-free Water, 50 mL (Life Technologies, #AM9937)

TABLE 1

| Reagent | Volume (μL) | Final Concentration | |
|---|---|---|---|
| Nuclease-free Water | 435.6 | n/a | |
| Platinum Taq buffer | 60 | n/a | |
| MgCl$_2$ | 18 | 1.5 | mM |
| dNTP (10 mM) | 12 | 0.2 | mM |
| Primers | 12 | 0.3 | μM |
| DNA sample | 60 | 3.65 | ng/μL |
| Platinum Taq enzyme | 2.4 | 0.4 | unit/50 μL |
| Master mix volume | 600 | n/a | |

Figure 18:
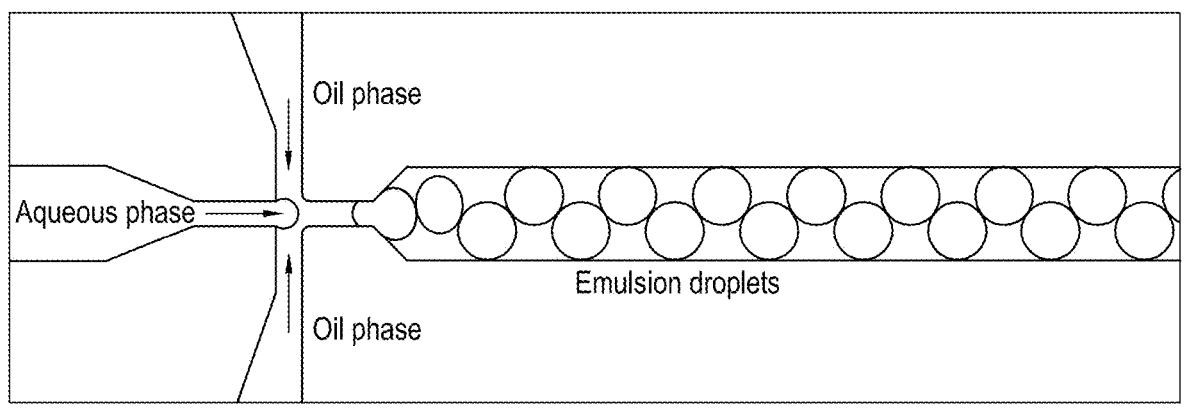
FIG. 18 is a microscope image of emulsion droplets generated on a polydimethylsiloxane (PDMS) biochip with a flow focusing cross junction nozzle of 40 µm×40 µm.

The oil flow rate was 300 μL/hr and the aqueous flow rate was 300 μL/hr. Droplet generation frequency was about 1,000 Hz, and droplet volume was around 80-87 pL (53.5-55 μm in diameter). FIG. 18 shows droplets (5) generated at the flow focusing junction (4) where an oil phase (6) (indicated by the vertical arrows) and an aqueous phase (7) (indicated by the horizontal arrow) meet. The droplets are stable within the microfluidic channel.

This demonstrates the successful formation of an emulsion comprising surfactant (IIa) or (IIb) within a microfluidic device. The droplets formed are stable within the microfluidic channel, showing that the surfactants successfully stabilised the droplets, preventing coalescence.

Example 12: Emulsion PCR

The droplet emulsion samples generated in Example 11 using surfactant (IIa) and surfactant (IIb) were each placed in a G-Strom Thermal Cycler System (Labtech.com), and the thermal cycle program shown in Table 2 was run.

TABLE 2

| Temperature | Time | # Cycles |
|---|---|---|
| 95° C. | 2 min | 1 |
| 95° C. | 30 sec | 35 |
| 59° C. | 30 sec | |
| 72° C. | 30 sec | |
| 72° C. | 2 min | 1 |
| 4° C. | ∞ | ∞ |

Figure 19:
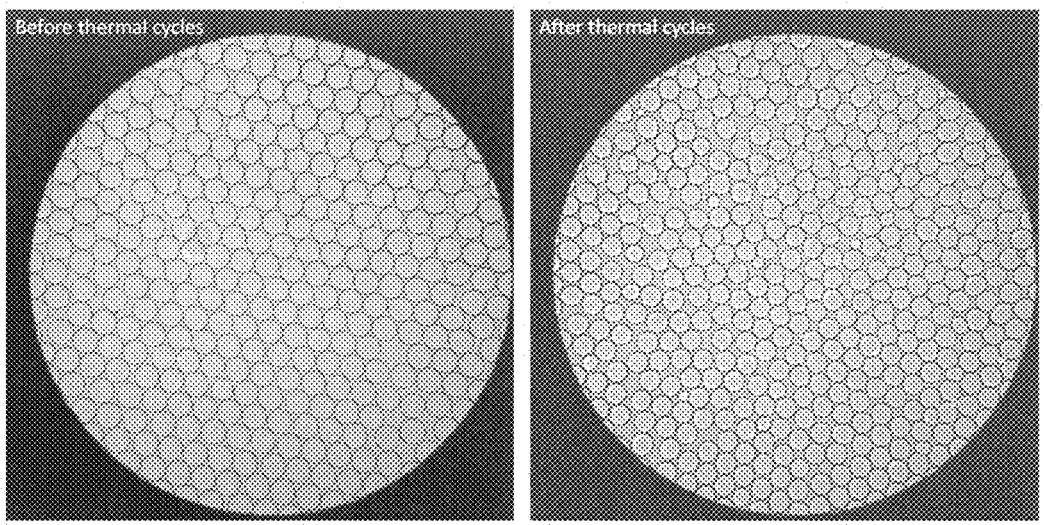
FIG. 19 shows microscope images of a droplet emulsion sample comprising surfactant (IIa) taken before (left hand image) and after (right hand image) PCR thermal cycles.
Figure 20:
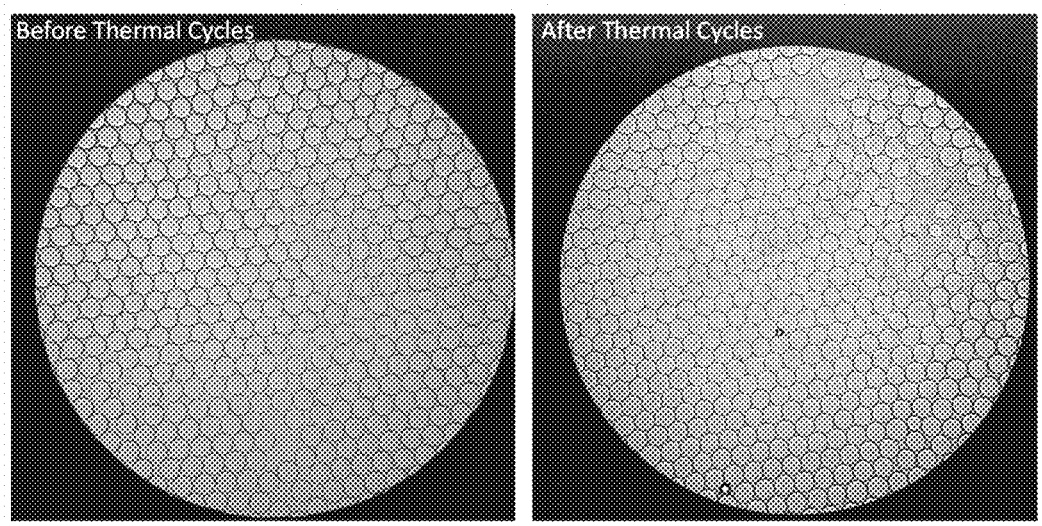
FIG. 20 shows microscope images of a droplet emulsion sample comprising surfactant (IIb) taken before (left hand image) and after (right hand image) PCR thermal cycles.

Droplet images were taken under a Zeiss microscope with a Mikrotron Hi-Speed camera before and after the PCR thermal cycles. FIG. 19 shows microscope images of the droplet emulsion sample comprising surfactant (IIa) before (left hand side image) and after (right hand side image) the PCR thermal cycles were run. FIG. 20 shows microscope images of the droplet emulsion sample comprising surfactant (IIb) before (left hand side image) and after (right hand side image) the PCR thermal cycles were run. The images show that the surfactant (IIa) and surfactant (IIb) were each functionally active by stabilising the droplets and stopping coalescence even during thermal cycles.

The PCR product was then analysed with standard agarose gel DNA electrophoresis. Emulsion PCR was also run analogously using the commercially available fluorous surfactant Pico-Surf™ 1 (Sphere Fluidics Limited) in place of surfactant (IIa) or (IIb) in the droplet emulsion, and the product used as a positive control in the electrophoresis analysis.

Figure 21:
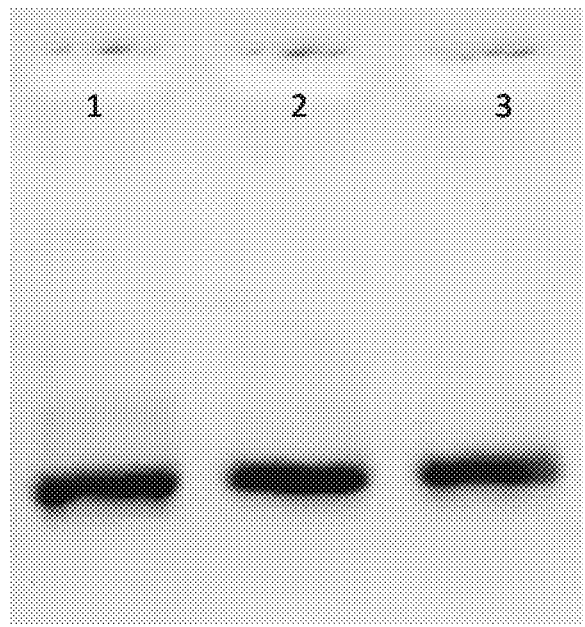
FIG. 21 shows an electrophoresis analysis of emulsion PCR product resulting from the droplet emulsion sample comprising surfactant (IIa)

FIG. 21 shows the electrophoresis result for the emulsion PCR product resulting from the droplet emulsion sample comprising surfactant (IIa). In FIG. 21, Lane 1: PCR product in bulk; Lane 2: PCR product in emulsion stabilized with Pico-Surf™ 1; and Lane 3: PCR product in emulsion stabilized with surfactant (IIa). This shows that the PCR product in the surfactant (IIa) stabilized droplet emulsion gives a clear product band as bright as that of the PCR product from the Pico-Surf™ 1 stabilized droplet emulsion.

Figure 22:
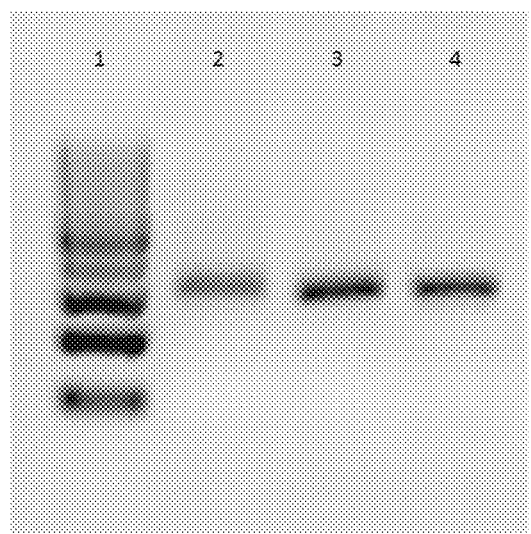
FIG. 22 shows an electrophoresis analysis of emulsion PCR product resulting from the droplet emulsion sample comprising surfactant (IIb)

FIG. 22 shows the electrophoresis result for the emulsion PCR product resulting from the droplet emulsion sample comprising surfactant (IIb). In FIG. 22, Lane 1: molecule ladder; Lane 2: PCR product in bulk; Lane 3: PCR product in emulsion stabilized with Pico-Surf™ 1; and Lane 4: PCR product in emulsion stabilized with surfactant (IIb). This shows that the PCR product in the surfactant (IIb) stabilized droplet emulsion gives a clear product band as bright as that of the PCR product from the Pico-Surf™ 1 stabilized droplet emulsion.

Example 13: Cell Viability in Surfactant Stabilized Emulsions $1.2 \times 10^6$ Chinese hamster ovary (CHO) cells from a suspension culture were pelleted (300×g, 5 min), re-suspended in 1 mL encapsulation media (CHO cell growth media, 16% OptiPrep™, 1% Pluronic® F-68) and passed through a 30 μm CeliTrics® cell strainer. Cells were encapsulated in 300 μL droplets using 5% (w/w) surfactant (IIa), surfactant (IIb) or Pico-Surf™ 1 in Novec™ 7500. 200 μL of emulsion was collected for each sample and after collection placed in a 37° C. $CO_2$ incubator for 2 hr before being processed. Non-encapsulated CHO cells were kept in parallel as a viability control.

In order to assess viability, samples were de-emulsified by mixing with an equal volume of Pico-Break™ (Sphere Fluidics Limited), followed by transferring 100 μL of the aqueous phase (containing CHO cells) into a fresh 1.5 mL reaction tube. 5 μL of Solution 18 (AO•DAPI, Chemometec, #910-3018) were added to the cells, mixed, and 10 μL of each sample was loaded in a chamber of an NC-Slide A8™ (Chemometec, #942-0003). Non-encapsulated CHO cells (100 μL) were directly mixed with 5 μL of Solution 18 prior to loading on an NC-Slide A8™. Cell viability was determined using the Viability and Cell Count Assay program on a NucleoCounter® NC-250™ instrument.

Figure 23A:
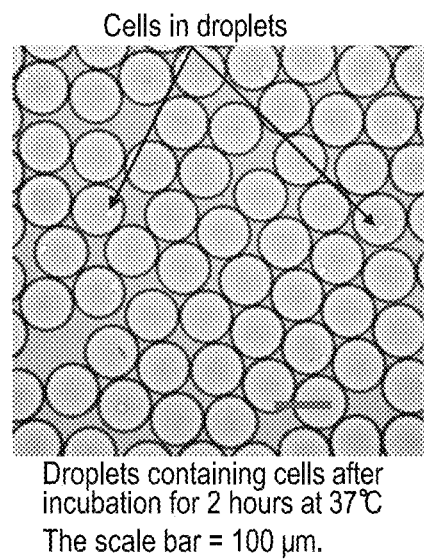
FIG. 23*a* is a microscope image of surfactant (IIa) stabilized droplets containing cells after incubation for 2 hours at 37° C.
Figure 23B:
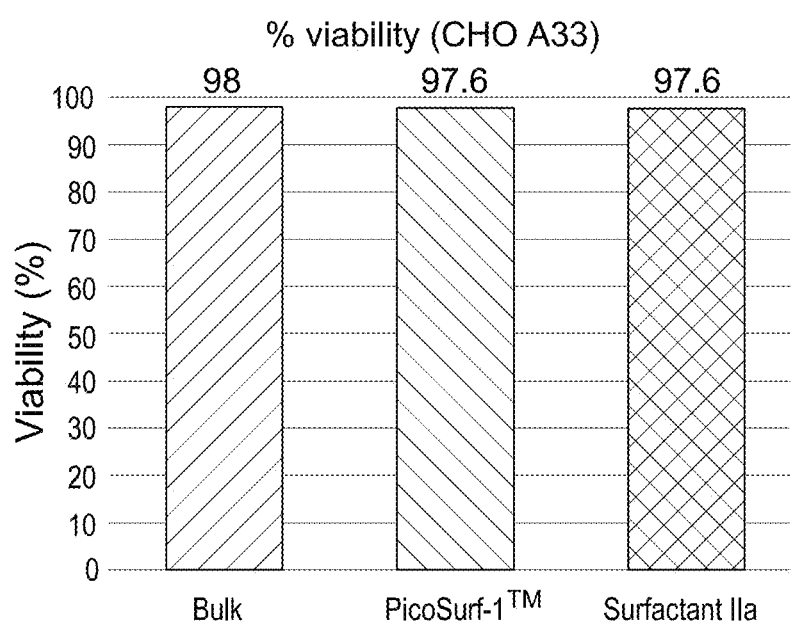
FIG. 23*b* is a bar graph showing the percentage of viable cells in surfactant (IIa) stabilized droplets containing cells after incubation for 2 hours at 37° C.

FIG. 23 shows the results of the cell viability study for cells encapsulated in droplets using surfactant (IIa). FIG. 23*a* shows a microscope image of surfactant (IIa) stabilized droplets containing cells after incubation for 2 hours at 37° C. The scale bar represents 100 μm. The arrows indicate cells (which appear as small white circles) in the droplets. FIG. 23*b* shows the percentage of viable cells in the samples from non-encapsulated CHO cells (Bulk-left), cells encapsulated in droplets using Pico-Surf™ 1 (middle), and cells encapsulated in droplets using surfactant (IIa) (right) after incubation for 2 hours at 37° C. This shows that the viability of cells encapsulated in droplets using surfactant (IIa) is comparable to the viability of cells encapsulated in droplets using Pico-Surf™ 1 and to the viability of non-encapsulated cells.

Figure 24A:
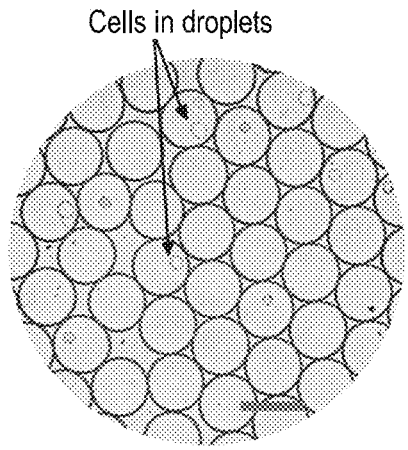
FIG. 24*a* is a microscope image of surfactant (IIb) stabilized droplets containing cells after incubation for 2 hours at 37° C.
Figure 24B:
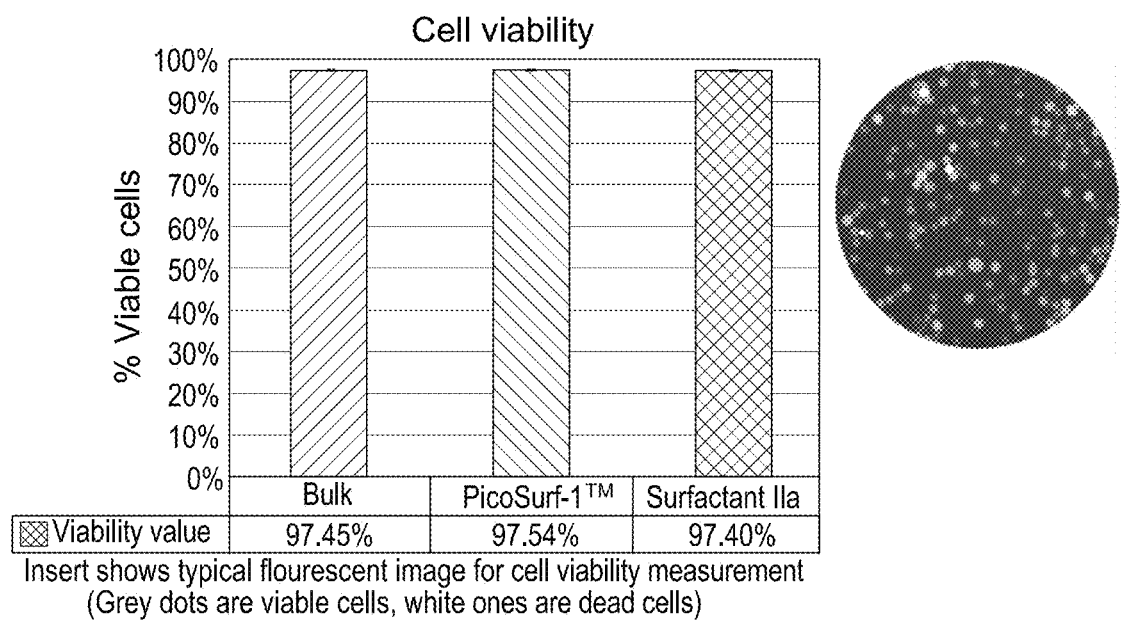
FIG. 24*b* is a bar graph showing the percentage of viable cells in surfactant (IIb) stabilized droplets containing cells after incubation for 2 hours at 37° C.

FIG. 24 shows the results of the cell viability study for cells encapsulated in droplets using surfactant (IIb). FIG. 24*a* shows a microscope image of surfactant (IIb) stabilized droplets containing cells after incubation for 2 hours at 37° C. The scale bar represents 100 μm. The arrows indicate cells (which appear as small white circles) in the droplets. FIG. 24*b* shows the percentage of viable cells in the samples from non-encapsulated CHO cells (Bulk-left), cells encapsulated in droplets using Pico-Surf™ 1 (middle), and cells encapsulated in droplets using surfactant (IIb) (right) after incubation for 2 hours at 37° C. This shows that the viability of cells encapsulated in droplets using surfactant (IIb) is comparable to the viability of cells encapsulated in droplets using Pico-Surf™ 1 and to the viability of non-encapsulated cells. The inset image in FIG. 24*b* shows a typical fluorescent image for the cell viability measurement. When viewed in colour, viable cells appear green and dead cells appear red and the image confirms the afore-described result.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A surfactant of formula (II),

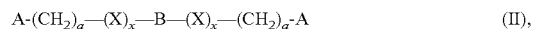

A-(CH$_2$)$_a$—(X)$_x$—B—(X)$_x$—(CH$_2$)$_a$-A     (II), wherein,
each A is a perfluoropolyether and comprises a repeat unit of the formula:

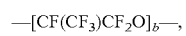

—[CF(CF$_3$)CF$_2$O]$_h$—, wherein h is a positive integer;
a is a positive integer;
X is either a covalent bond or a linking group;
x is a positive integer;
B is a polyalkylene oxide unit; and
each A, X, a, and x may be the same or different.

2. A surfactant as claimed in claim 1, wherein each A comprises a repeat unit of the formula:

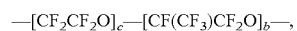

—[CF$_2$CF$_2$O]$_c$—[CF(CF$_3$)CF$_2$O]$_b$—, wherein b is a positive integer and c is 0 or a positive integer; or wherein each A consists of the formula:

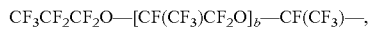

wherein b is a positive integer.

3. A surfactant as claimed in claim 1, wherein b is an integer from 1 to 100.

4. A surfactant as claimed in claim 1, wherein each a is an integer from 1 to 5.

5. A surfactant as claimed in claim 1, wherein at least one X is a covalent bond.

6. A surfactant as claimed in claim 1, wherein at least one X is a linking group selected from the group consisting of —C(O)NH—, —C(O)NMe-, —NHC(O)—, —NMeC(O)—, —C(O)S—, —SC(O)—, —C(O)O—, —OC(O)—, —OC(O)O—, —OC(O)NH—, —OC(O)NMe-, —O—, —S—, —NHC(O)NH—, —NMeC(O)NH—, —NHC(O)NMe-, —NHC(O)O—, —NMeC(O)O—, —SO$_2$NH—, —NHSO$_2$—, —NHSO$_2$—C$_6$H$_4$—O—, —O—C$_6$H$_4$—SO$_2$NH—, and linking groups of the formula -D-(E)$_h$-(G)$_d$- and -(G)$_d$-(E)$_h$-D-, wherein D is selected from NH, NMe, C(O), CO$_2$, O and SO$_g$ wherein g is 0, 1 or 2, E is selected from alkylene, optionally substituted arylene and optionally substituted heteroarylene, h is 0 or 1, G is selected from C(O)NH, CO$_2$, NH, NMe, O, C(O), S and SO$_2$NH, and d is 0 or 1.

7. A surfactant as claimed in claim 1, wherein each x is 1.

8. A surfactant as claimed in claim 1, wherein each B comprises a group selected from a group consisting of a polyethylene oxide unit, a polypropylene oxide unit, and a unit of the formula

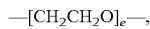

wherein e is a positive integer.

9. A surfactant as claimed in claim 1, wherein each B consists of a unit of the formula:

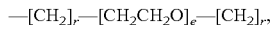

wherein e is a positive integer and r and r' are each independent 0, 1, 2, 3, 4 or 5.

10. A surfactant as claimed in claim 1, wherein each B consists of the formula:

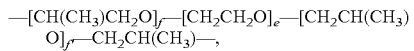

wherein e, f and f' are each independently a positive integer.

11. A surfactant as claimed in claim 10, wherein e is an integer from 1 to 100.

12. A surfactant as claimed in claim 10, wherein f and f' are each independently an integer from 1 to 50.

13. A surfactant as claimed in claim 1 selected from the group consisting of:

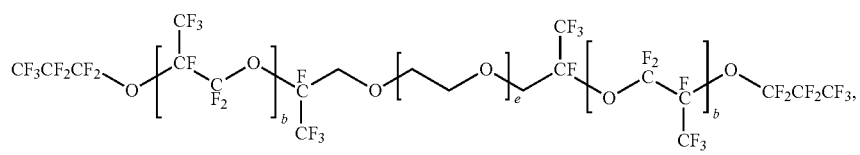

(IIa)

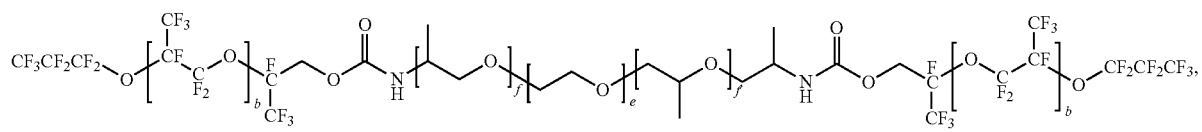

(IIb)

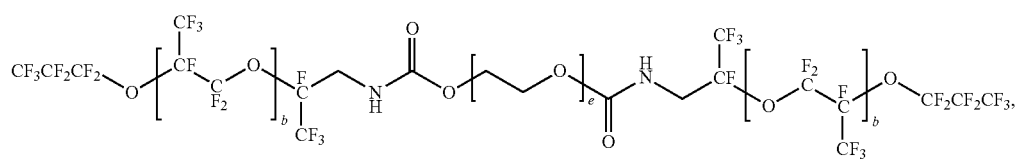

(IIc)

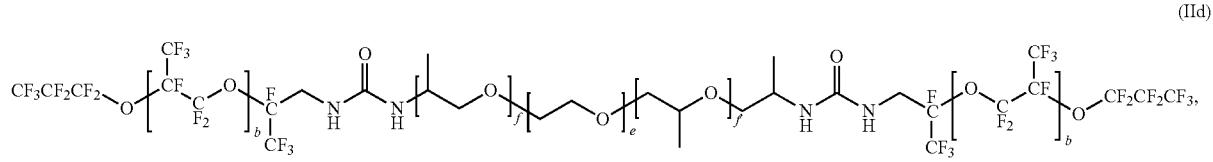

(IId)

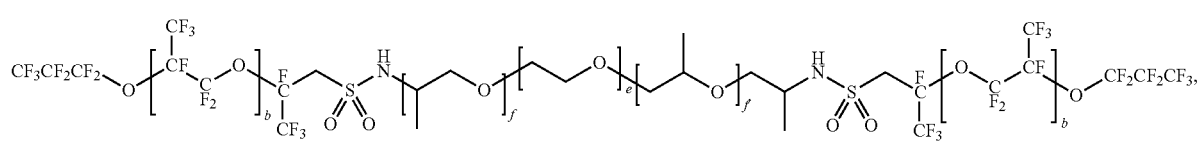

(IIe)

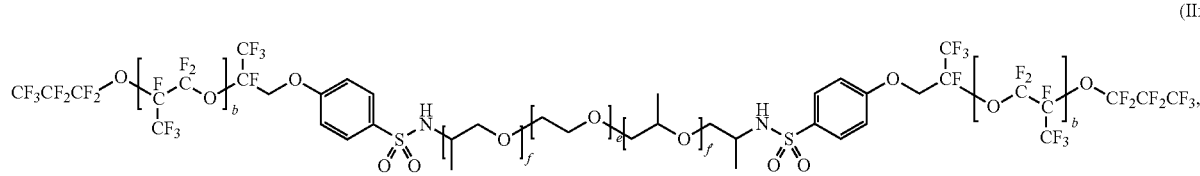

(IIf)

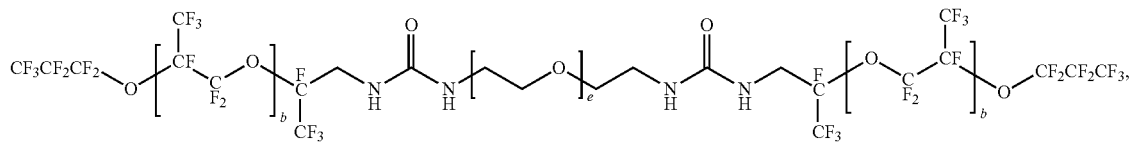
(IIg)
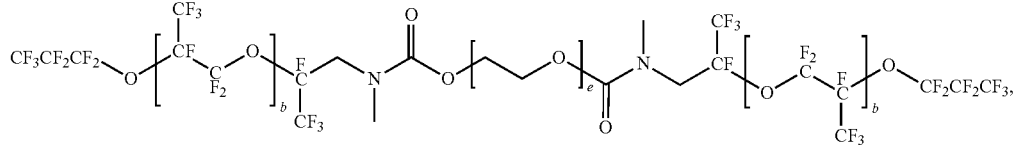
(IIh)
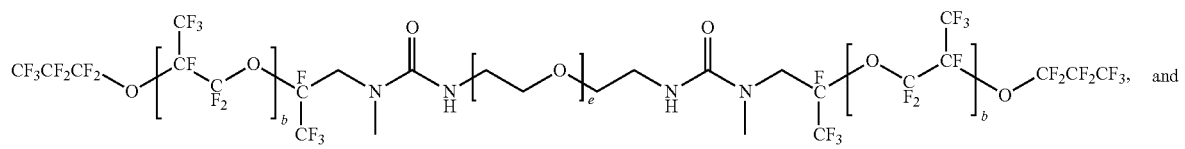
(IIi)
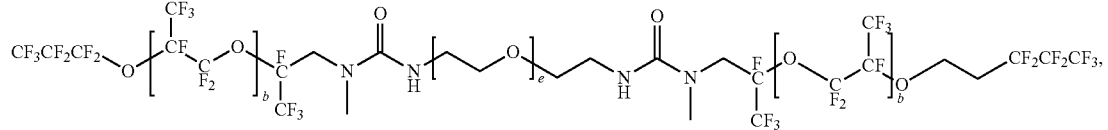
(IIj)
wherein each b, e, f and f' are each independently a positive integer.
14. A surfactant as claimed in claim 1 selected from the group consisting of:
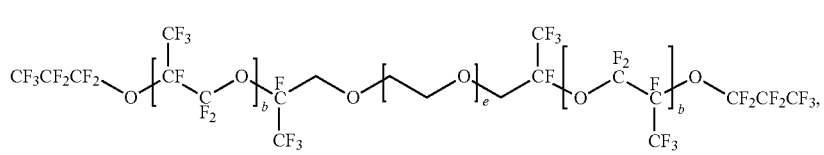
(IIa)
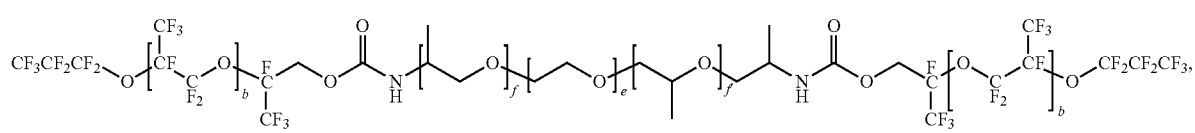
(IIb)
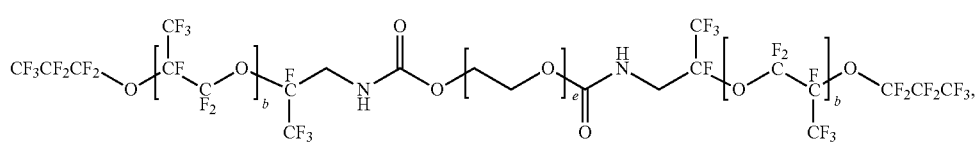
(IIc)
(IIg)
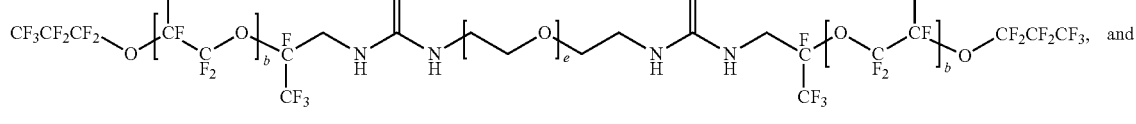
and
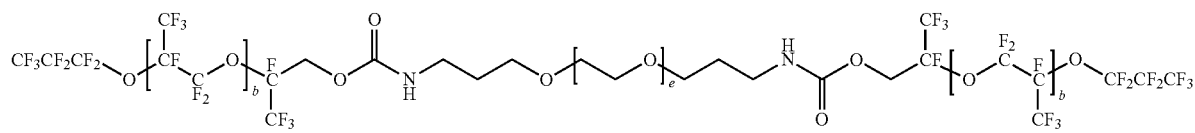
(IIj)

wherein each b, e, f and f' are each independently a positive integer.

15. A method for making a surfactant as claimed in claim 1, the method comprising:
reacting a compound of the formula (VIII)

$$A\text{-}(CH_2)_a\text{---}Y \quad (VIII),$$

wherein A is a perfluoropolyether and comprises a repeat unit of the formula:

$$\text{---}[CF(CF_3)CF_2O]_b\text{---},$$

wherein b is a positive integer;
a is a positive integer; and
Y comprises a nucleophilic group, a leaving group, or an isocyanate group, with a compound of the formula (XI)

$$Z\text{---}B\text{---}Z \quad (XI),$$

wherein B is a polyalkylene oxide, and each Z comprises a nucleophilic group, a leaving group or an isocyanate group.

16. A method as claimed in claim 15, wherein each A comprises a repeat unit of the formula:

$$\text{---}[CF_2CF_2O]_c\text{---}[CF(CF_3)CF_2O]_h\text{---},$$

wherein h is a positive integer and c is 0 or a positive integer; or
wherein each A consists of the formula:

$$CF_3CF_2CF_2O\text{---}[CF(CF_3)CF_2O]_b\text{---}CF(CF_3)\text{---},$$

wherein b is a positive integer.

17. A method as claimed in claim 15, wherein a is an integer from 1 to 5.

18. A method as claimed in claim 15, wherein each B comprises a group selected from a group consisting of a polyethylene oxide unit, a polypropylene oxide unit, and a unit of the formula:

$$\text{---}[CH_2CH_2O]_e\text{---},$$

wherein e is a positive integer.

19. A method as claimed in claim 15, wherein B consists of the formula —[CH$_2$]$_r$—[CH$_2$CH$_2$O]$_e$—[CH$_2$]$_{r'}$— or —[CH(CH$_3$)CH$_2$O]$_f$—[CH$_2$CH$_2$O]$_e$[CH$_2$CH(CH$_3$)]$_{f'}$—CH$_2$CH(CH$_3$)—, wherein e, f and f' are each independently a positive integer and r and r' are each independently 0, 1, 2, 3, 4 or 5.

20. A method as claimed in claim 15, wherein Y is selected from NH2, NHMe, OH, SH, NCO, Cl, Br, I, OMe, OEt, OTs, OMs, OTf, OC$_6$H$_4$NO$_2$, NHC(O)L, C(O)L, OC(O)L, SO$_2$L and OC$_6$H$_4$SO$_2$L, wherein L is selected from Cl, Br, I, OMe, OEt, OFT, OTs, OMs, OTf and OC$_6$H$_4$NO$_2$ and/or wherein Z is selected from NH$_2$, OH, SH, NCO, Cl, Br, I, OMe, OEt, OH, OTs, OMs, OTf, OC$_6$H$_4$NO$_2$, NHC(O)L, C(O)L, OC(O)L, SO$_2$L and OC$_6$H$_4$SO$_2$L, wherein L is selected from Cl, Br, I, OMe, OEt, OH, OTs, OMs, OTf and OC$_6$H$_4$NO$_2$.

21. A method as claimed in claim 15, wherein the compound of the formula (VIII) is selected from the group consisting of CF$_3$CF$_2$CF$_2$O—[CF(CF$_3$)CF$_2$O]$_b$—CF(CF$_3$)—CH$_2$OC$_6$H$_4$SO$_2$Cl, CF$_3$CF$_2$CF$_2$O—[CF (CF$_3$)CF$_2$O]$_b$—CF(CF$_3$)—CH$_2$SO$_2$Cl, CF$_3$CF$_2$CF$_2$O—[CF(CF$_3$)CF$_2$O]$_b$—CF(CF$_3$)—CH$_2$OC, (O)OC$_6$H$_4$NO$_2$, CF$_3$CF$_2$CF$_2$O—[CF(CF$_3$)CF$_2$O]$_b$—CF(CF$_3$)—CH$_2$OH, CF$_3$CF$_2$CF$_2$O—[CF(CF$_3$)CF$_2$O]$_b$—CF(CF$_3$)—CH$_2$NCO, CF$_3$CF$_2$CF$_2$O—[CF(CF$_3$)CF$_2$O]$_b$—CF(CF$_3$)—CH$_2$NH$_2$ and CF$_3$CF$_2$CF$_2$O—[CF(CF$_3$)CF$_2$O]$_b$—CF(CF$_3$)—CH$_2$NHMe, wherein b is an integer from 1 to 50 and/or wherein the compound of formula (XI) is selected from TsO—CH$_2$CH$_2$—[OCH$_2$CH$_2$]$_c$—OTs, MsO—CH$_2$CH$_2$—[OCH$_2$CH$_2$]$_e$—OMs, NO$_2$C$_6$H$_4$OC(O)O—CH$_2$CH$_2$—[OCH$_2$CH$_2$]$_e$—OC(O)OC$_6$H$_4$NO$_2$, OCN—CH$_2$CH$_2$—[OCH$_2$CH$_2$]$_e$—NCO, H$_2$N—[CH$_2$]$_3$—[OCH$_2$CH$_2$]$_e$—CH$_2$—NH$_2$ and N$_2$N—[CH(CH$_3$)CH$_2$O]$_f$—[CH$_2$CH$_2$O]$_e$—[CH$_2$CH(CH$_3$)O]$_{f'}$—CH$_2$CH(CH$_3$)—NH$_2$ wherein e is an integer from 1 to 100 and f and f are each independently an integer from 1 to 50.

22. A composition comprising a surfactant, wherein the surfactant has a formula selected from the group consisting of $$A\text{-}(CH_2)_a\text{---}(X)_x\text{---}B\text{---}(X)_x\text{---}(CH_2)_a\text{-}A \quad (II),$$

wherein,
each A is a perfluoropolyether and comprises a repeat unit of the formula:

$$\text{---}[CF(CF_3)CF_2O]_b\text{---},$$

wherein h is a positive integer;
a is a positive integer;
X is either a covalent bond or a linking group;
x is a positive integer;
B is a polyalkylene oxide unit; and
each A, X, a and x may be the same or different.

23. The composition as claimed in claim 22, in the form of an emulsion comprising:
a discontinuous aqueous phase;
a continuous oil phase; and
said surfactant.

24. A method of preparing an emulsion comprising:
(i) preparing an aqueous phase;
(ii) preparing an oil phase; and
(iii) mixing said aqueous phase, said oil phase and a surfactant having a formula selected from the group consisting of:

$$A\text{-}(CH_2)_a\text{---}(X)_x\text{---}B\text{---}(X)_x\text{---}(CH_2)_a\text{-}A \quad (II),$$

wherein,
each A is a perfluom olyether and comprises a repeat unit of the formula:

$$\text{---}[CF(CF_3)CF_2O]_b\text{---}$$

wherein b is a positive integer;
a is a positive integer;
X is either a covalent bond or a linking group;
x is a positive integer;
B is a polyalkylene oxide unit; and
A, X, a and x may be the same or different, to form said emulsion.

25. A method as claimed in claim 24, wherein said mixing is by a flow focus junction of a microfluidic device.

26. A method comprising performing one or more chemical and/or biological reactions, and/or biological processes in the discontinuous aqueous phase of an emulsion as claimed in claim 23.

* * * * *